US011795208B2

(12) United States Patent
Doudna et al.

(10) Patent No.: US 11,795,208 B2
(45) Date of Patent: Oct. 24, 2023

(54) MODULATORS OF CAS9 POLYPEPTIDE ACTIVITY AND METHODS OF USE THEREOF

(71) Applicant: The Regents of the University of California, Oakland, CA (US)

(72) Inventors: Jennifer A Doudna, Berkeley, CA (US); Kyle E. Watters, Moraga, CA (US); Christof Fellmann, Berkeley, CA (US); Haridha Shivram, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 338 days.

(21) Appl. No.: 17/039,195

(22) Filed: Sep. 30, 2020

(65) Prior Publication Data
US 2021/0095004 A1 Apr. 1, 2021

Related U.S. Application Data

(60) Provisional application No. 62/908,892, filed on Oct. 1, 2019.

(51) Int. Cl.
| C07K 14/435 | (2006.01) |
| C07K 14/81 | (2006.01) |
| C12N 15/85 | (2006.01) |

(52) U.S. Cl.
CPC .......... *C07K 14/8107* (2013.01); *C12N 15/85* (2013.01); *C07K 2319/09* (2013.01); *C07K 2319/40* (2013.01)

(58) Field of Classification Search
None
See application file for complete search history.

(56) References Cited

U.S. PATENT DOCUMENTS

2011/0112179 A1* 5/2011 Airan ............... C07K 14/70571
435/325

FOREIGN PATENT DOCUMENTS

WO WO 2017/160689 9/2017

OTHER PUBLICATIONS

An, et al.; "Intrinsic disorder is essential for Cas9 inhibition of anti-CRISPR AcrIIA5"; Nucleic Acids Research; vol. 48, No. 13, pp. 7584-7594 (2020).
Bondy-Denomy; "Protein inhibitors of CRIPR-Cas9"; ACS Chem. Biol.; vol. 13, No. 2, pp. 417-423 (Feb. 16, 2018).
Eitzinger, et al.; "Machine learning predicts new anti-CRISPR proteins"; Nucleic Acids Research; vol. 48, No. 9, pp. 4698-4708 (2020).
Forsberg, et al.; "Functional metagenomics-guided discovery of potent Cas9 inhibitors in the human microbiome"; eLife; 32 pages (2019).
Garcia, et al.; "Anti-CRISPR AcrIIA5 Potently Inhibits All Cas9 Homologs Used for Genome Editing"; Cell Rep.; vol. 29, No. 7, pp. 1739-1746 (Nov. 12, 2019).
Hynes, et al.;"Widespread anti-CRISPR proteins in virulent bacteriophages inhibit a range of Cas9 proteins"; Nature Communications; vol. 9, No. 2919, 10 pages (2018).
Jiang, et al.; "Temperature-Responsive Competitive Inhibition of CRISPR-Cas9"; Mol. Cell.; vol. 73, No. 3, pp. 601-610 (Feb. 7, 2019).
Lee, et al.; "Potent Cas9 Inhibition in Bacterial and Human Cells by AcrIIC4 and AcrIIC5 Anti-CRISPR Proteins"; mBio; vol. 9, Issue 6, 17 pages (2018).
Mahendra, et al.; "Broad-spectrum anti-CRISPR proteins facilitate horizontal gene transfer"; Nat. Microbiol.; vol. 5, No. 4, pp. 620-629 (Apr. 2020).
Mathony, et al.; "Computational design of anti-CRISPR proteins with improved inhibition potency"; Nature Chemical Biology; vol. 16, pp. 725-730 (Jul. 2020).
Osuna, et al.; *Listeria* Phages Induce Cas9 Degradation to Protect Lysogenic Genomes; Cell Host & Microbe; vol. 28, pp. 31-40 (2020).
Pawluk, et al.; "Naturally occurring off-switches for CRISPR-Cas9"; Cell; vol. 167, No. 7, pp. 1829-1838 (Dec. 15, 2016).
Uribe, et al.; "Discovery and Characterization of Cas9 Inhibitors Disseminated across Seven Bacterial Phyla"; Cell Host & Microbe; vol. 25, pp. 233-241 (2019).
Yang, et al.; "Inhibition Mechanism of an Anti-CRISPR Suppressor AcrIIA4 Targeting SpyCas9"; Mol. Cell.; vol. 67, No. 1, pp. 117-127 (Jul. 6, 2017).
Basgall, et al.; "Gene drive inhibition by the anti-CRISPR proteins AcrIIA2 and AcrIIA4 in *Saccharomyces cerevisiae*"; Microbiology; vol. 164, pp. 464-474 (2018).
Bondy-Denomy, et al.; "Bacteriophage genes that inactivate the CRISPR/Cas bacterial immune system"; Nature; vol. 493, No. 7432, pp. 429-432 (Jan. 17, 2013).
Dong, et al.; "Structural basis of CRISPR-SpyCas9 inhibition by an anti-CRISPR protein"; Nature; vol. 546, pp. 436-439 (Jun. 15, 2017).
Harrington, et al.; "A Broad-Spectrum Inhibitor of CRISPR-Cas9"; Cell; vol. 170, No. 6, pp. 1224-1233.e15 (Sep. 7, 2017).
Hynes, et al.; "An anti-CRISPR from a virulent streptococcal phage inhibits *Streptococcus pyogenes* Cas9"; Nature Microbiolog; vol. 2, pp. 1374-1380 (Oct. 2017).
Ka, et al.; "Crystal structure of an anti-CRISPR protein, AcrIIA1"; Nucleic Acids Research; vol. 46, No. 1, pp. 485-492 (2018).

(Continued)

*Primary Examiner* — Michael D Pak
(74) *Attorney, Agent, or Firm* — BOZICEVIC FIELD & FRANCIS, LLP; Paula A. Borden

(57) ABSTRACT

The present disclosure provides polypeptides that inhibit activity of a CRISPR/Cas effector polypeptide, nucleic acids encoding the polypeptides, and systems comprising the polypeptides and/or nucleic acids encoding the polypeptides. The present disclosure provides methods of inhibiting activity of a CRISRP/Cas effector polypeptide.

20 Claims, 18 Drawing Sheets
Specification includes a Sequence Listing.

(56) References Cited

OTHER PUBLICATIONS

Kim, et al.; "Solution structure and dynamics of anti-CRISPR AcrIIA4, the Cas9 inhibitor"; Scientific Reports; vol. 8, 9 pages (2018).
Nakamura, et al.; "Anti-CRISPR-mediated control of gene editing and synthetic circuits in eukaryotic cells"; vol. 10, No. 194, 11 pages (2019).
Pawluk, et al.; "Inactivation of CRISPR-Cas systems by anti-CRISPR proteins in diverse bacterial species"; Nature Microbiology; vol. 1, 6 pages (Aug. 2016).
Pawluk, et al.; "Anti-CRISPR: discovery, mechanism and function"; Nature Reviews Microbiology; vol. 16, pp. 12-17 (Jan. 2018).
Rauch, et al.; "Inhibition of CRISPR-Cas9 with Bacteriophage Proteins"; Cell; vol. 168, Nos. 1-2, pp. 150-158.e10 (Jan. 12, 2017).
Shin, et al.; "Disabling Cas9 by an anti-CRISPR DNA mimic"; Sci. Adv.; vol. 3, 9 pages (Jul. 12, 2017).
Stanley, et al.; "Anti-CRISPR Associated Proteins are Crucial Repressors of Anti-CRISPR Transcription"; Cell; vol. 178, No. 6, pp. 1452-1464.e13 (Sep. 5, 2019).
Zhu, et al.; "Diverse Mechanisms of CRISPR-Cas9 Inhibition by Type IIC Anti-CRISPR Proteins"; Mol. Cell.; vol. 74, No. 2, pp. 296-309.e7 (Apr. 18, 2019).

\* cited by examiner

FIG. 5

SauCas9 amino acid

MGKRNYILGLDIGITSVGYGIIDYETRDVIDAGVRLFKEANVENNEGRRSKRGARRLKR
RRRHRIQRVKKLLFDYNLLTDHSELSGINPYEARVKGLSQKLSEEEFSAALLHLAKRRG
VHNVNEVEEDTGNELSTKEQISRNSKALEEKYVAELQLERLKKDGEVRGSINRFKTSDY
VKEAKQLLKVQKAYHQLDQSFIDTYIDLLETRRTYYEGPGEGSPFGWKDIKEWYEMLMG
HCTYFPEELRSVKYAYNADLYNALNDLNNLVITRDENEKLEYYEKFQIIENVFKQKKKP
TLKQIAKEILVNEEDIKGYRVTSTGKPEFTNLKVYHDIKDITARKEIIENAELLDQIAK
ILTIYQSSEDIQEELTNLNSELTQEEIEQISNLKGYTGTHNLSLKAINLILDELWHTND
NQIAIFNRLKLVPKKVDLSQQKEIPTTLVDDFILSPVVKRSFIQSIKVINAIIKKYGLP
NDIITELAREKNSKDAQKMINEMQKRNRQTNERIEEIIRTTGKENAKYLIEKIKLHDMQ
EGKCLYSLEAIPLEDLLNNPFNYEVDHIIPRSVSFDNSFNNKVLVKQEENSKKGNRTPF
QYLSSSDSKISYETFKKHILNLAKGKGRISKTKKEYLLEERDINRFSVQKDFINRNLVD
TRYATRGLMNLLRSYFRVNNLDVKVKSINGGFTSFLRRKWKFKKERNKGYKHHAEDALI
IANADFIFKEWKKLDKAKKVMENQMFEEKQAESMPEIETEQEYKEIFITPHQIKHIKDF
KDYKYSHRVDKKPNRELINDTLYSTRKDDKGNTLIVNNLNGLYDKDNDKLKKLINKSPE
KLLMYHHDPQTYQKLKLIMEQYGDEKNPLYKYYEETGNYLTKYSKKDNGPVIKKIKYYG
NKLNAHLDITDDYPNSRNKVVKLSLKPYRFDVYLDNGVYKFVTVKNLDVIKKENYYEVN
SKCYEEAKKLKKISNQAEFIASFYNNDLIKINGELYRVIGVNNDLLNRIEVNMIDITYR
EYLENMNDKRPPRIIKTIASKTQSIKKYSTDILGNLYEVKSKKHPQIIKKG (SEQ ID NO:44)

FIG. 6

SpyCas9 amino acid

MDKKYSIGLDIGTNSVGWAVITDEYKVPSKKFKVLGNTDRHSIKKNLIGALLFDSGETAEATRLKRTA
RRRYTRRKNRICYLQEIFSNEMAKVDDSFFHRLEESFLVEEDKKHERHPIFGNIVDEVAYHEKYPTIYH
LRKKLVDSTDKADLRLIYLALAHMIKFRGHFLIEGDLNPDNSDVDKLFIQLVQTYNQLFEENPINASGV
DAKAILSARLSKSRRLENLIAQLPGEKKNGLFGNLIALSLGLTPNFKSNFDLAEDAKLQLSKDTYDDDL
DNLLAQIGDQYADLFLAAKNLSDAILLSDILRVNTEITKAPLSASMIKRYDEHHQDLTLLKALVRQQLP
EKYKEIFFDQSKNGYAGYIDGGASQEEFYKFIKPILEKMDGTEELLVKLNREDLLRKQRTFDNGSIPHQ
IHLGELHAILRRQEDFYPFLKDNREKIEKILTFRIPYYVGPLARGNSRFAWMTRKSEETITPWNFEEVV
DKGASAQSFIERMTNFDKNLPNEKVLPKHSLLYEYFTVYNELTKVKYVTEGMRKPAFLSGEQKKAIVD
LLFKTNRKVTVKQLKEDYFKKIECFDSVEISGVEDRFNASLGTYHDLLKIIKDKDFLDNEENEDILEDIVL
TLTLFEDREMIEERLKTYAHLFDDKVMKQLKRRRYTGWGRLSRKLINGIRDKQSGKTILDFLKSDGFA
NRNFMQLIHDDSLTFKEDIQKAQVSGQGDSLHEHIANLAGSPAIKKGILQTVKVVDELVKVMGRHK
PENIVIEMARENQTTQKGQKNSRERMKRIEEGIKELGSQILKEHPVENTQLQNEKLYLYYLQNGRDM
YVDQELDINRLSDYDVDHIVPQSFLKDDSIDNKVLTRSDKNRGKSDNVPSEEVVKKMKNYWRQLLN
AKLITQRKFDNLTKAERGGLSELDKAGFIKRQLVETRQITKHVAQILDSRMNTKYDENDKLIREVKVIT
LKSKLVSDFRKDFQFYKVREINNYHHAHDAYLNAVVGTALIKKYPKLESEFVYGDYKVYDVRKMIAKS
EQEIGKATAKYFFYSNIMNFFKTEITLANGEIRKRPLIETNGETGEIVWDKGRDFATVRKVLSMPQVN
IVKKTEVQTGGFSKESILPKRNSDKLIARKKDWDPKKYGGFDSPTVAYSVLVVAKVEKGKSKKLKSVK
ELLGITIMERSSFEKNPIDFLEAKGYKEVKKDLIIKLPKYSLFELENGRKRMLASAGELQKGNELALPSKY
VNFLYLASHYEKLKGSPEDNEQKQLFVEQHKHYLDEIIEQISEFSKRVILADANLDKVLSAYNKHRDKPI
REQAENIIHLFTLTNLGAPAAFKYFDTTIDRKRYTSTKEVLDATLIHQSITGLYETRIDLSQLGGD (SEQ
ID NO:45)

FIG. 11

AcrIIA-Cand27 amino acid sequence

MRKTIERLLNSELSSNSIAVRTGVSQAVISKLRNGKKELGNLTLNSAEKLFEYQKEMEKVDTWIVYRG
RTADMNKSYIAEGSTYEEVYNNFVDKYGYDVLDEDIYEIQLLKKNGENLDDYDVDSDGINNYDKLDE
FRESDYVDLEDYDYRELFENSSSQVYYHEFEITHE* (SEQ ID NO:2)

FIG. 12

AcrIIA-Cand27 nucleotide sequence, human codon optimized

ATGAGAAAGACAATAGAGCGGCTGCTTAACTCTGAGCTTTCTTCAAACAGTATCGCTGTACGAA
CCGGCGTAAGCCAGGCAGTGATCTCTAAACTGCGCAACGGAAAAAAGAACTGGGTAACTTGA
CTCTGAACAGTGCGGAAAAACTGTTCGAGTACCAGAAAGAGATGGAGAAGGTTGATACCTGGA
TTGTGTATCGCGGGAGAACGGCTGATATGAACAAGTCCTATATAGCTGAGGGAAGTACATATG
AGGAAGTATATAATAATTTTGTAGATAAATACGGTTATGACGTACTTGACGAGGACATATATGA
GATTCAACTCCTCAAAAAGAATGGCGAGAATCTTGACGACTATGATGTAGACTCCGACGGGATC
AATAATTATGATAAGCTGGACGAGTTTCGGGAGAGCGACTACGTCGACCTGGAAGATTACGAT
TACAGGGAACTCTTTGAGAACAGCAGCAGCCAAGTGTACTATCACGAGTTTGAGATAACCCACG
AGTGA (SEQ ID NO:46)

FIG. 13

AcrIIA-Cand27-trunc amino acid sequence

MEKVDTWIVYRGRTADMNKSYIAEGSTYEEVYNNFVDKYGYDVLDEDIYEIQLLKKNGENLDDYDV
DSDGINNYDKLDEFRESDYVDLEDYDYRELFENSSSQVYYHEFEITHE* (SEQ ID NO:4)

FIG. 14

AcrIIA-Cand27-trunc nucleotide sequence, human codon optimized

ATGGAGAAGGTTGATACCTGGATTGTGTATCGCGGGAGAACGGCTGATATGAACAAGTCCTAT
ATAGCTGAGGGAAGTACATATGAGGAAGTATATAATAATTTTGTAGATAAATACGGTTATGACG
TACTTGACGAGGACATATATGAGATTCAACTCCTCAAAAAGAATGGCGAGAATCTTGACGACTA
TGATGTAGACTCCGACGGGATCAATAATTATGATAAGCTGGACGAGTTTCGGGAGAGCGACTA
CGTCGACCTGGAAGATTACGATTACAGGGAACTCTTTGAGAACAGCAGCAGCCAAGTGTACTAT
CACGAGTTTGAGATAACCCACGAGTGA (SEQ ID NO:47)

FIG. 15

AcrIIA-Cand9 amino acid sequence

LKKTIEKLLNSDLNSNYIAKKTGVEQSTIYRLRTGERQLGKLGLDSAERLYNYQKEIENMKSVKYISNM
SKQEKGYRVYVNVVNEDTDKGFLFPSVPKEVIENDKIDELFNFEHHKPYVQKAKSRYDKNGIGYKIVQ
LDEGFQKFIELNKEKMKENLDY*(SEQ ID NO:1)

FIG. 16

AcrIIA-Cand9 nucleotide sequence, human codon optimized

TTGAAGAAGACCATTGAAAAACTCTTGAACTCTGATCTCAATAGCAACTATATCGCAAAAAAGA
CTGGGGTTGAGCAAAGTACTATTTATCGCCTGAGAACGGGCGAGCGCCAGCTTGGAAAGCTCG
GCCTTGATTCTGCTGAACGACTTTACAATTACCAGAAGGAAATAGAAAACATGAAAAGTGTAAA
GTATATTTCTAATATGAGTAAACAGGAGAAGGGGTATCGGGTATATGTTAACGTGGTAAATGA
GGACACGGATAAAGGCTTTCTTTTCCCCTCTGTCCCAAAGGAGGTGATAGAAACGATAAGATC
GACGAACTTTTCAATTTTGAACATCACAAACCCTACGTGCAAAAAGCGAAATCCAGGTATGACA
AGAATGGAATCGGATATAAAATAGTTCAACTTGACGAAGGTTTCCAAAAATTTATTGAATTGAA
CAAAGAGAAGATGAAGGAAAACCTTGACTATTAG (SEQ ID NO:48)

FIG. 17

AcrIIA-Cand9-trunc amino acid sequence

MKSVKYISNMSKQEKGYRVYVNVVNEDTDKGFLFPSVPKEVIENDKIDELFNFEHHKPYVQKAKSRY
DKNGIGYKIVQLDEGFQKFIELNKEKMKENLDY* (SEQ ID NO:3)

FIG. 18

AcrIIA-Cand9-trunc nucleotide sequence, human codon optimized

ATGAAAAGTGTAAAGTATATTTCTAATATGAGTAAACAGGAGAAGGGGTATCGGGTATATGTT
AACGTGGTAAATGAGGACACGGATAAAGGCTTTCTTTTCCCCTCTGTCCCAAAGGAGGTGATAG
AAAACGATAAGATCGACGAACTTTTCAATTTTGAACATCACAAACCCTACGTGCAAAAAGCGAA
ATCCAGGTATGACAAGAATGGAATCGGATATAAAATAGTTCAACTTGACGAAGGTTTCCAAAAA
TTTATTGAATTGAACAAAGAGAAGATGAAGGAAAACCTTGACTATTAG (SEQ ID NO:49)

SEQUENCE LISTING

```
<160> NUMBER OF SEQ ID NOS: 49

<210> SEQ ID NO 1
<211> LENGTH: 159
<212> TYPE: PRT
<213> ORGANISM: Artificial sequence
<220> FEATURE:
<223> OTHER INFORMATION: synthetic sequence

<400> SEQUENCE: 1

Leu Lys Lys Thr Ile Glu Lys Leu Leu Asn Ser Asp Leu Asn Ser Asn
1               5                   10                  15

Tyr Ile Ala Lys Lys Thr Gly Val Glu Gln Ser Thr Ile Tyr Arg Leu
            20                  25                  30

Arg Thr Gly Glu Arg Gln Leu Gly Lys Leu Gly Leu Asp Ser Ala Glu
        35                  40                  45

Arg Leu Tyr Asn Tyr Gln Lys Glu Ile Glu Asn Met Lys Ser Val Lys
    50                  55                  60

Tyr Ile Ser Asn Met Ser Lys Gln Glu Lys Gly Tyr Arg Val Tyr Val
65                  70                  75                  80

Asn Val Val Asn Glu Asp Thr Asp Lys Gly Phe Leu Phe Pro Ser Val
                85                  90                  95

Pro Lys Glu Val Ile Glu Asn Asp Lys Ile Asp Glu Leu Phe Asn Phe
            100                 105                 110

Glu His His Lys Pro Tyr Val Gln Lys Ala Lys Ser Arg Tyr Asp Lys
        115                 120                 125

Asn Gly Ile Gly Tyr Lys Ile Val Gln Leu Asp Glu Gly Phe Gln Lys
    130                 135                 140

Phe Ile Glu Leu Asn Lys Glu Lys Met Lys Glu Asn Leu Asp Tyr
145                 150                 155

<210> SEQ ID NO 2
<211> LENGTH: 170
<212> TYPE: PRT
<213> ORGANISM: Artificial sequence
<220> FEATURE:
<223> OTHER INFORMATION: synthetic sequence

<400> SEQUENCE: 2

Met Arg Lys Thr Ile Glu Arg Leu Leu Asn Ser Glu Leu Ser Ser Asn
1               5                   10                  15

Ser Ile Ala Val Arg Thr Gly Val Ser Gln Ala Val Ile Ser Lys Leu
            20                  25                  30

Arg Asn Gly Lys Lys Glu Leu Gly Asn Leu Thr Leu Asn Ser Ala Glu
        35                  40                  45

Lys Leu Phe Glu Tyr Gln Lys Glu Met Glu Lys Val Asp Thr Trp Ile
    50                  55                  60

Val Tyr Arg Gly Arg Thr Ala Asp Met Asn Lys Ser Tyr Ile Ala Glu
65                  70                  75                  80

Gly Ser Thr Tyr Glu Glu Val Tyr Asn Asn Phe Val Asp Lys Tyr Gly
```

```
                85                  90                  95
Tyr Asp Val Leu Asp Glu Asp Ile Tyr Glu Ile Gln Leu Leu Lys Lys
            100                 105                 110

Asn Gly Glu Asn Leu Asp Asp Tyr Asp Val Asp Ser Asp Gly Ile Asn
            115                 120                 125

Asn Tyr Asp Lys Leu Asp Glu Phe Arg Glu Ser Asp Tyr Val Asp Leu
        130                 135                 140

Glu Asp Tyr Asp Tyr Arg Glu Leu Phe Glu Asn Ser Ser Ser Gln Val
145                 150                 155                 160

Tyr Tyr His Glu Phe Glu Ile Thr His Glu
                165                 170

<210> SEQ ID NO 3
<211> LENGTH: 100
<212> TYPE: PRT
<213> ORGANISM: Artificial sequence
<220> FEATURE:
<223> OTHER INFORMATION: synthetic sequence

<400> SEQUENCE: 3

Met Lys Ser Val Lys Tyr Ile Ser Asn Met Ser Lys Gln Glu Lys Gly
1               5                   10                  15

Tyr Arg Val Tyr Val Asn Val Asn Glu Asp Thr Asp Lys Gly Phe
            20                  25                  30

Leu Phe Pro Ser Val Pro Lys Glu Val Ile Glu Asn Asp Lys Ile Asp
        35                  40                  45

Glu Leu Phe Asn Phe Glu His His Lys Pro Tyr Val Gln Lys Ala Lys
    50                  55                  60

Ser Arg Tyr Asp Lys Asn Gly Ile Gly Tyr Lys Ile Val Gln Leu Asp
65                  70                  75                  80

Glu Gly Phe Gln Lys Phe Ile Glu Leu Asn Lys Glu Lys Met Lys Glu
                85                  90                  95

Asn Leu Asp Tyr
            100

<210> SEQ ID NO 4
<211> LENGTH: 114
<212> TYPE: PRT
<213> ORGANISM: Artificial sequence
<220> FEATURE:
<223> OTHER INFORMATION: synthetic sequence

<400> SEQUENCE: 4

Met Glu Lys Val Asp Thr Trp Ile Val Tyr Arg Gly Arg Thr Ala Asp
1               5                   10                  15

Met Asn Lys Ser Tyr Ile Ala Glu Gly Ser Thr Tyr Glu Glu Val Tyr
            20                  25                  30

Asn Asn Phe Val Asp Lys Tyr Gly Tyr Asp Val Leu Asp Glu Asp Ile
        35                  40                  45

Tyr Glu Ile Gln Leu Leu Lys Lys Asn Gly Glu Asn Leu Asp Asp Tyr
    50                  55                  60

Asp Val Asp Ser Asp Gly Ile Asn Asn Tyr Asp Lys Leu Asp Glu Phe
65                  70                  75                  80

Arg Glu Ser Asp Tyr Val Asp Leu Glu Asp Tyr Asp Tyr Arg Glu Leu
                85                  90                  95

Phe Glu Asn Ser Ser Ser Gln Val Tyr Tyr His Glu Phe Glu Ile Thr
            100                 105                 110
```

His Glu

<210> SEQ ID NO 5
<211> LENGTH: 59
<212> TYPE: PRT
<213> ORGANISM: Artificial sequence
<220> FEATURE:
<223> OTHER INFORMATION: synthetic sequence

<400> SEQUENCE: 5

```
Leu Lys Lys Thr Ile Glu Lys Leu Leu Asn Ser Asp Leu Asn Ser Asn
1               5                   10                  15

Tyr Ile Ala Lys Lys Thr Gly Val Glu Gln Ser Thr Ile Tyr Arg Leu
            20                  25                  30

Arg Thr Gly Glu Arg Gln Leu Gly Lys Leu Gly Leu Asp Ser Ala Glu
        35                  40                  45

Arg Leu Tyr Asn Tyr Gln Lys Glu Ile Glu Asn
    50                  55
```

<210> SEQ ID NO 6
<211> LENGTH: 56
<212> TYPE: PRT
<213> ORGANISM: Artificial sequence
<220> FEATURE:
<223> OTHER INFORMATION: synthetic sequence

<400> SEQUENCE: 6

```
Met Arg Lys Thr Ile Glu Arg Leu Leu Asn Ser Glu Leu Ser Ser Asn
1               5                   10                  15

Ser Ile Ala Val Arg Thr Gly Val Ser Gln Ala Val Ile Ser Lys Leu
            20                  25                  30

Arg Asn Gly Lys Lys Glu Leu Gly Asn Leu Thr Leu Asn Ser Ala Glu
        35                  40                  45

Lys Leu Phe Glu Tyr Gln Lys Glu
    50                  55
```

<210> SEQ ID NO 7
<211> LENGTH: 7
<212> TYPE: PRT
<213> ORGANISM: SV40 virus

<400> SEQUENCE: 7

```
Pro Lys Lys Lys Arg Lys Val
1               5
```

<210> SEQ ID NO 8
<211> LENGTH: 16
<212> TYPE: PRT
<213> ORGANISM: Artificial sequence
<220> FEATURE:
<223> OTHER INFORMATION: synthetic sequence

<400> SEQUENCE: 8

```
Lys Arg Pro Ala Ala Thr Lys Lys Ala Gly Gln Ala Lys Lys Lys Lys
1               5                   10                  15
```

<210> SEQ ID NO 9
<211> LENGTH: 9
<212> TYPE: PRT
<213> ORGANISM: Artificial sequence
<220> FEATURE:
<223> OTHER INFORMATION: synthetic sequence

<400> SEQUENCE: 9

```
Pro Ala Ala Lys Arg Val Lys Leu Asp
1               5
```

<210> SEQ ID NO 10
<211> LENGTH: 11
<212> TYPE: PRT
<213> ORGANISM: Artificial sequence
<220> FEATURE:
<223> OTHER INFORMATION: synthetic sequence

<400> SEQUENCE: 10

```
Arg Gln Arg Arg Asn Glu Leu Lys Arg Ser Pro
1               5                   10
```

<210> SEQ ID NO 11
<211> LENGTH: 38
<212> TYPE: PRT
<213> ORGANISM: Artificial sequence
<220> FEATURE:
<223> OTHER INFORMATION: synthetic sequence

<400> SEQUENCE: 11

```
Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
                20                  25                  30

Arg Asn Gln Gly Gly Tyr
            35
```

<210> SEQ ID NO 12
<211> LENGTH: 42
<212> TYPE: PRT
<213> ORGANISM: Artificial sequence
<220> FEATURE:
<223> OTHER INFORMATION: synthetic sequence

<400> SEQUENCE: 12

```
Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
                20                  25                  30

Asp Glu Gln Ile Leu Lys Arg Arg Asn Val
            35                  40
```

<210> SEQ ID NO 13
<211> LENGTH: 8
<212> TYPE: PRT
<213> ORGANISM: Artificial sequence
<220> FEATURE:
<223> OTHER INFORMATION: synthetic sequence

<400> SEQUENCE: 13

```
Val Ser Arg Lys Arg Pro Arg Pro
1               5
```

<210> SEQ ID NO 14
<211> LENGTH: 8
<212> TYPE: PRT
<213> ORGANISM: Artificial sequence
<220> FEATURE:
<223> OTHER INFORMATION: synthetic sequence

<400> SEQUENCE: 14

```
Pro Pro Lys Lys Ala Arg Glu Asp
```

```
<210> SEQ ID NO 15
<211> LENGTH: 8
<212> TYPE: PRT
<213> ORGANISM: Artificial sequence
<220> FEATURE:
<223> OTHER INFORMATION: synthetic sequence

<400> SEQUENCE: 15

Pro Gln Pro Lys Lys Lys Pro Leu
1               5

<210> SEQ ID NO 16
<211> LENGTH: 12
<212> TYPE: PRT
<213> ORGANISM: Mus musculus

<400> SEQUENCE: 16

Ser Ala Leu Ile Lys Lys Lys Lys Lys Met Ala Pro
1               5                   10

<210> SEQ ID NO 17
<211> LENGTH: 5
<212> TYPE: PRT
<213> ORGANISM: Influenza virus

<400> SEQUENCE: 17

Asp Arg Leu Arg Arg
1               5

<210> SEQ ID NO 18
<211> LENGTH: 7
<212> TYPE: PRT
<213> ORGANISM: Influenza virus

<400> SEQUENCE: 18

Pro Lys Gln Lys Lys Arg Lys
1               5

<210> SEQ ID NO 19
<211> LENGTH: 10
<212> TYPE: PRT
<213> ORGANISM: Hepatitis virus

<400> SEQUENCE: 19

Arg Lys Leu Lys Lys Lys Ile Lys Lys Leu
1               5                   10

<210> SEQ ID NO 20
<211> LENGTH: 10
<212> TYPE: PRT
<213> ORGANISM: Mus musculus

<400> SEQUENCE: 20

Arg Glu Lys Lys Lys Phe Leu Lys Arg Arg
1               5                   10

<210> SEQ ID NO 21
<211> LENGTH: 20
<212> TYPE: PRT
<213> ORGANISM: Homo sapiens

<400> SEQUENCE: 21

Lys Arg Lys Gly Asp Glu Val Asp Gly Val Asp Glu Val Ala Lys Lys
1               5                   10                  15
```

```
1               5                   10                  15

Lys Ser Lys Lys
            20

<210> SEQ ID NO 22
<211> LENGTH: 17
<212> TYPE: PRT
<213> ORGANISM: Homo sapiens

<400> SEQUENCE: 22

Arg Lys Cys Leu Gln Ala Gly Met Asn Leu Glu Ala Arg Lys Thr Lys
1               5                   10                  15

Lys

<210> SEQ ID NO 23
<211> LENGTH: 11
<212> TYPE: PRT
<213> ORGANISM: HIV-1

<400> SEQUENCE: 23

Tyr Gly Arg Lys Lys Arg Arg Gln Arg Arg Arg
1               5                   10

<210> SEQ ID NO 24
<211> LENGTH: 12
<212> TYPE: PRT
<213> ORGANISM: Artificial sequence
<220> FEATURE:
<223> OTHER INFORMATION: synthetic sequence

<400> SEQUENCE: 24

Arg Arg Gln Arg Arg Thr Ser Lys Leu Met Lys Arg
1               5                   10

<210> SEQ ID NO 25
<211> LENGTH: 27
<212> TYPE: PRT
<213> ORGANISM: Artificial sequence
<220> FEATURE:
<223> OTHER INFORMATION: synthetic sequence

<400> SEQUENCE: 25

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 26
<211> LENGTH: 33
<212> TYPE: PRT
<213> ORGANISM: Artificial sequence
<220> FEATURE:
<223> OTHER INFORMATION: synthetic sequence

<400> SEQUENCE: 26

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 27
<211> LENGTH: 16
```

```
<212> TYPE: PRT
<213> ORGANISM: Artificial sequence
<220> FEATURE:
<223> OTHER INFORMATION: synthetic sequence

<400> SEQUENCE: 27

Arg Gln Ile Lys Ile Trp Phe Gln Asn Arg Arg Met Lys Trp Lys Lys
1               5                   10                  15

<210> SEQ ID NO 28
<211> LENGTH: 9
<212> TYPE: PRT
<213> ORGANISM: Artificial sequence
<220> FEATURE:
<223> OTHER INFORMATION: synthetic sequence

<400> SEQUENCE: 28

Arg Lys Lys Arg Arg Gln Arg Arg Arg
1               5

<210> SEQ ID NO 29
<211> LENGTH: 8
<212> TYPE: PRT
<213> ORGANISM: Artificial sequence
<220> FEATURE:
<223> OTHER INFORMATION: synthetic sequence

<400> SEQUENCE: 29

Arg Lys Lys Arg Arg Gln Arg Arg
1               5

<210> SEQ ID NO 30
<211> LENGTH: 11
<212> TYPE: PRT
<213> ORGANISM: Artificial sequence
<220> FEATURE:
<223> OTHER INFORMATION: synthetic sequence

<400> SEQUENCE: 30

Tyr Ala Arg Ala Ala Ala Arg Gln Ala Arg Ala
1               5                   10

<210> SEQ ID NO 31
<211> LENGTH: 11
<212> TYPE: PRT
<213> ORGANISM: Artificial sequence
<220> FEATURE:
<223> OTHER INFORMATION: synthetic sequence

<400> SEQUENCE: 31

Thr His Arg Leu Pro Arg Arg Arg Arg Arg
1               5                   10

<210> SEQ ID NO 32
<211> LENGTH: 11
<212> TYPE: PRT
<213> ORGANISM: Artificial sequence
<220> FEATURE:
<223> OTHER INFORMATION: synthetic sequence

<400> SEQUENCE: 32

Gly Gly Arg Arg Ala Arg Arg Arg Arg Arg
1               5                   10

<210> SEQ ID NO 33
<211> LENGTH: 5
<212> TYPE: PRT
```

```
<213> ORGANISM: Artificial sequence
<220> FEATURE:
<223> OTHER INFORMATION: synthetic sequence

<400> SEQUENCE: 33

Gly Ser Gly Gly Ser
1               5

<210> SEQ ID NO 34
<211> LENGTH: 6
<212> TYPE: PRT
<213> ORGANISM: Artificial sequence
<220> FEATURE:
<223> OTHER INFORMATION: synthetic sequence

<400> SEQUENCE: 34

Gly Gly Ser Gly Gly Ser
1               5

<210> SEQ ID NO 35
<211> LENGTH: 5
<212> TYPE: PRT
<213> ORGANISM: Artificial sequence
<220> FEATURE:
<223> OTHER INFORMATION: synthetic sequence

<400> SEQUENCE: 35

Gly Gly Gly Gly Ser
1               5

<210> SEQ ID NO 36
<211> LENGTH: 4
<212> TYPE: PRT
<213> ORGANISM: Artificial sequence
<220> FEATURE:
<223> OTHER INFORMATION: synthetic sequence

<400> SEQUENCE: 36

Gly Gly Ser Gly
1

<210> SEQ ID NO 37
<211> LENGTH: 5
<212> TYPE: PRT
<213> ORGANISM: Artificial sequence
<220> FEATURE:
<223> OTHER INFORMATION: synthetic sequence

<400> SEQUENCE: 37

Gly Gly Ser Gly Gly
1               5

<210> SEQ ID NO 38
<211> LENGTH: 5
<212> TYPE: PRT
<213> ORGANISM: Artificial sequence
<220> FEATURE:
<223> OTHER INFORMATION: synthetic sequence

<400> SEQUENCE: 38

Gly Ser Gly Ser Gly
1               5

<210> SEQ ID NO 39
<211> LENGTH: 5
<212> TYPE: PRT
<213> ORGANISM: Artificial sequence
```

```
<220> FEATURE:
<223> OTHER INFORMATION: synthetic sequence

<400> SEQUENCE: 39

Gly Ser Gly Gly Gly
1               5

<210> SEQ ID NO 40
<211> LENGTH: 5
<212> TYPE: PRT
<213> ORGANISM: Artificial sequence
<220> FEATURE:
<223> OTHER INFORMATION: synthetic sequence

<400> SEQUENCE: 40

Gly Gly Gly Ser Gly
1               5

<210> SEQ ID NO 41
<211> LENGTH: 5
<212> TYPE: PRT
<213> ORGANISM: Artificial sequence
<220> FEATURE:
<223> OTHER INFORMATION: synthetic sequence

<400> SEQUENCE: 41

Gly Ser Ser Ser Gly
1               5

<210> SEQ ID NO 42
<211> LENGTH: 103
<212> TYPE: DNA
<213> ORGANISM: Artificial sequence
<220> FEATURE:
<223> OTHER INFORMATION: synthetic sequence

<400> SEQUENCE: 42
gcaagggcga ggagctgttc acgttttagt actctggaaa cagaatctac taaaacaagg    60
caaaatgccg tgtttatctc gtcaacttgt tggcgagatt ttt                     103

<210> SEQ ID NO 43
<211> LENGTH: 35
<212> TYPE: DNA
<213> ORGANISM: Artificial sequence
<220> FEATURE:
<223> OTHER INFORMATION: synthetic sequence

<400> SEQUENCE: 43
ctgaagttca tctgcaccac gttttagagc tatct                               35

<210> SEQ ID NO 44
<211> LENGTH: 1054
<212> TYPE: PRT
<213> ORGANISM: Artificial sequence
<220> FEATURE:
<223> OTHER INFORMATION: synthetic sequence

<400> SEQUENCE: 44

Met Gly Lys Arg Asn Tyr Ile Leu Gly Leu Asp Ile Gly Ile Thr Ser
1               5                   10                  15

Val Gly Tyr Gly Ile Ile Asp Tyr Glu Thr Arg Asp Val Ile Asp Ala
                20                  25                  30

Gly Val Arg Leu Phe Lys Glu Ala Asn Val Glu Asn Asn Glu Gly Arg
        35                  40                  45
```

-continued

Arg Ser Lys Arg Gly Ala Arg Arg Leu Lys Arg Arg Arg His Arg
    50              55                  60

Ile Gln Arg Val Lys Lys Leu Leu Phe Asp Tyr Asn Leu Leu Thr Asp
65              70                  75                  80

His Ser Glu Leu Ser Gly Ile Asn Pro Tyr Glu Ala Arg Val Lys Gly
                85                  90                  95

Leu Ser Gln Lys Leu Ser Glu Glu Phe Ser Ala Ala Leu Leu His
            100                 105                 110

Leu Ala Lys Arg Arg Gly Val His Asn Val Asn Glu Val Glu Asp
            115                 120                 125

Thr Gly Asn Glu Leu Ser Thr Lys Glu Gln Ile Ser Arg Asn Ser Lys
    130                 135                 140

Ala Leu Glu Glu Lys Tyr Val Ala Glu Leu Gln Leu Glu Arg Leu Lys
145                 150                 155                 160

Lys Asp Gly Glu Val Arg Gly Ser Ile Asn Arg Phe Lys Thr Ser Asp
                165                 170                 175

Tyr Val Lys Glu Ala Lys Gln Leu Leu Lys Val Gln Lys Ala Tyr His
            180                 185                 190

Gln Leu Asp Gln Ser Phe Ile Asp Thr Tyr Ile Asp Leu Leu Glu Thr
            195                 200                 205

Arg Arg Thr Tyr Tyr Glu Gly Pro Gly Glu Gly Ser Pro Phe Gly Trp
    210                 215                 220

Lys Asp Ile Lys Glu Trp Tyr Glu Met Leu Met Gly His Cys Thr Tyr
225                 230                 235                 240

Phe Pro Glu Glu Leu Arg Ser Val Lys Tyr Ala Tyr Asn Ala Asp Leu
                245                 250                 255

Tyr Asn Ala Leu Asn Asp Leu Asn Asn Leu Val Ile Thr Arg Asp Glu
            260                 265                 270

Asn Glu Lys Leu Glu Tyr Tyr Glu Lys Phe Gln Ile Ile Glu Asn Val
        275                 280                 285

Phe Lys Gln Lys Lys Lys Pro Thr Leu Lys Gln Ile Ala Lys Glu Ile
    290                 295                 300

Leu Val Asn Glu Glu Asp Ile Lys Gly Tyr Arg Val Thr Ser Thr Gly
305                 310                 315                 320

Lys Pro Glu Phe Thr Asn Leu Lys Val Tyr His Asp Ile Lys Asp Ile
                325                 330                 335

Thr Ala Arg Lys Glu Ile Ile Glu Asn Ala Glu Leu Leu Asp Gln Ile
            340                 345                 350

Ala Lys Ile Leu Thr Ile Tyr Gln Ser Ser Glu Asp Ile Gln Glu Glu
            355                 360                 365

Leu Thr Asn Leu Asn Ser Glu Leu Thr Gln Glu Glu Ile Glu Gln Ile
    370                 375                 380

Ser Asn Leu Lys Gly Tyr Thr Gly Thr His Asn Leu Ser Leu Lys Ala
385                 390                 395                 400

Ile Asn Leu Ile Leu Asp Glu Leu Trp His Thr Asn Asp Asn Gln Ile
                405                 410                 415

Ala Ile Phe Asn Arg Leu Lys Leu Val Pro Lys Lys Val Asp Leu Ser
            420                 425                 430

Gln Gln Lys Glu Ile Pro Thr Thr Leu Val Asp Asp Phe Ile Leu Ser
            435                 440                 445

Pro Val Val Lys Arg Ser Phe Ile Gln Ser Ile Lys Val Ile Asn Ala
    450                 455                 460

Ile Ile Lys Lys Tyr Gly Leu Pro Asn Asp Ile Ile Ile Glu Leu Ala

-continued

```
            465                 470                 475                 480
        Arg Glu Lys Asn Ser Lys Asp Ala Gln Lys Met Ile Asn Glu Met Gln
                            485                 490                 495
        Lys Arg Asn Arg Gln Thr Asn Glu Arg Ile Glu Glu Ile Ile Arg Thr
                        500                 505                 510
        Thr Gly Lys Glu Asn Ala Lys Tyr Leu Ile Glu Lys Ile Lys Leu His
                    515                 520                 525
        Asp Met Gln Glu Gly Lys Cys Leu Tyr Ser Leu Glu Ala Ile Pro Leu
                530                 535                 540
        Glu Asp Leu Leu Asn Asn Pro Phe Asn Tyr Glu Val Asp His Ile Ile
        545                 550                 555                 560
        Pro Arg Ser Val Ser Phe Asp Asn Ser Phe Asn Asn Lys Val Leu Val
                            565                 570                 575
        Lys Gln Glu Glu Asn Ser Lys Lys Gly Asn Arg Thr Pro Phe Gln Tyr
                        580                 585                 590
        Leu Ser Ser Ser Asp Ser Lys Ile Ser Tyr Glu Thr Phe Lys Lys His
                    595                 600                 605
        Ile Leu Asn Leu Ala Lys Gly Lys Gly Arg Ile Ser Lys Thr Lys Lys
                610                 615                 620
        Glu Tyr Leu Leu Glu Glu Arg Asp Ile Asn Arg Phe Ser Val Gln Lys
        625                 630                 635                 640
        Asp Phe Ile Asn Arg Asn Leu Val Asp Thr Arg Tyr Ala Thr Arg Gly
                            645                 650                 655
        Leu Met Asn Leu Leu Arg Ser Tyr Phe Arg Val Asn Asn Leu Asp Val
                        660                 665                 670
        Lys Val Lys Ser Ile Asn Gly Gly Phe Thr Ser Phe Leu Arg Arg Lys
                    675                 680                 685
        Trp Lys Phe Lys Lys Glu Arg Asn Lys Gly Tyr Lys His His Ala Glu
                690                 695                 700
        Asp Ala Leu Ile Ile Ala Asn Ala Asp Phe Ile Phe Lys Glu Trp Lys
        705                 710                 715                 720
        Lys Leu Asp Lys Ala Lys Lys Val Met Glu Asn Gln Met Phe Glu Glu
                            725                 730                 735
        Lys Gln Ala Glu Ser Met Pro Glu Ile Glu Thr Glu Gln Glu Tyr Lys
                        740                 745                 750
        Glu Ile Phe Ile Thr Pro His Gln Ile Lys His Ile Lys Asp Phe Lys
                    755                 760                 765
        Asp Tyr Lys Tyr Ser His Arg Val Asp Lys Lys Pro Asn Arg Glu Leu
                770                 775                 780
        Ile Asn Asp Thr Leu Tyr Ser Thr Arg Lys Asp Asp Lys Gly Asn Thr
        785                 790                 795                 800
        Leu Ile Val Asn Asn Leu Asn Gly Leu Tyr Asp Lys Asp Asn Asp Lys
                            805                 810                 815
        Leu Lys Lys Leu Ile Asn Lys Ser Pro Glu Lys Leu Leu Met Tyr His
                        820                 825                 830
        His Asp Pro Gln Thr Tyr Gln Lys Leu Lys Leu Ile Met Glu Gln Tyr
                    835                 840                 845
        Gly Asp Glu Lys Asn Pro Leu Tyr Lys Tyr Tyr Glu Glu Thr Gly Asn
                850                 855                 860
        Tyr Leu Thr Lys Tyr Ser Lys Lys Asp Asn Gly Pro Val Ile Lys Lys
        865                 870                 875                 880
        Ile Lys Tyr Tyr Gly Asn Lys Leu Asn Ala His Leu Asp Ile Thr Asp
                            885                 890                 895
```

```
Asp Tyr Pro Asn Ser Arg Asn Lys Val Val Lys Leu Ser Leu Lys Pro
            900                 905                 910

Tyr Arg Phe Asp Val Tyr Leu Asp Asn Gly Val Tyr Lys Phe Val Thr
            915                 920                 925

Val Lys Asn Leu Asp Val Ile Lys Lys Glu Asn Tyr Tyr Glu Val Asn
        930                 935                 940

Ser Lys Cys Tyr Glu Glu Ala Lys Lys Leu Lys Lys Ile Ser Asn Gln
945                 950                 955                 960

Ala Glu Phe Ile Ala Ser Phe Tyr Asn Asn Asp Leu Ile Lys Ile Asn
                965                 970                 975

Gly Glu Leu Tyr Arg Val Ile Gly Val Asn Asn Asp Leu Leu Asn Arg
            980                 985                 990

Ile Glu Val Asn Met Ile Asp Ile Thr Tyr Arg Glu Tyr Leu Glu Asn
            995                 1000                1005

Met Asn Asp Lys Arg Pro Pro Arg Ile Ile Lys Thr Ile Ala Ser
        1010                1015                1020

Lys Thr Gln Ser Ile Lys Lys Tyr Ser Thr Asp Ile Leu Gly Asn
        1025                1030                1035

Leu Tyr Glu Val Lys Ser Lys Lys His Pro Gln Ile Ile Lys Lys
        1040                1045                1050

Gly

<210> SEQ ID NO 45
<211> LENGTH: 1368
<212> TYPE: PRT
<213> ORGANISM: Artificial sequence
<220> FEATURE:
<223> OTHER INFORMATION: synthetic sequence

<400> SEQUENCE: 45

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190
```

```
Asn Gln Leu Phe Glu Glu Asn Pro Ile Asn Ala Ser Gly Val Asp Ala
        195                 200                 205
Lys Ala Ile Leu Ser Ala Arg Leu Ser Lys Ser Arg Arg Leu Glu Asn
210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
            260                 265                 270
Asp Asp Leu Asp Asn Leu Leu Ala Gln Ile Gly Asp Gln Tyr Ala Asp
        275                 280                 285
Leu Phe Leu Ala Ala Lys Asn Leu Ser Asp Ala Ile Leu Leu Ser Asp
    290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
        355                 360                 365
Gln Glu Glu Phe Tyr Lys Phe Ile Lys Pro Ile Leu Glu Lys Met Asp
    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
        435                 440                 445
Pro Tyr Tyr Val Gly Pro Leu Ala Arg Gly Asn Ser Arg Phe Ala Trp
    450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
        515                 520                 525
Tyr Val Thr Glu Gly Met Arg Lys Pro Ala Phe Leu Ser Gly Glu Gln
    530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
            580                 585                 590
Thr Tyr His Asp Leu Leu Lys Ile Ile Lys Asp Lys Asp Phe Leu Asp
        595                 600                 605
Asn Glu Glu Asn Glu Asp Ile Leu Glu Asp Ile Val Leu Thr Leu Thr
```

```
                610                 615                 620
Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
                835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
                930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
                995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035
```

Tyr Ser Asn Ile Met Asn Phe Phe Lys Thr Glu Ile Thr Leu Ala
1040                1045                1050

Asn Gly Glu Ile Arg Lys Arg Pro Leu Ile Glu Thr Asn Gly Glu
1055                1060                1065

Thr Gly Glu Ile Val Trp Asp Lys Gly Arg Asp Phe Ala Thr Val
1070                1075                1080

Arg Lys Val Leu Ser Met Pro Gln Val Asn Ile Val Lys Lys Thr
1085                1090                1095

Glu Val Gln Thr Gly Gly Phe Ser Lys Glu Ser Ile Leu Pro Lys
1100                1105                1110

Arg Asn Ser Asp Lys Leu Ile Ala Arg Lys Lys Asp Trp Asp Pro
1115                1120                1125

Lys Lys Tyr Gly Gly Phe Asp Ser Pro Thr Val Ala Tyr Ser Val
1130                1135                1140

Leu Val Val Ala Lys Val Glu Lys Gly Lys Ser Lys Lys Leu Lys
1145                1150                1155

Ser Val Lys Glu Leu Leu Gly Ile Thr Ile Met Glu Arg Ser Ser
1160                1165                1170

Phe Glu Lys Asn Pro Ile Asp Phe Leu Glu Ala Lys Gly Tyr Lys
1175                1180                1185

Glu Val Lys Lys Asp Leu Ile Ile Lys Leu Pro Lys Tyr Ser Leu
1190                1195                1200

Phe Glu Leu Glu Asn Gly Arg Lys Arg Met Leu Ala Ser Ala Gly
1205                1210                1215

Glu Leu Gln Lys Gly Asn Glu Leu Ala Leu Pro Ser Lys Tyr Val
1220                1225                1230

Asn Phe Leu Tyr Leu Ala Ser His Tyr Glu Lys Leu Lys Gly Ser
1235                1240                1245

Pro Glu Asp Asn Glu Gln Lys Gln Leu Phe Val Glu Gln His Lys
1250                1255                1260

His Tyr Leu Asp Glu Ile Ile Glu Gln Ile Ser Glu Phe Ser Lys
1265                1270                1275

Arg Val Ile Leu Ala Asp Ala Asn Leu Asp Lys Val Leu Ser Ala
1280                1285                1290

Tyr Asn Lys His Arg Asp Lys Pro Ile Arg Glu Gln Ala Glu Asn
1295                1300                1305

Ile Ile His Leu Phe Thr Leu Thr Asn Leu Gly Ala Pro Ala Ala
1310                1315                1320

Phe Lys Tyr Phe Asp Thr Thr Ile Asp Arg Lys Arg Tyr Thr Ser
1325                1330                1335

Thr Lys Glu Val Leu Asp Ala Thr Leu Ile His Gln Ser Ile Thr
1340                1345                1350

Gly Leu Tyr Glu Thr Arg Ile Asp Leu Ser Gln Leu Gly Gly Asp
1355                1360                1365

<210> SEQ ID NO 46
<211> LENGTH: 513
<212> TYPE: DNA
<213> ORGANISM: Artificial sequence
<220> FEATURE:
<223> OTHER INFORMATION: synthetic sequence

<400> SEQUENCE: 46
atgagaaaga caatagagcg gctgcttaac tctgagcttt cttcaaacag tatcgctgta    60

```
cgaaccggcg taagccaggc agtgatctct aaactgcgca acggaaaaaa agaactgggt    120
aacttgactc tgaacagtgc ggaaaaactg ttcgagtacc agaaagagat ggagaaggtt    180
gatacctgga ttgtgtatcg cgggagaacg gctgatatga acaagtccta tatagctgag    240
ggaagtacat atgaggaagt atataataat tttgtagata aatacggtta tgacgtactt    300
gacgaggaca tatatgagat tcaactcctc aaaaagaatg gcgagaatct tgacgactat    360
gatgtagact ccgacgggat caataattat gataagctgg acgagtttcg ggagagcgac    420
tacgtcgacc tggaagatta cgattacagg gaactctttg agaacagcag cagccaagtg    480
tactatcacg agtttgagat aacccacgag tga                                513

<210> SEQ ID NO 47
<211> LENGTH: 345
<212> TYPE: DNA
<213> ORGANISM: Artificial sequence
<220> FEATURE:
<223> OTHER INFORMATION: synthetic sequence

<400> SEQUENCE: 47
atggagaagg ttgatacctg gattgtgtat cgcgggagaa cggctgatat gaacaagtcc     60
tatatagctg agggaagtac atatgaggaa gtatataata attttgtaga taaatacggt    120
tatgacgtac ttgacgagga catatatgag attcaactcc tcaaaaagaa tggcgagaat    180
cttgacgact atgatgtaga ctccgacggg atcaataatt atgataagct ggacgagttt    240
cgggagagcg actacgtcga cctggaagat tacgattaca gggaactctt tgagaacagc    300
agcagccaag tgtactatca cgagtttgag ataacccacg agtga                   345

<210> SEQ ID NO 48
<211> LENGTH: 480
<212> TYPE: DNA
<213> ORGANISM: Artificial sequence
<220> FEATURE:
<223> OTHER INFORMATION: synthetic sequence

<400> SEQUENCE: 48
ttgaagaaga ccattgaaaa actcttgaac tctgatctca atagcaacta tatcgcaaaa     60
aagactgggg ttgagcaaag tactatttat cgcctgagaa cgggcgagcg ccagcttgga    120
aagctcggcc ttgattctgc tgaacgactt tacaattacc agaaggaaat agaaaacatg    180
aaaagtgtaa agtatatttc taatatgagt aaacaggaga aggggtatcg ggtatatgtt    240
aacgtggtaa atgaggacac ggataaaggc tttcttttcc cctctgtccc aaaggaggtg    300
atagaaaacg ataagatcga cgaacttttc aatttttgaac atcacaaacc ctacgtgcaa    360
aaagcgaaat ccaggtatga caagaatgga atcggtatata aatagttca acttgacgaa    420 ggtttccaaa aatttattga attgaacaaa gagaagatga aggaaaacct tgactattag    480

<210> SEQ ID NO 49
<211> LENGTH: 303
<212> TYPE: DNA
<213> ORGANISM: Artificial sequence
<220> FEATURE:
<223> OTHER INFORMATION: synthetic sequence

<400> SEQUENCE: 49
atgaaaagtg taaagtatat ttctaatatg agtaaacagg agaagggta tcgggtatat     60 gttaacgtgg taaatgagga cacggataaa ggctttcttt tcccctctgt cccaaaggag    120
gtgatagaaa acgataagat cgacgaactt ttcaattttg aacatcacaa accctacgtg    180
```

```
caaaaagcga aatccaggta tgacaagaat ggaatcggat ataaaatagt tcaacttgac    240
gaaggtttcc aaaaatttat tgaattgaac aaagagaaga tgaaggaaaa ccttgactat    300
tag                                                                  303
```

MODULATORS OF CAS9 POLYPEPTIDE ACTIVITY AND METHODS OF USE THEREOF

CROSS-REFERENCE

This application claims the benefit of U.S. Provisional Patent Application No. 62/908,892, filed Oct. 1, 2019, which application is incorporated herein by reference in its entirety.

STATEMENT REGARDING FEDERALLY SPONSORED RESEARCH

This invention was made with government support under Grant No. HR0011-17-2-0043 awarded by the Defense Advanced Research Projects Agency, and Grant No. 1244557 awarded by the National Science Foundation. The government has certain rights in the invention.

INTRODUCTION

Clustered Regularly Interspaced Short Palindromic Repeat (CRISPR)/Cas9 nucleases, when complexed with a guide RNA, effect genome editing in a sequence-specific manner RNA-guided Cas9 has proven to be a versatile tool for genome engineering in multiple cell types and organisms.

There is a need in the art for compositions and methods for controlling genome editing activity of CRISPR/Cas9.

SUMMARY

The present disclosure provides polypeptides that inhibit activity of a CRISPR/Cas effector polypeptide, nucleic acids encoding the polypeptides, and systems comprising the polypeptides and/or nucleic acids encoding the polypeptides. The present disclosure provides methods of inhibiting activity of a CRISRP/Cas effector polypeptide.

BRIEF DESCRIPTION OF THE DRAWINGS

FIG. 5 provides an amino acid sequence of *Staphylococcus aureus* Cas9.

FIG. 6 provides an amino acid sequence of *Streptococcus pyogenes* Cas9.

FIG. 11 provides an amino acid sequence of an Aca cand27 polypeptide.

FIG. 12 provides a human codon-optimized nucleotide sequence encoding an Aca cand27 polypeptide.

FIG. 13 provides an N-terminally truncated Aca cand27 polypeptide.

FIG. 14 provides a human codon-optimized nucleotide sequence encoding an N-terminally truncated Aca cand27 polypeptide.

FIG. 15 provides an amino acid sequence of an Aca cand9 polypeptide.

FIG. 16 provides a human codon-optimized nucleotide sequence encoding an Aca cand9 polypeptide.

FIG. 17 provides an N-terminally truncated Aca cand9 polypeptide.

FIG. 18 provides a human codon-optimized nucleotide sequence encoding an N-terminally truncated Aca cand9 polypeptide.

DEFINITIONS

Figure 1:
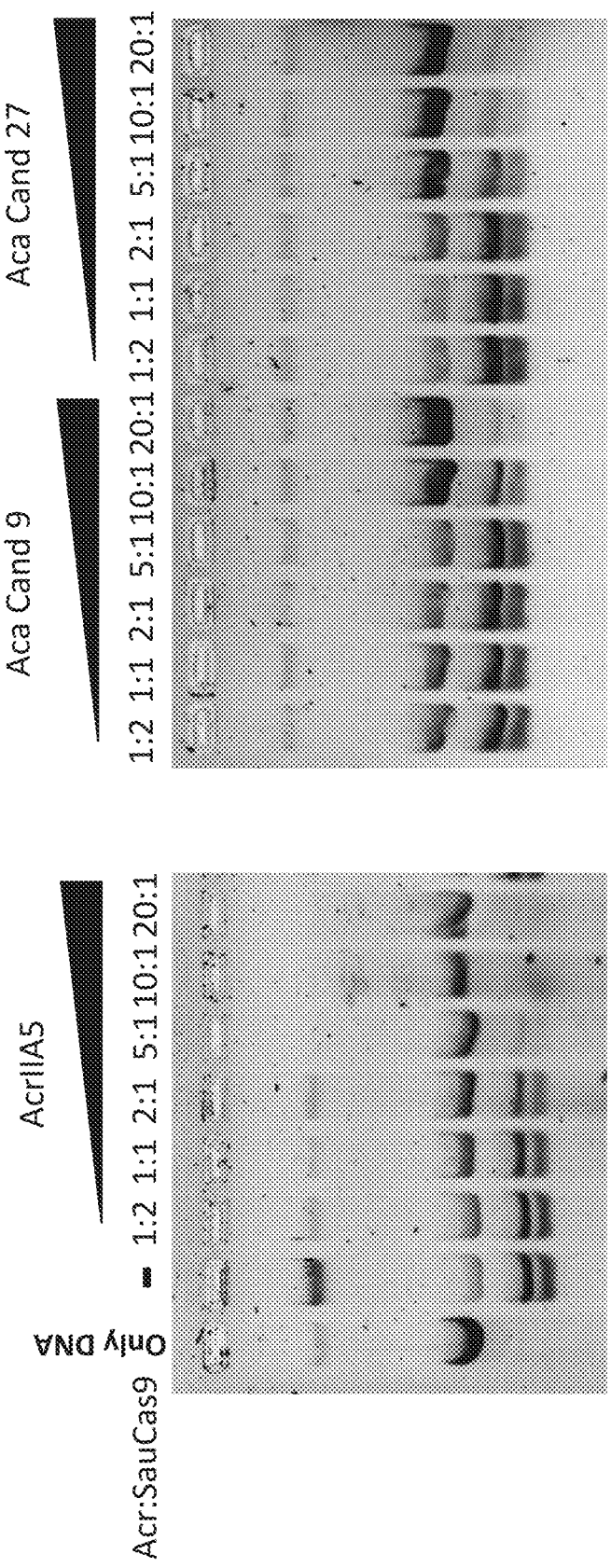
FIG. 1 depicts the effect of anti-CRISPR (Acr) proteins Aca Cand9 and Aca Cand27, compared to the AcrIIA5 anti-CRISPR, on SauCas9/guide RNA-mediated cleavage of a target nucleic acid at various molar ratios of Acr:SauCas9 in vitro.

The terms "polynucleotide" and "nucleic acid," used interchangeably herein, refer to a polymeric form of nucleotides of any length, either ribonucleotides or deoxyribonucleotides. Thus, terms "polynucleotide" and "nucleic acid" encompass single-stranded DNA; double-stranded DNA; multi-stranded DNA; single-stranded RNA; double-stranded RNA; multi-stranded RNA; genomic DNA; cDNA; DNA-RNA hybrids; and a polymer comprising purine and pyrimidine bases or other natural, chemically or biochemically modified, non-natural, or derivatized nucleotide bases.

The term "oligonucleotide" refers to a polynucleotide of between 4 and 100 nucleotides of single- or double-stranded nucleic acid (e.g., DNA, RNA, or a modified nucleic acid). However, for the purposes of this disclosure, there is no upper limit to the length of an oligonucleotide. Oligonucleotides are also known as "oligomers" or "oligos" and can be isolated from genes, transcribed (in vitro and/or in vivo), or chemically synthesized. The terms "polynucleotide" and "nucleic acid" should be understood to include, as applicable to the embodiments being described, single-stranded (such as sense or antisense) and double-stranded polynucleotides.

By "hybridizable" or "complementary" or "substantially complementary" it is meant that a nucleic acid (e.g. RNA, DNA) comprises a sequence of nucleotides that enables it to non-covalently bind, i.e. form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. Standard Watson-Crick base-pairing includes: adenine/adenosine) (A) pairing with thymidine/thymidine (T), A pairing with uracil/uridine (U), and guanine/guanosine (G) pairing with cytosine/cytidine (C). In addition, for hybridization between two RNA molecules (e.g., dsRNA), and for hybridization of a DNA molecule with an RNA molecule (e.g., when a DNA target nucleic acid base pairs with a guide RNA, etc.): G can also base pair with U. For example, G/U base-pairing is partially responsible for the degeneracy (i.e., redundancy) of the genetic code in the context of tRNA anti-codon base-pairing with codons in mRNA. Thus, in the context of this disclosure, a G (e.g., of a protein-binding segment (e.g., dsRNA duplex) of a guide RNA molecule; of a target nucleic acid (e.g., target DNA) base pairing with a guide RNA) is considered complementary to both a U and to C. For example, when a G/U base-pair can be made at a given nucleotide position of a protein-binding segment (e.g., dsRNA duplex) of a guide RNA molecule, the position is not considered to be non-complementary, but is instead considered to be complementary.

Hybridization requires that the two nucleic acids contain complementary sequences, although mismatches between bases are possible. The conditions appropriate for hybridization between two nucleic acids depend on the length of the nucleic acids and the degree of complementarity, variables well known in the art. The greater the degree of complementarity between two nucleotide sequences, the greater the value of the melting temperature (Tm) for hybrids of nucleic acids having those sequences. Typically, the length for a hybridizable nucleic acid is 8 nucleotides or more (e.g., 10 nucleotides or more, 12 nucleotides or more, 15 nucleotides or more, 20 nucleotides or more, 22 nucleotides or more, 25 nucleotides or more, or 30 nucleotides or more).

It is understood that the sequence of a polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure, a 'bulge', and the like). A polynucleotide can comprise 60% or more, 65% or more, 70% or more, 75% or more, 80% or more, 85% or more, 90% or more, 95% or more, 98% or more, 99% or more, 99.5% or more, or 100% sequence complementarity to a target region within the target nucleic acid sequence to which it will hybridize. For example, an antisense nucleic acid in which 18 of 20 nucleotides of the antisense compound are complementary to a target region, and would therefore specifically hybridize, would represent 90 percent complementarity. The remaining noncomplementary nucleotides may be clustered or interspersed with complementary nucleotides and need not be contiguous to each other or to complementary nucleotides. Percent complementarity between particular stretches of nucleic acid sequences within nucleic acids can be determined using any convenient method. Example methods include BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), e.g., using default settings, which uses the algorithm of Smith and Waterman (Adv. Appl. Math., 1981, 2, 482-489).

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

"Binding" as used herein (e.g. with reference to an RNA-binding domain of a polypeptide, binding to a target nucleic acid, and the like) refers to a non-covalent interaction between macromolecules (e.g., between a protein and a nucleic acid; between a guide RNA and a target nucleic acid; and the like). While in a state of non-covalent interaction, the macromolecules are said to be "associated" or "interacting" or "binding" (e.g., when a molecule X is said to interact with a molecule Y, it is meant the molecule X binds to molecule Y in a non-covalent manner). Not all components of a binding interaction need be sequence-specific (e.g., contacts with phosphate residues in a DNA backbone), but some portions of a binding interaction may be sequence-specific. Binding interactions are generally characterized by a dissociation constant ($K_d$) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. "Affinity" refers to the strength of binding, increased binding affinity being correlated with a lower $K_d$.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine-glycine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different ways. To determine sequence identity, sequences can be aligned using various methods and computer programs (e.g., BLAST, T-COFFEE, MUSCLE, MAFFT, Phyre2, etc.), available over the world wide web at sites including ncbi(dot)nlm(dot)nili(dot)gov/BLAST, ebi(dot)ac(dot)uk/Tools/msa/tcoffee/, ebi(dot)ac(dot)uk/Tools/msa/muscle/, mafft.cbrc(dot)jp/alignment/software/, www(dot)sbg(dot)bio(dot)ic(dot)ac(dot)uk/~phyre2/. See, e.g., Altschul et al. (1990), J. Mol. Bioi. 215: 403-10.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate transcription of a non-coding sequence (e.g., guide RNA) or a coding sequence (e.g., protein coding) and/or regulate translation of an encoded polypeptide.

As used herein, a "promoter" is a DNA regulatory region capable of binding RNA polymerase and initiating transcription of a downstream (3' direction) coding or non-coding sequence. Various promoters, including inducible promoters, may be used to drive the various nucleic acids (e.g., vectors) of the present disclosure.

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below). Alternatively, DNA sequences encoding RNA (e.g., guide RNA) that is not translated may also be considered recombinant. Thus, e.g., the term "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a codon encoding the same amino acid, a conservative amino acid, or a non-conservative amino acid. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques. When a recombinant polynucleotide encodes a polypeptide, the sequence of the encoded polypeptide can be naturally occurring ("wild type") or can be a variant (e.g., a mutant) of the naturally occurring sequence. Thus, the term "recombinant" polypeptide does not necessarily refer to a polypeptide whose sequence does not naturally occur. Instead, a "recombinant" polypeptide is encoded by a recombinant DNA sequence, but the sequence of the polypeptide can be naturally occurring ("wild type") or non-naturally occurring (e.g., a variant, a mutant, etc.). Thus, a "recombinant" polypeptide is the result of human intervention, but may be a naturally occurring amino acid sequence.

A "vector" or "expression vector" is a replicon, such as plasmid, phage, virus, or cosmid, to which another DNA segment, i.e. an "insert", may be attached so as to bring about the replication of the attached segment in a cell.

An "expression cassette" comprises a DNA coding sequence operably linked to a promoter. "Operably linked" refers to a juxtaposition wherein the components so described are in a relationship permitting them to function in their intended manner. For instance, a promoter is operably linked to a coding sequence if the promoter affects its transcription or expression.

The terms "recombinant expression vector," or "DNA construct" are used interchangeably herein to refer to a DNA molecule comprising a vector and one insert. Recombinant expression vectors are usually generated for the purpose of expressing and/or propagating the insert(s), or for the construction of other recombinant nucleotide sequences. The insert(s) may or may not be operably linked to a promoter sequence and may or may not be operably linked to DNA regulatory sequences.

Any given component, or combination of components can be unlabeled, or can be detectably labeled with a label moiety. In some cases, when two or more components are labeled, they can be labeled with label moieties that are distinguishable from one another.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an Acr polypeptide" includes a plurality of such polypeptides and reference to "the Cas9 polypeptide" includes reference to one or more Cas9 polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides polypeptides that inhibit activity of a CRISPR/Cas effector polypeptide, nucleic acids encoding the polypeptides, and systems comprising the polypeptides and/or nucleic acids encoding the polypeptides. The present disclosure provides methods of inhibiting activity of a CRISRP/Cas effector polypeptide.

Anti-CRISPR Polypeptides

The present disclosure provides polypeptides that inhibit activity of a CRISPR/Cas effector polypeptide. A polypeptide of the present disclosure that inhibits activity of a CRISPR/Cas effector polypeptide is also referred to herein as an "anti-CRISRP polypeptide" or an "Acr polypeptide."

An Acr polypeptide of the present disclosure can comprise an amino acid sequence having at least 50%, at least 55%, at least 60%, at least 65%, at least 70%, at least 75%, at least 80%, at least 85%, at least 90%, at least 95%, at least 97%, at least 98%, at least 99%, or 100%, amino acid sequence identity to a contiguous stretch of from about 50 amino acids to about 75 amino acids, from about 75 amino acids to about 100 amino acids, from about 100 amino acids to about 125 amino acids, from about 125 amino acids to about 150 amino acids, or from about 150 amino acids to about 159 amino acids, of the following amino acid sequence:

LKKTIEKLLN SDLNSNYIAK KTGVEQSTIY RLRTGERQLG KLGLDSAERL YNYQKEIENM KSVKYISNMS KQEKGYRVYV NVVNEDTDKG FLFPSVPKEV IENDKIDELF NFEHHKPYVQ KAKSRYDKNG IGYKIVQLDE GFQKFIELNK EKMKENLDY (SEQ ID NO:1). The amino acid sequence set forth in SEQ ID NO:1 is also referred to as "Aca cand9" or "AcrIIA-Cand9."

In some cases, an Acr polypeptide of the present disclosure comprises an amino acid sequence having at least 50%, at least 55%, at least 60%, at least 65%, at least 70%, at least 75%, at least 80%, at least 85%, at least 90%, at least 95%, at least 97%, at least 98%, at least 99%, or 100%, amino acid sequence identity to the Aca cand9 amino acid sequence set forth in SEQ ID NO:1. In some cases, the Acr polypeptide has a length of from about 75 amino acids to about 159 amino acids. For example, in some cases, the Acr polypeptide has a length of from about 75 amino acids to about 80 amino acids, from about 80 amino acids to about 90 amino acids, from about 90 amino acids to about 100 amino acids, from about 100 amino acids to about 110 amino acids, from about 110 amino acids to about 120 amino acids, from about 120 amino acids to about 130 amino acids, from about 130 amino acids to about 140 amino acids, from about 140 amino acids to about 150 amino acids, or from about 150 amino acids to about 159 amino acids.

An Acr polypeptide of the present disclosure can comprise an amino acid sequence having at least 50%, at least 55%, at least 60%, at least 65%, at least 70%, at least 75%, at least 80%, at least 85%, at least 90%, at least 95%, at least 97%, at least 98%, at least 99%, or 100%, amino acid sequence identity to a contiguous stretch of from about 50 amino acids to about 75 amino acids, from about 75 amino acids to about 100 amino acids, from about 100 amino acids to about 125 amino acids, from about 125 amino acids to about 150 amino acids, from about 150 amino acids to about 160 amino acids, or from about 160 amino acids to about 170 amino acids, of the following amino acid sequence:

MRKTIERLLN SELSSNSIAV RTGVSQAVIS KLRNGKKELG NLTLNSAEKL FEYQKEMEKV DTWIVYRGRT ADMNKSYIAE GSTYEEVYNN FVDKYGYDVL DEDIYEIQLL KKNGENLDDY DVDSDGINNY DKLDEFRESD YVDLEDYDYR ELFENSSSQV YYHEFEITHE (SEQ ID NO:2). The amino acid sequence set forth in SEQ ID NO:2 is also referred to as "Aca cand27" or "AcrIIA-Cand27."

In some cases, an Acr polypeptide of the present disclosure comprises an amino acid sequence having at least 50%, at least 55%, at least 60%, at least 65%, at least 70%, at least 75%, at least 80%, at least 85%, at least 90%, at least 95%, at least 97%, at least 98%, at least 99%, or 100%, amino acid sequence identity to the Aca cand27 amino acid sequence set forth in SEQ ID NO:2. In some cases, the Acr polypeptide has a length of from about 90 amino acids to about 170 amino acids. For example, in some cases, the Acr polypeptide has a length of from about 90 amino acids to about 95 amino acids, from about 95 amino acids to about 100 amino acids, from about 100 amino acids to about 105 amino acids, from about 105 amino acids to about 110 amino acids, from about 110 amino acids to about 115 amino acids, from about 115 amino acids to about 120 amino acids, from about 120 amino acids to about 130 amino acids, from about 130 amino acids to about 140 amino acids, from about 140 amino acids to about 150 amino acids, from about 150 amino acids to about 160 amino acids, or from about 160 amino acids to about 170 amino acids.

In some cases, an Acr polypeptide of the present disclosure lacks the N-terminal 54 to 64 amino acids (e.g., lacks the N-terminal 54 amino acids, 55 amino acids, 56 amino acids, 57 amino acids, 58 amino acids, 59 amino acids, 60 amino acids, 61 amino acids, 62 amino acids, 63 amino acids, or 64 amino acids) of the Acr amino acid sequence set forth in SEQ ID NO:1. In some cases, an Acr polypeptide of the present disclosure lacks the N-terminal 59 amino acids of the Acr amino acid sequence set forth in SEQ ID NO:1. In some cases, an Acr polypeptide of the present disclosure lacks the following amino acid sequence: LKKTIEKLLN SDLNSNYIAK KTGVEQSTIY RLRTGERQLG KLGLDSAERL YNYQKEIEN (SEQ ID NO:5). In some cases, an Acr polypeptide of the present disclosure comprises an amino acid sequence having at least 50%, at least 55%, at least 60%, at least 65%, at least 70%, at least 75%, at least 80%, at least 85%, at least 90%, or at least 95%, to the amino acid sequence set forth in SEQ ID NO:1; lacks the N-terminal 54 to 64 amino acids of the Acr amino acid sequence set forth in SEQ ID NO:1; and has a length of from about 95 amino acids to about 105 amino acids (e.g., has a length of 95 amino acids, 96 amino acids, 97 amino acids, 98 amino acids, 99 amino acids, 100 amino acids, 101 amino acids, 102 amino acids, 103 amino acids, 104 amino acids, or 105 amino acids). In some cases, an Acr polypeptide of the present disclosure comprises an amino acid sequence having at least 50%, at least 55%, at least 60%, at least 65%, at least 70%, at least 75%, at least 80%, at least 85%, at least 90%, or at least 95%, to the amino acid sequence set forth in SEQ ID NO:1; lacks the N-terminal 59 amino acids of the Acr amino acid sequence set forth in SEQ ID NO:1; and has a length of 100 amino acids.

In some cases, an Acr polypeptide of the present disclosure comprises an amino acid sequence having at least 50%, at least 55%, at least 60%, at least 65%, at least 70%, at least 75%, at least 80%, at least 85%, at least 90%, at least 95%, at least 97%, at least 98%, at least 99%, or 100%, amino acid sequence identity to the following amino acid sequence:

M KSVKYISNMS KQEKGYRVYV NVVNEDTDKG FLFPSVPKEV IENDKIDELF NFEHHKPYVQ KAKSRYDKNG IGYKIVQLDE GFQKFIELNK EKMKENLDY (SEQ ID NO:3); and has a length of from about 95 amino acids to about 105 amino acids (e.g., has a length of 95 amino acids, 96 amino acids, 97 amino acids, 98 amino acids, 99 amino acids, 100 amino acids, 101 amino acids, 102 amino acids, 103 amino acids, 104 amino acids, or 105 amino acids). In some cases, an Acr polypeptide of the present disclosure comprises an amino acid sequence having at least 50%, at least 55%, at least 60%, at least 65%, at least 70%, at least 75%, at least 80%, at least 85%, at least 90%, at least 95%, at least 97%, at least 98%, at least 99%, or 100%, amino acid sequence identity to the amino acid sequence set forth in SEQ ID NO:3; and has a length of 100 amino acids. An Acr having the amino acid sequence set forth in SEQ ID NO:3 is also referred to herein as "truncated Aca cand9" or "Aca cand9 N trunc" or "AcrIIA-Cand9-trunc."

In some cases, an Acr polypeptide of the present disclosure lacks the N-terminal 51 to 61 amino acids (e.g., lacks the N-terminal 51 amino acids, 52 amino acids, 53 amino acids, 54 amino acids, 55 amino acids, 56 amino acids, 57 amino acids, 58 amino acids, 59 amino acids, 60 amino acids, or 61 amino acids) of the Acr amino acid sequence set forth in SEQ ID NO:2. In some cases, an Acr polypeptide of the present disclosure lacks the N-terminal 56 amino acids of the Acr amino acid sequence set forth in SEQ ID NO:2. In some cases, an Acr polypeptide of the present disclosure lacks the following amino acid sequence: MRKTIERLLN SELSSNSIAV RTGVSQAVIS KLRNGKKELG NLTLN-SAEKL FEYQKE (SEQ ID NO:6). In some cases, an Acr polypeptide of the present disclosure comprises an amino acid sequence having at least 50%, at least 55%, at least 60%, at least 65%, at least 70%, at least 75%, at least 80%, at least 85%, at least 90%, or at least 95%, to the amino acid sequence set forth in SEQ ID NO:2; lacks the N-terminal 51 to 61 amino acids of the Acr amino acid sequence set forth in SEQ ID NO:2; and has a length of from about 109 amino acids to about 119 amino acids (e.g., has a length of 109 amino acids, 110 amino acids, 111 amino acids, 112 amino acids, 113 amino acids, 114 amino acids, 115 amino acids, 116 amino acids, 117 amino acids, 118 amino acids, or 119 amino acids). In some cases, an Acr polypeptide of the present disclosure comprises an amino acid sequence having at least 50%, at least 55%, at least 60%, at least 65%, at least 70%, at least 75%, at least 80%, at least 85%, at least 90%, or at least 95%, to the amino acid sequence set forth in SEQ ID NO:2; lacks the N-terminal 56 amino acids of the Acr amino acid sequence set forth in SEQ ID NO:2; and has a length of 114 amino acids.

In some cases, an Acr polypeptide of the present disclosure comprises an amino acid sequence having at least 50%, at least 55%, at least 60%, at least 65%, at least 70%, at least 75%, at least 80%, at least 85%, at least 90%, at least 95%, at least 97%, at least 98%, at least 99%, or 100%, amino acid sequence identity to the following amino acid sequence:

MEKVDTWIVYRGRTADMNKSYIAEGSTY-EEVYNNFVDKYGYDVLDEDIYEIQLLKKNG ENLD-DYDVDSDGINNYDKLDEFRESDYVDLEDYDYRELF-ENSSSQVYYHEFEITHE (SEQ ID NO:4); and has a length of from about 109 amino acids to about 119 amino acids (e.g., has a length of 109 amino acids, 110 amino acids, 111 amino acids, 112 amino acids, 113 amino acids, 114 amino acids, 115 amino acids, 116 amino acids, 117 amino acids, 118 amino acids, or 119 amino acids). In some cases, an Acr polypeptide of the present disclosure comprises an amino acid sequence having at least 50%, at least 55%, at least 60%, at least 65%, at least 70%, at least 75%, at least 80%, at least 85%, at least 90%, at least 95%, at least 97%, at least 98%, at least 99%, or 100%, amino acid sequence identity to SEQ ID NO:4; and has a length of 114 amino acids. An Acr having the amino acid sequence set forth in SEQ ID NO:4 is also referred to herein as "truncated Aca cand27" or "Aca cand27 N trunc" or "AcrIIA-Cand27-trunc."

In some cases, an Acr polypeptide of the present disclosure inhibits binding and/or cleavage activity of a Cas9 polypeptide in a Cas9/guide RNA complex by at least 50%, at least 60%, at least 70%, at least 80%, at least 85%, at least 90%, at least 95%, at least 98%, or at least 99%, compared to the binding and/or cleavage activity of the Cas9 polypeptide in a Cas9/guide RNA complex in the absence of the Acr polypeptide (i.e., where the Cas9 polypeptide in a Cas9/guide RNA complex is not contacted with the Acr polypeptide).

In some cases, an Acr polypeptide of the present disclosure inhibits binding and/or cleavage activity of a Cas9/guide RNA complex by at least 50%, at least 60%, at least 70%, at least 80%, at least 85%, at least 90%, at least 95%, at least 98%, or at least 99%, compared to the binding and/or cleavage activity of the Cas9/guide RNA complex in the absence of the Acr polypeptide (i.e., where the Cas9/guide RNA complex is not contacted with the Acr polypeptide).

In some cases, an Acr polypeptide of the present disclosure inhibits cleavage activity of a Cas9 polypeptide present in a Cas9/guide RNA complex by at least 50%, at least 60%, at least 70%, at least 80%, at least 85%, at least 90%, at least 95%, at least 98%, or at least 99%, compared to the cleavage activity of the Cas9 polypeptide in a Cas9/guide RNA complex in the absence of the Acr polypeptide, when the molar ratio of Acr to Cas9 polypeptide is at least 2:1, at least 5:1, or at least 10:1. In some cases, an Acr polypeptide of the present disclosure inhibits cleavage activity of a Cas9 polypeptide present in a Cas9/guide RNA complex by at least 50%, at least 60%, at least 70%, at least 80%, at least 85%, at least 90%, at least 95%, at least 98%, or at least 99%, compared to the cleavage activity of the Cas9 polypeptide in a Cas9/guide RNA complex in the absence of the Acr polypeptide, when the molar ratio of Acr to Cas9 polypeptide is from about 2:1 to about 5:1, from about 5:1 to about 10:1, from about 10:1 to about 20:1, or from about 20:1 to about 40:1.

"Binding" activity of a Cas9/guide RNA complex refers to binding of the Cas9/guide RNA complex to a target nucleic acid, where the target nucleic acid comprises a nucleotide sequence that has complementarity to a target-binding nucleotide sequence in the guide RNA.

"Cleavage" activity of a Cas9/guide RNA complex refers to generation by the Cas9/guide RNA complex of a single-strand or double-strand break in a target nucleic acid.

In some cases, an Acr polypeptide of the present disclosure inhibits binding and/or cleavage activity of a Cas9 polypeptide in a Cas9/guide RNA complex having at least 50%, at least 60%, at least 70%, at least 80%, at least 85%, at least 90%, at least 95%, at least 98%, at least 99%, or 100%, amino acid sequence identity to the *Staphylococcus aureus* Cas9 ("SauCas9") amino acid sequence provided in FIG. 5.

In some cases, an Acr polypeptide of the present disclosure does not substantially inhibit binding and/or cleavage activity of *Streptococcus pyogenes* Cas9 in a Cas9/guide RNA complex. For example, in some cases, an Acr polypeptide of the present disclosure does not substantially inhibit cleavage activity of a Cas9/guide RNA complex, where the Cas9 present in the Cas9/guide RNA complex comprises an amino acid sequence having at least 80%, at least 85%, at least 90%, at least 95%, at least 98%, at least 99%, or 100%, amino acid sequence identity to the *Streptococcus pyogenes* Cas9 amino acid sequence provided in FIG. 6. In some cases, an Acr polypeptide of the present disclosure inhibits cleavage activity of a Cas9/guide RNA complex by no more than 20%, no more than 15%, no more than 10%, no more than 5%, no more than 2%, or no more than 1%, compared to the cleavage activity of the Cas9/guide RNA complex in the absence of the Acr polypeptide, where the Cas9 present in the Cas9/guide RNA complex comprises an amino acid sequence having at least 80%, at least 85%, at least 90%, at least 95%, at least 98%, at least 99%, or 100%, amino acid sequence identity to the *Streptococcus pyogenes* Cas9 amino acid sequence provided in FIG. 6. In some cases, an Acr polypeptide of the present disclosure inhibits cleavage activity of a Cas9/guide RNA complex by less than 20%, less than 15%, less than 10%, less than 5%, less than 2%, or less than 1%, compared to the cleavage activity of the Cas9/guide RNA complex in the absence of the Acr polypeptide, where the Cas9 present in the Cas9/guide RNA complex comprises an amino acid sequence having at least 80%, at least 85%, at least 90%, at least 95%, at least 98%, at least 99%, or 100%, amino acid sequence identity to the *Streptococcus pyogenes* Cas9 amino acid sequence provided in FIG. 6.

Whether an Acr polypeptide inhibits binding activity of a given Cas9/guide RNA complex can be readily determined. For example, a double stranded "Cas9 beacon" DNA fragment comprising a target can be constructed in which the target strand comprises a fluorophore and the non-target strand comprises a fluorescence quencher. Upon binding of the beacon by a Cas9/guide RNA complex, the non-target strand is displaced, allowing unquenched fluorescence from the target strand. Measurement of increased fluorescence signal in the presence of a Cas9/guide RNA complex indicates DNA binding activity of the Cas9/guide RNA complex (Mekler et al. (2016) *Nuc. Acids Res.* 44(6):2837-2845).

Whether an Acr polypeptide inhibits cleavage activity of a given Cas9 polypeptide present in a Cas9/guide RNA complex can be readily determined. For example, the effect of an Acr polypeptide of the present disclosure on cleavage of a target DNA by a Cas9/guide RNA complex can be tested in a cell-free system in vitro, as described in the Examples section. For example, a target DNA is mixed in vitro with: a) a complex of Cas9 and a guide RNA, where the guide RNA comprises both a nucleotide sequence (tracrRNA) that activates the Cas9 polypeptide and a nucleotide sequence (crRNA) that binds to the target DNA; and b) an Acr polypeptide. Production of cleavage products of action of the Cas9 on the target DNA can be detected by resolving the cleavage products on a 1% agarose cell and staining the resolved cleavage products.

As another example, the effect of an Acr polypeptide of the present disclosure on cleavage of a target DNA by a Cas9/guide RNA complex can be tested in a cell. For example, a nucleic acid comprising a nucleotide sequence encoding an Acr polypeptide and a nucleic acid comprising a nucleotide sequence encoding a reporter (e.g., a fluorescent protein such as a green fluorescent protein) can be integrated into the genome of a mammalian cell (e.g., 293 cells, or other mammalian cell line), generating a reporter cell; and a ribonucleoprotein (RNP) complex comprising a Cas9 polypeptide and a guide RNA targeting the nucleotide sequence encoding the reporter is introduced into the reporter cell. Inhibition of gene editing of the reporter can be determined by detecting the reporter. For example, where the reporter is a fluorescent protein, fluorescence activated cell sorting (FACS) can be used to determine whether gene editing has been inhibited. As another example, a mixture of a Cas9/guide RNA complex and Acr polypeptide can be introduced into a mammalian cell line, and the effect of the Acr polypeptide on the ability of the Cas9/guide RNA complex to carry out gene editing can be determined by analyzing production of a gene product encoded by a nucleotide sequence targeted by the guide RNA.

Covalently Linked Non-Peptidic Moiety

In some cases, an Acr polypeptide of the present disclosure comprises a non-peptidic moiety covalently linked to the Acr polypeptide. The covalently linked non-peptidic moiety can confer a desirable attribute (e.g., increased protease resistance, increased membrane permeability, increased cell type or tissue specific targeting, increased in vivo half-life, increased in vivo stability, increased bioavailability), without substantially altering the ability of the linked Acr polypeptide to inhibit Cas9 activity.

In some cases, the non-peptidic moiety confers increased in vivo half-life on the linked Acr polypeptide, compared to the in vivo half-life of the Acr not comprising the non-peptidic moiety. For example, in some cases, the in vivo half-life of an Acr polypeptide comprising a covalently linked non-peptidic moiety is at least 10%, at least 25%, at least 50%, at least 2-fold, at least 5-fold, or at least 10-fold, greater than the in vivo half-life of the Acr polypeptide not comprising the non-peptidic moiety. For example, in some cases, the non-peptidic moiety confers an increase in half-life of the linked Acr polypeptide in circulation in an animal In some cases, the non-peptidic moiety confers increased in vivo stability on the linked Acr polypeptide, compared to the in vivo stability of the Acr polypeptide not comprising the non-peptidic moiety. For example, in some cases, the in vivo stability of an Acr polypeptide comprising a covalently linked non-peptidic moiety is at least 10%, at least 25%, at least 50%, at least 2-fold, at least 5-fold, or at least 10-fold, greater than the in vivo stability of the Acr polypeptide not comprising the non-peptidic moiety. In some cases, the non-peptidic moiety confers increased bioavailability on the linked Acr polypeptide, compared to the bioavailability of the Acr polypeptide not comprising the non-peptidic moiety. For example, in some cases, the bioavailability of an Acr polypeptide comprising a covalently linked non-peptidic moiety is at least 10%, at least 25%, at least 50%, at least 2-fold, at least 5-fold, or at least 10-fold, greater than the bioavailability of the Acr polypeptide not comprising the non-peptidic moiety.

Suitable non-peptidic moieties include, but are not limited to, lipids and non-peptidic polymers. Suitable non-peptidic moieties include, but are not limited to, poly(ethylene glycol), polysialic acid, hydroxyethyl starch (HES), a dendrimer, a nanoparticle, and a liposome.

In some cases, a non-peptidic moiety covalently linked to an Acr polypeptide of the present disclosure is a polymer. Polymers may contain one more of the following polyesters: homopolymers including glycolic acid units, referred to herein as "PGA"; lactic acid units, such as poly-L-lactic acid, poly-D-lactic acid, poly-D,L-lactic acid, poly-L-lactide, poly-D-lactide, and poly-D,L-lactide, collectively referred to herein as "PLA"; caprolactone units, such as poly(caprolactone), collectively referred to herein as "PCL"; copolymers including lactic acid and glycolic acid units, such as various forms of poly(lactic acid-co-glycolic acid) and poly(lactide-co-glycolide) characterized by the ratio of lactic acid:glycolic acid, collectively referred to herein as "PLGA"; and polyacrylates, and derivatives thereof. Exemplary polymers also include copolymers of polyethylene glycol (PEG) and the aforementioned polyesters, such as various forms of PLGA-PEG or PLA-PEG copolymers, collectively referred to herein as "PEGylated polymers". In certain cases, the PEG region can be covalently associated with polymer to yield "PEGylated polymers" by a cleavable linker.

An Acr polypeptide of the present disclosure may include one or more covalently linked hydrophilic polymers. Hydrophilic polymers include cellulosic polymers such as starch and polysaccharides; hydrophilic polypeptides; poly(amino acids) such as poly-L-glutamic acid (PGS), gamma-polyglutamic acid, poly-L-aspartic acid, poly-L-serine, or poly-L-lysine; polyalkylene glycols and polyalkylene oxides such as polyethylene glycol (PEG), polypropylene glycol (PPG), and poly(ethylene oxide) (PEO); poly(oxyethylated polyol); poly(olefinic alcohol); polyvinylpyrrolidone); poly(hydroxyalkylmethacrylamide); poly(hydroxyalkylmethacrylate); poly(saccharides); poly(hydroxy acids); poly(vinyl alcohol); polyoxazoline; and copolymers thereof.

An Acr polypeptide of the present disclosure may include one or more covalently linked hydrophobic polymers. Examples of suitable hydrophobic polymers include polyhydroxyacids such as poly(lactic acid), poly(glycolic acid), and poly(lactic acid-co-glycolic acids); polyhydroxyalkanoates such as poly3-hydroxybutyrate or poly4-hydroxybutyrate; polycaprolactones; poly(orthoesters); polyanhydrides; poly(phosphazenes); poly(lactide-co-caprolactones); polycarbonates such as tyrosine polycarbonates; polyamides (including synthetic and natural polyamides), polypeptides, and poly(amino acids); polyesteramides; polyesters; poly (dioxanones); poly(alkylene alkylates); hydrophobic polyethers; polyurethanes; polyetheresters; polyacetals; polycyanoacrylates; polyacrylates; polymethylmethacrylates; polysiloxanes; poly(oxyethylene)/poly(oxypropylene) copolymers; polyketals; polyphosphates; polyhydroxyvalerates; polyalkylene oxalates; polyalkylene succinates; poly (maleic acids), as well as copolymers thereof.

An Acr polypeptide of the present disclosure may include one or more covalently linked biodegradable polymers. Suitable biodegradable polymers can include polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose such as methyl cellulose and ethyl cellulose, hydroxyalkyl celluloses such as hydroxypropyl cellulose, hydroxy-propyl methyl cellulose, and hydroxybutyl methyl cellulose, cellulose ethers, cellulose esters, nitro celluloses, cellulose acetate, cellulose propionate, cellulose acetate butyrate, cellulose acetate phthalate, carboxylethyl cellulose, cellulose triacetate, cellulose sulphate sodium salt, polymers of acrylic and methacrylic esters such as poly (methyl methacrylate), poly (ethylmethacrylate), poly(butylmethacrylate), poly (isobutylmethacrylate), poly(hexlmethacrylate), poly(isodecylmethacrylate), poly(lauryl methacrylate), poly (phenyl methacrylate), poly(methyl acrylate), poly(isopropyl acrylate), poly(isobutyl acrylate), poly(octadecyl acrylate), polyethylene, polypropylene poly(ethylene glycol), poly(ethylene oxide), poly(ethylene terephthalate), poly(vinyl alcohols), poly(vinyl acetate, poly vinyl chloride polystyrene and polyvinylpryrrolidone, derivatives thereof, linear and branched copolymers and block copolymers thereof, and blends thereof. Exemplary biodegradable polymers include polyesters, poly(ortho esters), poly(ethylene imines), poly(caprolactones), poly(hydroxyalkanoates), poly (hydroxyvalerates), polyanhydrides, poly(acrylic acids), polyglycolides, poly(urethanes), polycarbonates, polyphosphate esters, polyphosphazenes, derivatives thereof, linear and branched copolymers and block copolymers thereof, and blends thereof. In some embodiments the particle contains biodegradable polyesters or polyanhydrides such as poly(lactic acid), poly(glycolic acid), and poly(lactic-co-glycolic acid).

Fusion Polypeptides

In some cases, an Acr polypeptide of the present disclosure is a fusion Acr polypeptide. The present disclosure provides a fusion polypeptide (an "Acr fusion polypeptide") comprising: a) an Acr polypeptide of the present disclosure; and b) a heterologous fusion partner (i.e., one or more heterologous fusion partners). The heterologous fusion partner can provide one or more desirable attributes (where such attributes include, e.g., as increased protease resistance, increased membrane permeability, or increased half-life, increased nuclear localization, increased cell or tissue specific targeting and the like) without substantially altering the ability of the linked Acr polypeptide to inhibit Cas9 activity. A fusion polypeptide comprising: a) an Acr polypeptide of the present disclosure; and b) a heterologous fusion partner is also referred to herein as an "Acr fusion polypeptide." A fusion polypeptide of the present disclosure can comprise two or more heterologous fusion partners.

Suitable heterologous fusion partners include, but are not limited to, a nuclear localization signal; a chloroplast transit peptide; an endosomal escape peptide; an epitope tag; a polypeptide that provides for ease of purification; a detectable protein; a protein that provides for increased in vivo half-life; a protein that provides for increased cell type or tissue specificity (e.g. an antibody or fragment thereof) and the like.

Suitable heterologous fusion partners include a hydroxine-binding protein, transthyretin, α1-acid glycoprotein (AAG), transferrin, fibrinogen, albumin, an immunoglobulin, α-2-macroglobulin, a lipoprotein, and a fragment of any of the foregoing. Suitable heterologous fusion partners include a fluorescent protein, e.g., a green fluorescent protein (GFP), a yellow fluorescent protein, a red fluorescent protein a cyan fluorescent protein, and the like. Suitable heterologous fusion partners include, e.g., a poly(histidine) tag (e.g., a 6×His tag); a hemagglutinin (HA) tag; a FLAG tag; a Myc tag; and the like.

In some cases, a fusion polypeptide of the present disclosure comprises an Acr polypeptide fused to a nuclear localization signal (NLS) (e.g., in some cases 2 or more, 3 or more, 4 or more, or 5 or more NLSs). Thus, in some cases, a fusion Acr polypeptide includes one or more NLSs (e.g., 2 or more, 3 or more, 4 or more, or 5 or more NLSs). In some cases, one or more NLSs (2 or more, 3 or more, 4 or more, or 5 or more NLSs) are positioned at or near (e.g., within 50 amino acids of) the N-terminus and/or the C-terminus of the Acr polypeptide. In some cases, one or more NLSs (2 or more, 3 or more, 4 or more, or 5 or more NLSs) are positioned at or near (e.g., within 50 amino acids of) the N-terminus of the Acr polypeptide. In some cases, one or more NLSs (2 or more, 3 or more, 4 or more, or 5 or more NLSs) are positioned at or near (e.g., within 50 amino acids of) the C-terminus of the Acr polypeptide. In some cases, one or more NLSs (3 or more, 4 or more, or 5 or more NLSs) are positioned at or near (e.g., within 50 amino acids of) both the N-terminus and the C-terminus of the Acr polypeptide. In some cases, an NLS is positioned at the N-terminus and an NLS is positioned at the C-terminus of the Acr polypeptide.

Non-limiting examples of NLSs include an NLS sequence derived from: the NLS of the SV40 virus large T-antigen, having the amino acid sequence PKKKRKV (SEQ ID NO:7); the NLS from nucleoplasmin (e.g., the nucleoplasmin bipartite NLS with the sequence KRPAATKK-AGQAKKKK (SEQ ID NO:8)); the c-myc NLS having the amino acid sequence PAAKRVKLD (SEQ ID NO:9) or RQRRNELKRSP (SEQ ID NO:10); the hRNPA1 M9 NLS having the sequence NQSSNFGPMKGGNFG-GRSSGPYGGGGQYFAKPRNQGGY (SEQ ID NO:11); the sequence RMRIZFKNKGKDTAELRRRRVEVS-VELRKAKKDEQILKRRNV (SEQ ID NO:12) of the IBB domain from importin-alpha; the sequences VSRKRPRP (SEQ ID NO:13) and PPKKARED (SEQ ID NO:14) of the myoma T protein; the sequence PQPKKKPL (SEQ ID NO:15) of human p53; the sequence SALIKKKKKMAP (SEQ ID NO:16) of mouse c-abl IV; the sequences DRLRR (SEQ ID NO:17) and PKQKKRK (SEQ ID NO:18) of the influenza virus NS1; the sequence RKLKKKIKKL (SEQ ID NO:19) of the Hepatitis virus delta antigen; the sequence REKKKFLKRR (SEQ ID NO:20) of the mouse Mx1 protein; the sequence KRKGDEVDGVDEVAKKKSKK (SEQ ID NO:21) of the human poly(ADP-ribose) polymerase; and the sequence RKCLQAGMNLEARKTKK (SEQ ID NO:22) of the steroid hormone receptors (human) glucocorticoid.

An Acr fusion polypeptide of the present disclosure can include, as the fusion partner, a "Protein Transduction Domain" or PTD (also known as a CPP—cell penetrating peptide). Examples of PTDs include but are not limited to a minimal undecapeptide protein transduction domain (corresponding to residues 47-57 of HIV-1 TAT comprising YGRKKRRQRRR; SEQ ID NO:23); a polyarginine sequence comprising a number of arginines sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); an Drosophila Antennapedia protein transduction domain (Noguchi et al. (2003) Diabetes 52(7):1732-1737); a truncated human calcitonin peptide (Trehin et al. (2004) Pharm. Research 21:1248-1256); polylysine (Wender et al. (2000) Proc. Natl. Acad. Sci. USA 97:13003-13008); RRQRRTSKLMKR (SEQ ID NO:24); Transportan GWTLNSAGYLLGKINLKALAALAKKIL (SEQ ID NO:25); KALAWEAKLAKALAKA-LAKHLAKALAKALKCEA (SEQ ID NO:26); and RQIKIWFQNRRMKWKK (SEQ ID NO:27). Exemplary PTDs include but are not limited to, YGRKKRRQRRR (SEQ ID NO:23), RKKRRQRRR (SEQ ID NO:28); an arginine homopolymer of from 3 arginine residues to 50 arginine residues; Exemplary PTD domain amino acid sequences include, but are not limited to, any of the following: YGRKKRRQRRR (SEQ ID NO:23); RKKRRQRR (SEQ ID NO:29); YARAAARQARA (SEQ ID NO:30); THRLPRRRRRR (SEQ ID NO:31); and GGRRARRRRRR (SEQ ID NO:32). In some embodiments, the PTD is an activatable CPP (ACPP) (Aguilera et al. (2009) Integr Biol (Camb) June; 1(5-6): 371-381).

In some cases, an Acr fusion polypeptide of the present disclosure comprises a linker between the Acr polypeptide and the fusion partner. Suitable linkers include polypeptides of between 4 amino acids and 40 amino acids in length, or between 4 amino acids and 25 amino acids in length. These linkers can be produced by using synthetic, linker-encoding oligonucleotides to couple the proteins, or can be encoded by a nucleic acid sequence encoding the fusion protein. Peptide linkers with a degree of flexibility can be used. The linking peptides may have virtually any amino acid sequence, bearing in mind that the preferred linkers will have a sequence that results in a generally flexible peptide. The use of small amino acids, such as glycine and alanine, are of use in creating a flexible peptide. The creation of such sequences is routine to those of skill in the art. A variety of different linkers are commercially available and are considered suitable for use. In some cases, the linker is proteolytically cleavable.

Examples of linker polypeptides include glycine polymers $(G)_n$, glycine-serine polymers (including, for example, $(GS)_n$, $GSGGS_n$ (SEQ ID NO:33), $GGSGGS_n$ (SEQ ID NO:34), and $GGGGS_n$ (SEQ ID NO:35), where n is an integer of at least one), glycine-alanine polymers, alanine-serine polymers. Exemplary linkers can comprise amino acid sequences including, but not limited to, GGSG (SEQ ID NO:36), GGSGG (SEQ ID NO:37), GSGSG (SEQ ID NO:38), GSGGG (SEQ ID NO:39), GGGSG (SEQ ID NO:40), GSSSG (SEQ ID NO:41), and the like.

An Acr fusion polypeptide of the present disclosure can also comprise a covalently linked non-peptidic moiety, where suitable non-peptidic moieties are discussed above.

Nucleic Acids and Recombinant Expression Vectors

The present disclosure provides a nucleic acid comprising a nucleotide sequence encoding an Acr polypeptide of the present disclosure. The present disclosure provides a recombinant expression vector comprising a nucleic acid comprising a nucleotide sequence encoding an Acr polypeptide of the present disclosure. As noted above, in some cases, an Acr polypeptide of the present disclosure is a fusion polypeptide. The present disclosure provides a nucleic acid comprising a nucleotide sequence encoding an Acr fusion polypeptide of the present disclosure. The present disclosure provides a recombinant expression vector comprising a nucleic acid comprising a nucleotide sequence encoding an Acr fusion polypeptide of the present disclosure.

The present disclosure provides a nucleic acid comprising a nucleotide sequence encoding an Acr polypeptide of the present disclosure. In some cases, the nucleic acid is RNA. In some cases, the nucleic acid is DNA. The present disclosure provides a nucleic acid comprising a nucleotide sequence encoding an Acr fusion polypeptide of the present disclosure. In some cases, the nucleic acid is RNA. In some cases, the nucleic acid is DNA.

In some cases, a nucleotide sequence encoding an Acr polypeptide of the present disclosure is codon optimized. This type of optimization can entail a mutation of an Acr-encoding nucleotide sequence to mimic the codon preferences of the intended host organism or cell while encoding the same protein. Thus, the codons can be changed, but the encoded protein remains unchanged. For example, if the intended target cell was a human cell, a human codon-optimized Acr-encoding nucleotide sequence could be used. As another non-limiting example, if the intended host cell were a mouse cell, then a mouse codon-optimized Acr-encoding nucleotide sequence could be generated. As another non-limiting example, if the intended host cell were a plant cell, then a plant codon-optimized Acr-encoding nucleotide sequence could be generated. As another non-limiting example, if the intended host cell were an insect cell, then an insect codon-optimized Acr-encoding nucleotide sequence could be generated.

A non-limiting example of a human codon-optimized nucleotide sequence encoding Aca cand27 is provided in FIG. 12. A non-limiting example of a human codon-optimized nucleotide sequence encoding Aca cand27-trunc is provided in FIG. 14. A non-limiting example of a human codon-optimized nucleotide sequence encoding Aca cand9 is provided in FIG. 16. A non-limiting example of a human codon-optimized nucleotide sequence encoding Aca cand9-trunc is provided in FIG. 18.

In some cases, the nucleotide sequence encoding an Acr polypeptide of the present disclosure, or encoding an Acr fusion polypeptide of the present disclosure, is operably linked to one or more of a promoter, an enhancer, an internal ribosomal entry site, and a transcription termination signal.

In some cases, the nucleotide sequence encoding an Acr polypeptide of the present disclosure, or encoding an Acr fusion polypeptide of the present disclosure, is operably linked to a transcriptional control element. In some cases, the transcriptional control element is a transcriptional control element that is functional in a eukaryotic cell.

The transcriptional control element can be a promoter. In some cases, the promoter is a constitutively active promoter. In some cases, the promoter is a regulatable promoter. In some cases, the promoter is an inducible promoter. In some cases, the promoter is a tissue-specific promoter. In some cases, the promoter is a cell type-specific promoter. In some cases, the transcriptional control element (e.g., the promoter) is functional in a targeted cell type or targeted cell population. For example, in some cases, the transcriptional control element can be functional in a T cell, a B cell, a hematopoietic stem cell, a liver cell, a lung cell, a muscle cell (e.g., a cardiac muscle cell; a skeletal muscle cell), a retinal cell, or other targeted cell.

A suitable promoter can be a constitutively active promoter (i.e., a promoter that is constitutively in an active/"ON" state). A suitable promoter may be an inducible promoter (i.e., a promoter whose state, active/"ON" or inactive/"OFF", is controlled by an external stimulus, e.g., the presence of a particular temperature, compound, or protein). A suitable promoter can be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a Rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like.

Inducible promoters suitable for use include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some cases, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used as long as the promoter is functional in the targeted host cell (e.g., eukaryotic cell).

In some cases, the promoter is a reversible promoter. Suitable reversible promoters, including reversible inducible promoters are known in the art. Such reversible promoters may be isolated and derived from any of a variety of organisms. Modification of reversible promoters derived from a first organism for use in a second (different) organism is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like. A suitable promoter can include elements that are responsive to transactivation, e.g., hypoxia response elements, Gal4 response elements, lac repressor response element, and small molecule control systems such as tetracycline-regulated systems and the RU-486 system (see, e.g., Gossen & Bujard, 1992, Proc. Natl. Acad. Sci. USA, 89:5547; Oligino et al., 1998, Gene Ther., 5:491-496; Wang et al., 1997, Gene Ther., 4:432-441; Neering et al., 1996, Blood, 88:1147-55; and Rendahl et al., 1998, Nat. Biotechnol., 16:757-761).

For illustration purposes, examples of spatially restricted promoters include, but are not limited to, neuron-specific promoters, adipocyte-specific promoters, cardiomyocyte-specific promoters, smooth muscle-specific promoters, photoreceptor-specific promoters, etc. In some cases, the promoter is an insect-specific promoter. In some cases, the promoter is a plant-specific promoter. In some cases, the promoter is a protozoan-specific promoter.

In some cases, the promoter is a plant-specific promoter. Examples of plant promoters include, but are not limited to, a cauliflower mosaic virus (CaMV) promoter, a nopaline synthetase promoter, a ribose bisphosphate carboxylase promoter, a ubiquitin promoter, a UBQ3 promoter, a cestrum virus promoter, a rice actin 1 promoter, a CaMV 35S promoter, a CaMV 19S promoter, a sucrose synthase promoter, and a figwort mosaic virus promoter. Chemical agent-inducible promoters are known in the art and include, but are not limited to, the maize In2-2 promoter, which is activated by benzenesulfonamide herbicide safeners; the maize GST promoter, which is activated by hydrophobic electrophilic compounds that are used as pre-emergent herbicides; and the tobacco PR-1apromoter, which is activated by salicylic acid. Other chemical-regulated promoters of interest include steroid-responsive promoters (see, for example, the glucocorticoid-inducible promoter in Schena, et al., (1991) *Proc. Natl. Acad. Sci. USA* 88:10421-10425 and McNellis, et al., (1998) *Plant J.* 14(2):247-257); copper-inducible system promoters; salicylate-inducible system promoters (e.g., the PR1a system); glucocorticoid-inducible promoters (Aoyama et al. (1997) *Plant J.* 11:605-612); and ecdysone-inducible system promoters. Tissue-preferred and tissue-specific promoters can be used to control expression in a particular plant tissue. Such tissue-preferred and tissue-specific promoters include leaf-preferred promoter, root-preferred promoters; root-specific promoters, seed-preferred promoters; seed-specific promoters; and the like.

As noted above, the present disclosure provides a recombinant expression vector comprising a nucleic acid comprising a nucleotide sequence encoding an Acr polypeptide of the present disclosure. As noted above, the present disclosure provides a recombinant expression vector comprising a nucleic acid comprising a nucleotide sequence encoding an Acr fusion polypeptide of the present disclosure.

Suitable expression vectors include viral expression vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (AAV) (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:38223828; Mendelson et al., Virol. (1988) 166:154165; and Flotte et al., PNAS (1993) 90:1061310617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. In some cases, a recombinant expression vector of the present disclosure is a recombinant adeno-associated virus (AAV) vector. In some cases, a recombinant expression vector of the present disclosure is a recombinant lentivirus vector. In some cases, a recombinant expression vector of the present disclosure is a recombinant retroviral vector.

Depending on the host/vector system utilized, any of a number of suitable transcription and translation control elements, including constitutive and inducible promoters, transcription enhancer elements, transcription terminators, etc. may be used in the expression vector.

Methods of introducing a nucleic acid (e.g., DNA or RNA) (e.g., a nucleic acid comprising a nucleotide sequence encoding an Acr polypeptide of the present disclosure; a nucleic acid comprising a nucleotide sequence encoding an Acr fusion polypeptide of the present disclosure; a nucleic acid encoding a Cas9 polypeptide; Cas9 guide RNA; a nucleic acid comprising a nucleotide sequence encoding a Cas9 guide RNA; a recombinant expression vector comprising one or more of the aforementioned nucleic acids; and the like) into a host cell are known in the art, and any convenient method can be used to introduce a nucleic acid (e.g., an expression construct) into a cell. Suitable methods include e.g., viral infection, transfection, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct microinjection, nanoparticle-mediated nucleic acid delivery, and the like.

Introducing a recombinant expression vector of the present disclosure into a cell or cells can occur in any culture media and under any culture conditions that promote the survival of the cells. Introducing the recombinant expression vector into a target cell can be carried out in vivo or ex vivo. Introducing the recombinant expression vector into a target cell can be carried out in vitro.

In some embodiments, an Acr polypeptide-encoding nucleic acid can be provided as RNA. The RNA can be provided by direct chemical synthesis or may be transcribed in vitro from a DNA (e.g., encoding the Acr polypeptide). Once synthesized, the RNA may be introduced into a cell by any of the well-known techniques for introducing nucleic acids into cells (e.g., microinjection, electroporation, transfection, etc.).

Nucleic acids may be provided to the cells using well-developed transfection techniques; see, e.g. Angel and Yanik (2010) *PLoS One* 5(7): e11756, and the commercially available TransMessenger® reagents from Qiagen, Stemfect™ RNA Transfection Kit from Stemgent, and TransIT®-mRNA Transfection Kit from Minis Bio LLC. See also Beumer et al. (2008) *Proc. Natl. Acad. Sci. USA* 105(50): 19821-19826.

Vectors may be provided directly to a target host cell. In other words, the cells are contacted with a recombinant expression vector comprising a nucleic acid (e.g., a recombinant expression vector comprising a nucleic acid encoding an Acr polypeptide; a recombinant expression vector comprising: i) a nucleic acid encoding an Acr polypeptide; ii) a nucleotide sequence encoding a Cas9 polypeptide; and iii) a nucleotide sequence encoding a Cas9 guide RNA; etc.) such that the vectors are taken up by the cells. Methods for contacting cells with nucleic acid vectors that are plasmids, include electroporation, calcium chloride transfection, microinjection, and lipofection are well known in the art. For viral vector delivery, cells can be contacted with viral particles comprising the subject viral expression vectors.

Retroviruses, for example, lentiviruses, are suitable for use in methods of the present disclosure. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing subject vector expression vectors into packaging cell lines and of collecting the viral particles that are generated by the packaging lines are well known in the art. Nucleic acids can also introduced by direct micro-injection (e.g., injection of RNA).

A recombinant expression vector used for providing a nucleic acid comprising a nucleotide sequence encoding an Acr polypeptide (and, optionally, encoding a Cas9 polypeptide and/or a Cas9 guide RNA) to a target host cell can include suitable promoters for driving the expression, that is, transcriptional activation, of the nucleic acid of interest. In other words, in some cases, the nucleic acid of interest will be operably linked to a promoter. In addition, recombinant expression vector used for providing a nucleic acid comprising a nucleotide sequence encoding an Acr polypeptide (and, optionally, encoding a Cas9 polypeptide and/or a Cas9 guide RNA) to a cell may include nucleic acid sequences that encode for selectable markers in the target cells, so as to identify cells that have taken up the recombinant expression vector.

In some cases, an expression vector of the present disclosure comprises: a) a nucleotide sequence encoding an Acr polypeptide of the present disclosure; and b) a nucleotide sequence encoding a Cas9 polypeptide (where the Cas9 polypeptide is one that can be inhibited by an Acr polypeptide of the present disclosure, where such Cas9 polypeptides are described above). In some cases, the nucleotide sequence encoding the Acr polypeptide and the nucleotide sequence encoding the Cas9 polypeptide are operably linked to the same promoter. In some cases, the nucleotide sequence encoding the Acr polypeptide is operably linked to a first promoter; and the nucleotide sequence encoding the Cas9 polypeptide is operably linked to a second promoter, where the second promoter is different from the first promoter.

In some cases, an expression vector of the present disclosure comprises: a) a nucleotide sequence encoding an Acr polypeptide of the present disclosure; b) a nucleotide sequence encoding a Cas9 polypeptide (where the Cas9 polypeptide is one that can be inhibited by an Acr polypeptide of the present disclosure, where such Cas9 polypeptides are described above); and c) a nucleotide sequence encoding a Cas9 guide RNA. In some cases, the nucleotide sequence encoding the Acr polypeptide, the nucleotide sequence encoding the Cas9 polypeptide, and the nucleotide sequence encoding the Cas9 guide RNA are operably linked to the same promoter. In some cases, the nucleotide sequence encoding the Acr polypeptide is operably linked to a first promoter; and the nucleotide sequence encoding the Cas9 polypeptide and the nucleotide sequence encoding the Cas9 guide RNA are operably linked to a second promoter, where the second promoter is different from the first promoter.

Modified Host Cells

The present disclosure provides a modified host cell comprising an Acr polypeptide of the present disclosure and/or a nucleic acid (e.g., a recombinant expression vector) comprising a nucleotide sequence encoding an Acr polypeptide of the present disclosure. In some cases, the modified host cell is one that does not normally comprise an Acr polypeptide of the present disclosure; i.e., the Acr polypeptide is heterologous to the host cell.

The present disclosure provides a modified cell (e.g., a genetically modified cell) comprising nucleic acid comprising a nucleotide sequence encoding an Acr polypeptide of the present disclosure. The present disclosure provides a genetically modified cell that is genetically modified with an mRNA comprising a nucleotide sequence encoding an Acr polypeptide of the present disclosure. The present disclosure provides a genetically modified cell that is genetically modified with a recombinant expression vector comprising a nucleotide sequence encoding an Acr polypeptide of the present disclosure. The present disclosure provides a genetically modified cell that is genetically modified with a recombinant expression vector comprising: a) a nucleotide sequence encoding an Acr polypeptide of the present disclosure; b) a nucleotide sequence encoding a Cas9 polypeptide (where the Cas9 polypeptide is inhibited by an Acr polypeptide of the present disclosure); and c) a nucleotide sequence encoding a Cas9 guide RNA.

A cell that serves as a recipient for an Acr polypeptide of the present disclosure and/or a nucleic acid comprising a nucleotide sequence encoding an Acr polypeptide of the present disclosure can be any of a variety of cells, including, e.g., in vitro cells; in vivo cells; ex vivo cells; primary cells; cancer cells; animal cells; plant cells; algal cells; fungal cells; insect cells; arachnid cells; etc. A cell that serves as a recipient for an Acr polypeptide of the present disclosure and/or a nucleic acid comprising a nucleotide sequence encoding an Acr polypeptide of the present disclosure is referred to as a "host cell" or a "target cell." A host cell or a target cell can be a recipient of an Acr system of the present disclosure. A host cell or a target cell can be a recipient of a single component of an Acr system of the present disclosure.

Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatoes, rice, cassava, sugarcane, pumpkin, hay, potatoes, cotton, cannabis, tobacco, flowering plants, conifers, gymnosperms, angiosperms, ferns, clubmosses, hornworts, liverworts, mosses, dicotyledons, monocotyledons, etc.), an algal cell, (e.g., *Botryococcus braunii, Chlamydomonas reinhardtii, Nannochloropsis gaditana, Chlorella pyrenoidosa, Sargassum patens, C. agardh*, and the like), seaweeds (e.g. kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep, a horse, a camel); a rodent (e.g., a rat, a mouse); a non-human primate; a human; a feline (e.g., a cat); a canine (e.g., a dog); etc.) and the like. In some cases, the cell is a cell that does not originate from a natural organism (e.g., the cell can be a synthetically made cell; also referred to as an artificial cell). In some instances, modified host cells can be cells within a tissue in a vertebrate animal (e.g. a liver cell, a muscle cell, a pulmonary cell, a pancreatic cell, a skin cell, a renal cell, a cell in the CNS etc). In some instances, the cell can be a specific cell type within a tissue (e.g. a neuron or an astrocyte in brain tissue or a hepatocyte or Kupfer cell in liver tissue).

A cell can be an in vitro cell (e.g., a cell in culture, e.g., an established cultured cell line). A cell can be an ex vivo cell (cultured cell from an individual). A cell can be an in vivo cell (e.g., a cell in an individual). A cell can be an isolated cell. A cell can be a cell inside of an organism. A cell can be an organism. A cell can be a cell in a cell culture (e.g., in vitro cell culture). A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbe cell or derived from a microbe cell. A cell can be a fungi cell or derived from a fungi cell. A cell can be an insect cell. A cell can be an arthropod cell. A cell can be a protozoan cell. A cell can be a helminth cell.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell.

Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some cases, the stem cell is a hematopoietic stem cell (HSC). HSCs are mesoderm-derived cells that can be isolated from bone marrow, blood, cord blood, fetal liver and yolk sac. HSCs are characterized as CD34+ and CD3−. HSCs can repopulate the erythroid, neutrophil-macrophage, megakaryocyte and lymphoid hematopoietic cell lineages in vivo. HSCs can be induced in vitro to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other instances, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other cases, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

A cell is in some cases a plant cell. A plant cell can be a cell of a monocotyledon. A cell can be a cell of a dicotyledon.

In some cases, the cell is a plant cell. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (rappini), brussels sprouts, cabbage, cabbage sprouts, cactus leaf (nopales), calabaza, cardoon, carrots, cauliflower, celery, chayote, chinese artichoke (crosnes), chinese cabbage, chinese celery, chinese chives, choy sum, chrysanthemum leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf—green), lettuce (oak leaf—red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, salicornia (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams (names), yu choy, yuca (cassava), and the like.

A cell is in some cases an arthropod cell. For example, the cell can be a cell of a sub-order, a family, a sub-family, a group, a sub-group, or a species of, e.g., *Chelicerata, Myriapodia, Hexipodia, Arachnida, Insecta, Archaeognatha, Thysanura, Palaeoptera, Ephemeroptera, Odonata, Anisoptera, Zygoptera, Neoptera, Exopterygota, Plecoptera, Embioptera, Orthoptera, Zoraptera, Dermaptera, Dictyoptera, Notoptera, Grylloblattidae, Mantophasmatidae, Phasmatodea, Blattaria, Isoptera, Mantodea, Parapneuroptera, Psocoptera, Thysanoptera, Phthiraptera, Hemiptera, Endopterygota or Holometabola, Hymenoptera, Coleoptera, Strepsiptera, Raphidioptera, Megaloptera, Neuroptera, Mecoptera, Siphonaptera, Diptera, Trichoptera*, or *Lepidoptera*.

A cell is in some cases an insect cell. For example, in some cases, the cell is a cell of a mosquito, a grasshopper, a true bug, a fly, a flea, a bee, a wasp, an ant, a louse, a moth, or a beetle.

Compositions

The present disclosure provides a composition comprising an Acr polypeptide of the present disclosure. The present disclosure comprises a composition comprising a nucleic acid or a recombinant expression vector comprising a nucleotide sequence encoding an Acr polypeptide of the present disclosure. The present disclosure provides a composition comprising an Acr fusion polypeptide of the present disclosure. The present disclosure provides a composition comprising a host cell comprising an Acr polypeptide of the present disclosure.

For example, one or more of: a) recombinant expression vector comprising a nucleotide sequence encoding an Acr polypeptide of the present disclosure or an Acr fusion polypeptide of the present disclosure (where the recombinant expression vector may optionally include one or both of: i) a nucleotide sequence encoding a Cas9 polypeptide (where the Cas9 polypeptide is one whose activity can be inhibited by the Acr polypeptide); and ii) a nucleotide sequence encoding a Cas9 guide RNA); b) a Cas9 polypeptide (where the Cas9 polypeptide is one whose activity can be inhibited by the Acr polypeptide); c) a recombinant expression vector comprising a nucleotide sequence encoding a Cas9 polypeptide (where the Cas9 polypeptide is one whose activity can be inhibited by the Acr polypeptide); d) an RNA comprising a nucleotide sequence encoding a Cas9 polypeptide (where the Cas9 polypeptide is one whose activity can be inhibited by the Acr polypeptide); e) a Cas9 guide RNA; f) a DNA comprising a nucleotide sequence encoding a Cas9 guide RNA; and g) an Acr polypeptide or an Acr fusion polypeptide of the present disclosure, can be delivered (non-contemporaneously or simultaneously) using particles or lipids (e.g., liposomes). For example, any one of, or any combination of, (a)-(g) as set out above can be delivered associated with, or encapsulated in, a nanoparticle. For example, any one of, or any combination of, (a)-(g) as set out above can be delivered associated with, or encapsulated in, a lipid composition, e.g., a lipid composition (such as a liposome) comprising a lipid or lipidoid and a hydrophilic polymer, e.g., a cationic lipid and a hydrophilic polymer, for instance wherein the cationic lipid comprises 1,2-dioleoyl-3-trimethylammonium-propane (DOTAP) or 1,2-ditetradecanoyl-sn-glycero-3-phosphocholine (DMPC) and/or wherein the hydrophilic polymer comprises ethylene glycol or polyethylene glycol (PEG); and/or wherein the lipid composition further comprises cholesterol (e.g., particle from formulation 1=DOTAP 100, DMPC 0, PEG 0, Cholesterol 0; formulation number 2=DOTAP 90, DMPC 0, PEG 10, Cholesterol 0; formulation number 3=DOTAP 90, DMPC 0, PEG 5, Cholesterol 5). For example, a lipid composition can be formed using a multistep process in which an Acr polypeptide, a Cas9 polypeptide, and a Cas9 guideRNA are mixed together, e.g., at a 1:1:1 molar ratio, e.g., at room temperature, e.g., for 30 minutes, e.g., in sterile, nuclease free 1× phosphate-buffered saline (PBS); and separately, DOTAP, DMPC, PEG, and cholesterol as applicable for the formulation are dissolved in alcohol, e.g., 100% ethanol; and, the two solutions are mixed together to form particles containing the complexes).

In some cases, one or more of: a) recombinant expression vector comprising a nucleotide sequence encoding an Acr polypeptide of the present disclosure or an Acr fusion polypeptide of the present disclosure (where the recombinant expression vector may optionally include one or both of: i) a nucleotide sequence encoding a Cas9 polypeptide (where the Cas9 polypeptide is one whose activity can be inhibited by the Acr polypeptide); and ii) a nucleotide sequence encoding a Cas9 guide RNA); b) a Cas9 polypeptide (where the Cas9 polypeptide is one whose activity can be inhibited by the Acr polypeptide); c) a recombinant expression vector comprising a nucleotide sequence encoding a Cas9 polypeptide (where the Cas9 polypeptide is one whose activity can be inhibited by the Acr polypeptide); d) an RNA comprising a nucleotide sequence encoding a Cas9 polypeptide (where the Cas9 polypeptide is one whose activity can be inhibited by the Acr polypeptide); e) a Cas9 guide RNA; f) a DNA comprising a nucleotide sequence encoding a Cas9 guide RNA; and g) an Acr polypeptide or an Acr fusion polypeptide of the present disclosure, are delivered using particles or lipid envelopes. For example, a biodegradable core-shell structured nanoparticle with a poly (β-amino ester) (PBAE) core enveloped by a phospholipid bilayer shell can be used. In some cases, particles/nanoparticles based on self assembling bioadhesive polymers are used; such particles/nanoparticles may be applied to oral delivery of peptides, intravenous delivery of peptides and nasal delivery of peptides, e.g., to the brain. Other embodiments, such as oral absorption and ocular delivery of hydrophobic drugs are also contemplated. A molecular envelope technology, which involves an engineered polymer envelope which is protected and delivered to the site of the disease, can be used. Doses of about 5 mg/kg can be used, with single or multiple doses, depending on various factors, e.g., the target tissue.

Lipidoid compounds (e.g., as described in US patent application 20110293703) are also useful in the administration of polynucleotides, and can be used to deliver one or more of: a) recombinant expression vector comprising a nucleotide sequence encoding an Acr polypeptide of the present disclosure or an Acr fusion polypeptide of the present disclosure (where the recombinant expression vector may optionally include one or both of: i) a nucleotide sequence encoding a Cas9 polypeptide (where the Cas9 polypeptide is one whose activity can be inhibited by the Acr polypeptide); and ii) a nucleotide sequence encoding a Cas9 guide RNA); b) a Cas9 polypeptide (where the Cas9 polypeptide is one whose activity can be inhibited by the Acr polypeptide); c) a recombinant expression vector comprising a nucleotide sequence encoding a Cas9 polypeptide (where the Cas9 polypeptide is one whose activity can be inhibited by the Acr polypeptide); d) an RNA comprising a nucleotide sequence encoding a Cas9 polypeptide (where the Cas9 polypeptide is one whose activity can be inhibited by the Acr polypeptide); e) a Cas9 guide RNA; f) a DNA comprising a nucleotide sequence encoding a Cas9 guide RNA; and g) an Acr polypeptide or an Acr fusion polypeptide of the present disclosure. In one aspect, the aminoalcohol lipidoid compounds are combined with an agent (one or more of (a)-(f), above), to be delivered to a cell or a subject to form microparticles, nanoparticles, liposomes, or micelles. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

A poly(beta-amino alcohol) (PBAA) can be used to deliver one or more of: a) recombinant expression vector comprising a nucleotide sequence encoding an Acr polypeptide of the present disclosure or an Acr fusion polypeptide of the present disclosure (where the recombinant expression vector may optionally include one or both of: i) a nucleotide sequence encoding a Cas9 polypeptide (where the Cas9 polypeptide is one whose activity can be inhibited by the Acr polypeptide); and ii) a nucleotide sequence encoding a Cas9 guide RNA); b) a Cas9 polypeptide (where the Cas9 polypeptide is one whose activity can be inhibited by the Acr polypeptide); c) a recombinant expression vector comprising a nucleotide sequence encoding a Cas9 polypeptide (where the Cas9 polypeptide is one whose activity can be inhibited by the Acr polypeptide); d) an RNA comprising a nucleotide sequence encoding a Cas9 polypeptide (where the Cas9 polypeptide is one whose activity can be inhibited by the Acr polypeptide); e) a Cas9 guide RNA; f) a DNA comprising a nucleotide sequence encoding a Cas9 guide RNA; and g) an Acr polypeptide or an Acr fusion polypeptide of the present disclosure, to a target cell. US Patent Publication No. 20130302401 relates to a class of poly(beta-amino alcohols) (PBAAs) that has been prepared using combinatorial polymerization.

Sugar-based particles may be used, for example GalNAc, as described with reference to WO2014118272 (incorporated herein by reference) and Nair, J K et al., 2014, Journal of the American Chemical Society 136 (49), 16958-16961) can be used to deliver one or more of: a) recombinant expression vector comprising a nucleotide sequence encoding an Acr polypeptide of the present disclosure or an Acr fusion polypeptide of the present disclosure (where the recombinant expression vector may optionally include one or both of: i) a nucleotide sequence encoding a Cas9 polypeptide (where the Cas9 polypeptide is one whose activity can be inhibited by the Acr polypeptide); and ii) a nucleotide sequence encoding a Cas9 guide RNA); b) a Cas9 polypeptide (where the Cas9 polypeptide is one whose activity can be inhibited by the Acr polypeptide); c) a recombinant expression vector comprising a nucleotide sequence encoding a Cas9 polypeptide (where the Cas9 polypeptide is one whose activity can be inhibited by the Acr polypeptide); d) an RNA comprising a nucleotide sequence encoding a Cas9 polypeptide (where the Cas9 polypeptide is one whose activity can be inhibited by the Acr polypeptide); e) a Cas9 guide RNA; f) a DNA comprising a nucleotide sequence encoding a Cas9 guide RNA; and g) an Acr polypeptide or an Acr fusion polypeptide of the present disclosure, to a target cell.

In some cases, lipid nanoparticles (LNPs) are used to deliver one or more of: a) recombinant expression vector comprising a nucleotide sequence encoding an Acr polypeptide of the present disclosure or an Acr fusion polypeptide of the present disclosure (where the recombinant expression vector may optionally include one or both of: i) a nucleotide sequence encoding a Cas9 polypeptide (where the Cas9 polypeptide is one whose activity can be inhibited by the Acr polypeptide); and ii) a nucleotide sequence encoding a Cas9 guide RNA); b) a Cas9 polypeptide (where the Cas9 polypeptide is one whose activity can be inhibited by the Acr polypeptide); c) a recombinant expression vector comprising a nucleotide sequence encoding a Cas9 polypeptide (where the Cas9 polypeptide is one whose activity can be inhibited by the Acr polypeptide); d) an RNA comprising a nucleotide sequence encoding a Cas9 polypeptide (where the Cas9 polypeptide is one whose activity can be inhibited by the Acr polypeptide); e) a Cas9 guide RNA; f) a DNA comprising a nucleotide sequence encoding a Cas9 guide RNA; and g) an Acr polypeptide or an Acr fusion polypeptide of the present disclosure, to a target cell. Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethylammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)-[1,3]-dioxolane (DLinKC2-DMA). Preparation of LNPs and is described in, e.g., Rosin et al. (2011) Molecular Therapy 19:1286-2200). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG), and R-3-[(omega-methoxy-poly(ethylene glycol)2000) carbamoyl]-1,2-dimyristyloxlpropyl-3-amine (PEG-C-DOMG) may be used. A nucleic acid (e.g., a Cas9 guide RNA; a nucleic acid of the present disclosure; etc.) may be encapsulated in LNPs containing DLinDAP, DLinDMA, DLinK-DMA, and DLinKC2-DMA (cationic lipid:DSPC:CHOL:PEGS-DMG or PEG-C-DOMG at 40:10:40:10 molar ratios). In some cases, 0.2% SP-DiOC18 is incorporated.

Spherical Nucleic Acid (SNA™) constructs and other nanoparticles (particularly gold nanoparticles) can be used to deliver one or more of: a) recombinant expression vector comprising a nucleotide sequence encoding an Acr polypeptide of the present disclosure or an Acr fusion polypeptide of the present disclosure (where the recombinant expression vector may optionally include one or both of: i) a nucleotide sequence encoding a Cas9 polypeptide (where the Cas9 polypeptide is one whose activity can be inhibited by the Acr polypeptide); and ii) a nucleotide sequence encoding a Cas9 guide RNA); b) a Cas9 polypeptide (where the Cas9 polypeptide is one whose activity can be inhibited by the Acr polypeptide); c) a recombinant expression vector comprising a nucleotide sequence encoding a Cas9 polypeptide (where the Cas9 polypeptide is one whose activity can be inhibited by the Acr polypeptide); d) an RNA comprising a nucleotide sequence encoding a Cas9 polypeptide (where the Cas9 polypeptide is one whose activity can be inhibited by the Acr polypeptide); e) a Cas9 guide RNA; f) a DNA comprising a nucleotide sequence encoding a Cas9 guide RNA; and g) an Acr polypeptide or an Acr fusion polypeptide of the present disclosure, to a target cell. See, e.g., Cutler et al., J. Am. Chem. Soc. 2011 133:9254-9257, Hao et al., Small. 2011 7:3158-3162, Zhang et al., ACS Nano. 2011 5:6962-6970, Cutler et al., J. Am. Chem. Soc. 2012 134: 1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19): 7625-7630, Jensen et al., Sci. Transl. Med. 5, 209ra152 (2013) and Mirkin, et al., Small, 10:186-192.

Self-assembling nanoparticles with RNA may be constructed with polyethyleneimine (PEI) that is PEGylated with an Arg-Gly-Asp (RGD) peptide ligand attached at the distal end of the polyethylene glycol (PEG).

In general, a "nanoparticle" refers to any particle having a diameter of less than 1000 nm. In some cases, nanoparticles suitable for use in delivering a polypeptide and/or a nucleic acid (e.g., one or more of: a) recombinant expression vector comprising a nucleotide sequence encoding an Acr polypeptide of the present disclosure or an Acr fusion polypeptide of the present disclosure (where the recombinant expression vector may optionally include one or both of: i) a nucleotide sequence encoding a Cas9 polypeptide (where the Cas9 polypeptide is one whose activity can be inhibited by the Acr polypeptide); and ii) a nucleotide sequence encoding a Cas9 guide RNA); b) a Cas9 polypeptide (where the Cas9 polypeptide is one whose activity can be inhibited by the Acr polypeptide); c) a recombinant expression vector comprising a nucleotide sequence encoding a Cas9 polypeptide (where the Cas9 polypeptide is one whose activity can be inhibited by the Acr polypeptide); d) an RNA comprising a nucleotide sequence encoding a Cas9 polypeptide (where the Cas9 polypeptide is one whose activity can be inhibited by the Acr polypeptide); e) a Cas9 guide RNA; f) a DNA comprising a nucleotide sequence encoding a Cas9 guide RNA; and g) an Acr polypeptide or an Acr fusion polypeptide of the present disclosure) to a target cell have a diameter of 500 nm or less, e.g., from 25 nm to 35 nm, from 35 nm to 50 nm, from 50 nm to 75 nm, from 75 nm to 100 nm, from 100 nm to 150 nm, from 150 nm to 200 nm, from 200 nm to 300 nm, from 300 nm to 400 nm, or from 400 nm to 500 nm.

In some cases, nanoparticles suitable for use in delivering a polypeptide and/or a nucleic acid (e.g., one or more of: a) recombinant expression vector comprising a nucleotide sequence encoding an Acr polypeptide of the present disclosure or an Acr fusion polypeptide of the present disclosure (where the recombinant expression vector may optionally include one or both of: i) a nucleotide sequence encoding a Cas9 polypeptide (where the Cas9 polypeptide is one whose activity can be inhibited by the Acr polypeptide); and ii) a nucleotide sequence encoding a Cas9 guide RNA); b) a Cas9 polypeptide (where the Cas9 polypeptide is one whose activity can be inhibited by the Acr polypeptide); c) a recombinant expression vector comprising a nucleotide sequence encoding a Cas9 polypeptide (where the Cas9 polypeptide is one whose activity can be inhibited by the Acr polypeptide); d) an RNA comprising a nucleotide sequence encoding a Cas9 polypeptide (where the Cas9 polypeptide is one whose activity can be inhibited by the Acr polypeptide); e) a Cas9 guide RNA; f) a DNA comprising a nucleotide sequence encoding a Cas9 guide RNA; and g) an Acr polypeptide or an Acr fusion polypeptide of the present disclosure) to a target cell have a diameter of from 25 nm to 200 nm.

In some cases, nanoparticles suitable for use in delivering a polypeptide and/or a nucleic acid (e.g., one or more of: a) recombinant expression vector comprising a nucleotide sequence encoding an Acr polypeptide of the present disclosure or an Acr fusion polypeptide of the present disclosure (where the recombinant expression vector may optionally include one or both of: i) a nucleotide sequence encoding a Cas9 polypeptide (where the Cas9 polypeptide is one whose activity can be inhibited by the Acr polypeptide); and ii) a nucleotide sequence encoding a Cas9 guide RNA); b) a Cas9 polypeptide (where the Cas9 polypeptide is one whose activity can be inhibited by the Acr polypeptide); c) a recombinant expression vector comprising a nucleotide sequence encoding a Cas9 polypeptide (where the Cas9 polypeptide is one whose activity can be inhibited by the Acr polypeptide); d) an RNA comprising a nucleotide sequence encoding a Cas9 polypeptide (where the Cas9 polypeptide is one whose activity can be inhibited by the Acr polypeptide); e) a Cas9 guide RNA; f) a DNA comprising a nucleotide sequence encoding a Cas9 guide RNA; and g) an Acr polypeptide or an Acr fusion polypeptide of the present disclosure) to a target cell have a diameter of 100 nm or less. In some cases, nanoparticles suitable for use in delivering a polypeptide and/or a nucleic acid (e.g., one or more of: a) recombinant expression vector comprising a nucleotide sequence encoding an Acr polypeptide of the present disclosure or an Acr fusion polypeptide of the present disclosure (where the recombinant expression vector may optionally include one or both of: i) a nucleotide sequence encoding a Cas9 polypeptide (where the Cas9 polypeptide is one whose activity can be inhibited by the Acr polypeptide); and ii) a nucleotide sequence encoding a Cas9 guide RNA); b) a Cas9 polypeptide (where the Cas9 polypeptide is one whose activity can be inhibited by the Acr polypeptide); c) a recombinant expression vector comprising a nucleotide sequence encoding a Cas9 polypeptide (where the Cas9 polypeptide is one whose activity can be inhibited by the Acr polypeptide); d) an RNA comprising a nucleotide sequence encoding a Cas9 polypeptide (where the Cas9 polypeptide is one whose activity can be inhibited by the Acr polypeptide); e) a Cas9 guide RNA; f) a DNA comprising a nucleotide sequence encoding a Cas9 guide RNA; and g) an Acr polypeptide or an Acr fusion polypeptide of the present disclosure) to a target cell have a diameter of from 35 nm to 60 nm.

Nanoparticles suitable for use in delivering a polypeptide and/or a nucleic acid (e.g., one or more of: a) recombinant expression vector comprising a nucleotide sequence encoding an Acr polypeptide of the present disclosure or an Acr fusion polypeptide of the present disclosure (where the recombinant expression vector may optionally include one or both of: i) a nucleotide sequence encoding a Cas9 polypeptide (where the Cas9 polypeptide is one whose activity can be inhibited by the Acr polypeptide); and ii) a nucleotide sequence encoding a Cas9 guide RNA); b) a Cas9 polypeptide (where the Cas9 polypeptide is one whose activity can be inhibited by the Acr polypeptide); c) a recombinant expression vector comprising a nucleotide sequence encoding a Cas9 polypeptide (where the Cas9 polypeptide is one whose activity can be inhibited by the Acr polypeptide); d) an RNA comprising a nucleotide sequence encoding a Cas9 polypeptide (where the Cas9 polypeptide is one whose activity can be inhibited by the Acr polypeptide); e) a Cas9 guide RNA; f) a DNA comprising a nucleotide sequence encoding a Cas9 guide RNA; and g) an Acr polypeptide or an Acr fusion polypeptide of the present disclosure) to a target cell may be provided in different forms, e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Nanoparticles made of semiconducting material may also be labeled quantum dots if they are small enough (typically below 10 nm) that quantization of electronic energy levels occurs. Such nanoscale particles are used in biomedical applications as drug carriers or imaging agents and may be adapted for similar purposes in the present disclosure.

Semi-solid and soft nanoparticles are also suitable for use in delivering a polypeptide and/or a nucleic acid (e.g., one or more of: a) recombinant expression vector comprising a nucleotide sequence encoding an Acr polypeptide of the present disclosure or an Acr fusion polypeptide of the present disclosure (where the recombinant expression vector may optionally include one or both of: i) a nucleotide sequence encoding a Cas9 polypeptide (where the Cas9 polypeptide is one whose activity can be inhibited by the Acr polypeptide); and ii) a nucleotide sequence encoding a Cas9 guide RNA); b) a Cas9 polypeptide (where the Cas9 polypeptide is one whose activity can be inhibited by the Acr polypeptide); c) a recombinant expression vector comprising a nucleotide sequence encoding a Cas9 polypeptide (where the Cas9 polypeptide is one whose activity can be inhibited by the Acr polypeptide); d) an RNA comprising a nucleotide sequence encoding a Cas9 polypeptide (where the Cas9 polypeptide is one whose activity can be inhibited by the Acr polypeptide); e) a Cas9 guide RNA; f) a DNA comprising a nucleotide sequence encoding a Cas9 guide RNA; and g) an Acr polypeptide or an Acr fusion polypeptide of the present disclosure) to a target cell. A prototype nanoparticle of semi-solid nature is the liposome.

In some cases, an exosome is used to deliver a polypeptide and/or a nucleic acid (e.g., one or more of: a) recombinant expression vector comprising a nucleotide sequence encoding an Acr polypeptide of the present disclosure or an Acr fusion polypeptide of the present disclosure (where the recombinant expression vector may optionally include one or both of: i) a nucleotide sequence encoding a Cas9 polypeptide (where the Cas9 polypeptide is one whose activity can be inhibited by the Acr polypeptide); and ii) a nucleotide sequence encoding a Cas9 guide RNA); b) a Cas9 polypeptide (where the Cas9 polypeptide is one whose activity can be inhibited by the Acr polypeptide); c) a recombinant expression vector comprising a nucleotide sequence encoding a Cas9 polypeptide (where the Cas9 polypeptide is one whose activity can be inhibited by the Acr polypeptide); d) an RNA comprising a nucleotide sequence encoding a Cas9 polypeptide (where the Cas9 polypeptide is one whose activity can be inhibited by the Acr polypeptide); e) a Cas9 guide RNA; f) a DNA comprising a nucleotide sequence encoding a Cas9 guide RNA; and g) an Acr polypeptide or an Acr fusion polypeptide of the present disclosure) to a target cell. Exosomes are endogenous nanovesicles that transport RNAs and proteins, and which can deliver RNA to the brain and other target organs.

In some cases, a liposome is used to deliver a polypeptide and/or a nucleic acid (e.g., one or more of: a) recombinant expression vector comprising a nucleotide sequence encoding an Acr polypeptide of the present disclosure or an Acr fusion polypeptide of the present disclosure (where the recombinant expression vector may optionally include one or both of: i) a nucleotide sequence encoding a Cas9 polypeptide (where the Cas9 polypeptide is one whose activity can be inhibited by the Acr polypeptide); and ii) a nucleotide sequence encoding a Cas9 guide RNA); b) a Cas9 polypeptide (where the Cas9 polypeptide is one whose activity can be inhibited by the Acr polypeptide); c) a recombinant expression vector comprising a nucleotide sequence encoding a Cas9 polypeptide (where the Cas9 polypeptide is one whose activity can be inhibited by the Acr polypeptide); d) an RNA comprising a nucleotide sequence encoding a Cas9 polypeptide (where the Cas9 polypeptide is one whose activity can be inhibited by the Acr polypeptide); e) a Cas9 guide RNA; f) a DNA comprising a nucleotide sequence encoding a Cas9 guide RNA; and g) an Acr polypeptide or an Acr fusion polypeptide of the present disclosure) to a target cell. Liposomes are spherical vesicle structures composed of a uni- or multilamellar lipid bilayer surrounding internal aqueous compartments and a relatively impermeable outer lipophilic phospholipid bilayer. Liposomes can be made from several different types of lipids; however, phospholipids are most commonly used to generate liposomes. Although liposome formation is spontaneous when a lipid film is mixed with an aqueous solution, it can also be expedited by applying force in the form of shaking by using a homogenizer, sonicator, or an extrusion apparatus. Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. A liposome formulation may be mainly comprised of natural phospholipids and lipids such as 1,2-distearoryl-sn-glycero-3-phosphatidyl choline (DSPC), sphingomyelin, egg phosphatidylcholines and monosialoganglioside.

A stable nucleic-acid-lipid particle (SNALP) can be used to deliver a polypeptide and/or a nucleic acid (e.g., one or more of: a) recombinant expression vector comprising a nucleotide sequence encoding an Acr polypeptide of the present disclosure or an Acr fusion polypeptide of the present disclosure (where the recombinant expression vector may optionally include one or both of: i) a nucleotide sequence encoding a Cas9 polypeptide (where the Cas9 polypeptide is one whose activity can be inhibited by the Acr polypeptide); and ii) a nucleotide sequence encoding a Cas9 guide RNA); b) a Cas9 polypeptide (where the Cas9 polypeptide is one whose activity can be inhibited by the Acr polypeptide); c) a recombinant expression vector comprising a nucleotide sequence encoding a Cas9 polypeptide (where the Cas9 polypeptide is one whose activity can be inhibited by the Acr polypeptide); d) an RNA comprising a nucleotide sequence encoding a Cas9 polypeptide (where the Cas9 polypeptide is one whose activity can be inhibited by the Acr polypeptide); e) a Cas9 guide RNA; f) a DNA comprising a nucleotide sequence encoding a Cas9 guide RNA; and g) an Acr polypeptide or an Acr fusion polypeptide of the present disclosure) to a target cell. The SNALP formulation may contain the lipids 3-N-[(methoxypoly(ethylene glycol) 2000) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio. The SNALP liposomes may be prepared by formulating D-Lin-DMA and PEG-C-DMA with distearoylphosphatidylcholine (DSPC), Cholesterol and siRNA using a 25:1 lipid/siRNA ratio and a 48/40/10/2 molar ratio of Cholesterol/D-Lin-DMA/DSPC/PEG-C-DMA. The resulting SNALP liposomes can be about 80-100 nm in size. A SNALP may comprise synthetic cholesterol (Sigma-Aldrich, St Louis, Mo., USA), dipalmitoylphosphatidylcholine (Avanti Polar Lipids, Alabaster, Ala., USA), 3-N-[(w-methoxy poly(ethylene glycol)2000)carbamoyl]-1,2-dimyrestyloxypropylamine, and cationic 1,2-dilinoleyloxy-3-N,Ndimethylaminopropane. A SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N;N-dimethyl)aminopropane (DLinDMA).

Other cationic lipids, such as amino lipid 2,2-dilinoleyl-4-dimethylaminoethyl-[1,3]-dioxolane (DLin-KC2-DMA) can be used to deliver a polypeptide and/or a nucleic acid (e.g., one or more of: a) recombinant expression vector comprising a nucleotide sequence encoding an Acr polypeptide of the present disclosure or an Acr fusion polypeptide of the present disclosure (where the recombinant expression vector may optionally include one or both of: i) a nucleotide sequence encoding a Cas9 polypeptide (where the Cas9 polypeptide is one whose activity can be inhibited by the Acr polypeptide); and ii) a nucleotide sequence encoding a Cas9 guide RNA); b) a Cas9 polypeptide (where the Cas9 polypeptide is one whose activity can be inhibited by the Acr polypeptide); c) a recombinant expression vector comprising a nucleotide sequence encoding a Cas9 polypeptide (where the Cas9 polypeptide is one whose activity can be inhibited by the Acr polypeptide); d) an RNA comprising a nucleotide sequence encoding a Cas9 polypeptide (where the Cas9 polypeptide is one whose activity can be inhibited by the Acr polypeptide); e) a Cas9 guide RNA; f) a DNA comprising a nucleotide sequence encoding a Cas9 guide RNA; and g) an Acr polypeptide or an Acr fusion polypeptide of the present disclosure) to a target cell. A preformed vesicle with the following lipid composition may be contemplated: amino lipid, distearoylphosphatidylcholine (DSPC), cholesterol and (R)-2,3-bis(octadecyloxy) propyl-1-(methoxy poly(ethylene glycol)2000)propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11.+−0.04 (n=56), the particles may be extruded up to three times through 80 nm membranes prior to adding the guide RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Lipids may be formulated with a polypeptide and/or a nucleic acid (e.g., one or more of: a) recombinant expression vector comprising a nucleotide sequence encoding an Acr polypeptide of the present disclosure or an Acr fusion polypeptide of the present disclosure (where the recombinant expression vector may optionally include one or both of: i) a nucleotide sequence encoding a Cas9 polypeptide (where the Cas9 polypeptide is one whose activity can be inhibited by the Acr polypeptide); and ii) a nucleotide sequence encoding a Cas9 guide RNA); b) a Cas9 polypeptide (where the Cas9 polypeptide is one whose activity can be inhibited by the Acr polypeptide); c) a recombinant expression vector comprising a nucleotide sequence encoding a Cas9 polypeptide (where the Cas9 polypeptide is one whose activity can be inhibited by the Acr polypeptide); d) an RNA comprising a nucleotide sequence encoding a Cas9 polypeptide (where the Cas9 polypeptide is one whose activity can be inhibited by the Acr polypeptide); e) a Cas9 guide RNA; f) a DNA comprising a nucleotide sequence encoding a Cas9 guide RNA; and g) an Acr polypeptide or an Acr fusion polypeptide of the present disclosure) to form lipid nanoparticles (LNPs). Suitable lipids include, but are not limited to, DLin-KC2-DMA4, C12-200 and colipids disteroylphosphatidyl choline, cholesterol, and PEG-DMG may be formulated with a system, or component thereof, of the present disclosure, using a spontaneous vesicle formation procedure. The component molar ratio may be about 50/10/38.5/1.5 (DLin-KC2-DMA or C12-200/disteroylphosphatidyl choline/cholesterol/PEG-DMG).

A polypeptide and/or a nucleic acid (e.g., one or more of: a) recombinant expression vector comprising a nucleotide sequence encoding an Acr polypeptide of the present disclosure or an Acr fusion polypeptide of the present disclosure (where the recombinant expression vector may optionally include one or both of: i) a nucleotide sequence encoding a Cas9 polypeptide (where the Cas9 polypeptide is one whose activity can be inhibited by the Acr polypeptide); and ii) a nucleotide sequence encoding a Cas9 guide RNA); b) a Cas9 polypeptide (where the Cas9 polypeptide is one whose activity can be inhibited by the Acr polypeptide); c) a recombinant expression vector comprising a nucleotide sequence encoding a Cas9 polypeptide (where the Cas9 polypeptide is one whose activity can be inhibited by the Acr polypeptide); d) an RNA comprising a nucleotide sequence encoding a Cas9 polypeptide (where the Cas9 polypeptide is one whose activity can be inhibited by the Acr polypeptide); e) a Cas9 guide RNA; f) a DNA comprising a nucleotide sequence encoding a Cas9 guide RNA; and g) an Acr polypeptide or an Acr fusion polypeptide of the present disclosure) may be delivered encapsulated in PLGA microspheres such as that further described in US published applications 20130252281 and 20130245107 and 20130244279.

Supercharged proteins can be used to deliver a polypeptide and/or a nucleic acid (e.g., one or more of: a) recombinant expression vector comprising a nucleotide sequence encoding an Acr polypeptide of the present disclosure or an Acr fusion polypeptide of the present disclosure (where the recombinant expression vector may optionally include one or both of: i) a nucleotide sequence encoding a Cas9 polypeptide (where the Cas9 polypeptide is one whose activity can be inhibited by the Acr polypeptide); and ii) a nucleotide sequence encoding a Cas9 guide RNA); b) a Cas9 polypeptide (where the Cas9 polypeptide is one whose activity can be inhibited by the Acr polypeptide); c) a recombinant expression vector comprising a nucleotide sequence encoding a Cas9 polypeptide (where the Cas9 polypeptide is one whose activity can be inhibited by the Acr polypeptide); d) an RNA comprising a nucleotide sequence encoding a Cas9 polypeptide (where the Cas9 polypeptide is one whose activity can be inhibited by the Acr polypeptide); e) a Cas9 guide RNA; f) a DNA comprising a nucleotide sequence encoding a Cas9 guide RNA; and g) an Acr polypeptide or an Acr fusion polypeptide of the present disclosure) to a target cell. Supercharged proteins are a class of engineered or naturally occurring proteins with unusually high positive or negative net theoretical charge. Both supernegatively and superpositively charged proteins exhibit the ability to withstand thermally or chemically induced aggregation. Superpositively charged proteins are also able to penetrate mammalian cells. Associating cargo with these proteins, such as plasmid DNA, RNA, or other proteins, can enable the functional delivery of these macromolecules into mammalian cells both in vitro and in vivo.

Cell Penetrating Peptides (CPPs) can be used to deliver a polypeptide and/or a nucleic acid (e.g., one or more of: a) recombinant expression vector comprising a nucleotide sequence encoding an Acr polypeptide of the present disclosure or an Acr fusion polypeptide of the present disclosure (where the recombinant expression vector may optionally include one or both of: i) a nucleotide sequence encoding a Cas9 polypeptide (where the Cas9 polypeptide is one whose activity can be inhibited by the Acr polypeptide); and ii) a nucleotide sequence encoding a Cas9 guide RNA); b) a Cas9 polypeptide (where the Cas9 polypeptide is one whose activity can be inhibited by the Acr polypeptide); c) a recombinant expression vector comprising a nucleotide sequence encoding a Cas9 polypeptide (where the Cas9 polypeptide is one whose activity can be inhibited by the Acr polypeptide); d) an RNA comprising a nucleotide sequence encoding a Cas9 polypeptide (where the Cas9 polypeptide is one whose activity can be inhibited by the Acr polypeptide); e) a Cas9 guide RNA; f) a DNA comprising a nucleotide sequence encoding a Cas9 guide RNA; and g) an Acr polypeptide or an Acr fusion polypeptide of the present disclosure) to a target cell. CPPs typically have an amino acid composition that either contains a high relative abundance of positively charged amino acids such as lysine or arginine or has sequences that contain an alternating pattern of polar/charged amino acids and non-polar, hydrophobic amino acids.

An implantable device can be used to deliver a polypeptide and/or a nucleic acid (e.g., one or more of: a) recombinant expression vector comprising a nucleotide sequence encoding an Acr polypeptide of the present disclosure or an Acr fusion polypeptide of the present disclosure (where the recombinant expression vector may optionally include one or both of: i) a nucleotide sequence encoding a Cas9 polypeptide (where the Cas9 polypeptide is one whose activity can be inhibited by the Acr polypeptide); and ii) a nucleotide sequence encoding a Cas9 guide RNA); b) a Cas9 polypeptide (where the Cas9 polypeptide is one whose activity can be inhibited by the Acr polypeptide); c) a recombinant expression vector comprising a nucleotide sequence encoding a Cas9 polypeptide (where the Cas9 polypeptide is one whose activity can be inhibited by the Acr polypeptide); d) an RNA comprising a nucleotide sequence encoding a Cas9 polypeptide (where the Cas9 polypeptide is one whose activity can be inhibited by the Acr polypeptide); e) a Cas9 guide RNA; f) a DNA comprising a nucleotide sequence encoding a Cas9 guide RNA; and g) an Acr polypeptide or an Acr fusion polypeptide of the present disclosure) to a target cell (e.g., a target cell in vivo, where the target cell is a target cell in circulation, a target cell in a tissue, a target cell in an organ, etc.). An implantable device suitable for use in delivering a polypeptide and/or a nucleic acid (e.g., one or more of: a) recombinant expression vector comprising a nucleotide sequence encoding an Acr polypeptide of the present disclosure or an Acr fusion polypeptide of the present disclosure (where the recombinant expression vector may optionally include one or both of: i) a nucleotide sequence encoding a Cas9 polypeptide (where the Cas9 polypeptide is one whose activity can be inhibited by the Acr polypeptide); and ii) a nucleotide sequence encoding a Cas9 guide RNA); b) a Cas9 polypeptide (where the Cas9 polypeptide is one whose activity can be inhibited by the Acr polypeptide); c) a recombinant expression vector comprising a nucleotide sequence encoding a Cas9 polypeptide (where the Cas9 polypeptide is one whose activity can be inhibited by the Acr polypeptide); d) an RNA comprising a nucleotide sequence encoding a Cas9 polypeptide (where the Cas9 polypeptide is one whose activity can be inhibited by the Acr polypeptide); e) a Cas9 guide RNA; f) a DNA comprising a nucleotide sequence encoding a Cas9 guide RNA; and g) an Acr polypeptide or an Acr fusion polypeptide of the present disclosure) to a target cell (e.g., a target cell in vivo, where the target cell is a target cell in circulation, a target cell in a tissue, a target cell in an organ, etc.) can include a container (e.g., a reservoir, a matrix, etc.) that comprises the polypeptide or nucleic acid (or combinations).

A suitable implantable device can comprise a polymeric substrate, such as a matrix for example, that is used as the device body, and in some cases additional scaffolding materials, such as metals or additional polymers, and materials to enhance visibility and imaging. An implantable delivery device can be advantageous in providing release locally and over a prolonged period, where the polypeptide and/or nucleic acid to be delivered is released directly to a target site, e.g., the extracellular matrix (ECM), the vasculature surrounding a tumor, a diseased tissue, etc. Suitable implantable delivery devices include devices suitable for use in delivering to a cavity such as the abdominal cavity and/or any other type of administration in which the drug delivery system is not anchored or attached, comprising a biostable and/or degradable and/or bioabsorbable polymeric substrate, which may for example optionally be a matrix. In some cases, a suitable implantable drug delivery device comprises degradable polymers, wherein the main release mechanism is bulk erosion. In some cases, a suitable implantable drug delivery device comprises non degradable, or slowly degraded polymers, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the can be maintained effectively constant during a significant period of the total releasing period, and therefore the diffusion rate is effectively constant (termed "zero mode" diffusion). By the term "constant" it is meant a diffusion rate that is maintained above the lower threshold of therapeutic effectiveness, but which may still optionally feature an initial burst and/or may fluctuate, for example increasing and decreasing to a certain degree. The diffusion rate can be so maintained for a prolonged period, and it can be considered constant to a certain level to optimize the therapeutically effective period, for example the effective silencing period.

In some cases, the implantable delivery system is designed to shield a nucleic acid component from degradation, whether chemical in nature or due to attack from enzymes and other factors in the body of the subject.

The site for implantation of the device, or target site, can be selected for maximum therapeutic efficacy. For example, a delivery device can be implanted within or in the proximity of a tumor environment, or the blood supply associated with a tumor. The target location can be, e.g.: 1) the brain at degenerative sites like in Parkinson or Alzheimer disease at the basal ganglia, white and gray matter; 2) the spine, as in the case of amyotrophic lateral sclerosis (ALS); 3) uterine cervix; 4) active and chronic inflammatory joints; 5) dermis as in the case of psoriasis; 7) sympathetic and sensoric nervous sites for analgesic effect; 7) a bone; 8) a site of acute or chronic infection; 9) Intra vaginal; 10) Inner ear—auditory system, labyrinth of the inner ear, vestibular system; 11) Intra tracheal; 12) Intra-cardiac; coronary, epicardiac; 13) urinary tract or bladder; 14) biliary system; 15) parenchymal tissue including and not limited to the kidney, liver, spleen; 16) lymph nodes; 17) salivary glands; 18) dental gums; 19) Intra-articular (into joints); 20) Intra-ocular; 21) Brain tissue; 22) Brain ventricles; 23) Cavities, including abdominal cavity (for example but without limitation, for ovary cancer); 24) Intra esophageal; and 25) Intra rectal; and 26) into the vasculature.

Systems

The present disclosure provides a system for controlling activity of a Cas9 polypeptide. A system of the present disclosure can comprise two or more of: a) an Acr polypeptide of the present disclosure, an Acr fusion polypeptide of the present disclosure, or a modified Acr polypeptide of the present disclosure; b) an RNA comprising a nucleotide sequence encoding an Acr polypeptide of the present disclosure or an Acr fusion polypeptide of the present disclosure; c) a DNA comprising a nucleotide sequence encoding an Acr polypeptide of the present disclosure or an Acr fusion polypeptide of the present disclosure; d) a recombinant expression vector comprising a nucleic acid comprising a nucleotide sequence encoding an Acr polypeptide of the present disclosure or an Acr fusion polypeptide of the present disclosure; e) a Cas9 polypeptide (where the Cas9 polypeptide is one that can be inhibited by an Acr polypeptide of the present disclosure, where such Cas9 polypeptides are described above); f) an RNA comprising a nucleotide sequence encoding a Cas9 polypeptide (where the Cas9 polypeptide is one that can be inhibited by an Acr polypeptide of the present disclosure, where such Cas9 polypeptides are described above); g) a DNA comprising a nucleotide sequence encoding a Cas9 polypeptide (where the Cas9 polypeptide is one that can be inhibited by an Acr polypeptide of the present disclosure, where such Cas9 polypeptides are described above); h) a recombinant expression vector comprising a nucleotide sequence encoding a Cas9 polypeptide (where the Cas9 polypeptide is one that can be inhibited by an Acr polypeptide of the present disclosure, where such Cas9 polypeptides are described above); i) a Cas9 guide RNA; j) a DNA comprising a nucleotide sequence encoding a Cas9 guide RNA; k) a recombinant expression vector comprising a nucleotide sequence encoding a Cas9 guide RNA; l) a recombinant expression vector comprising a nucleotide sequence encoding a constant region (tracRNA region) of a Cas9 guide RNA and an insertion site for inserting a nucleotide sequence encoding a crRNA portion of the Cas9 guide RNA; m) a recombinant expression vector comprising: i) a nucleotide sequence encoding an Acr polypeptide of the present disclosure; and ii) a nucleotide sequence encoding a Cas9 polypeptide (where the Cas9 polypeptide is one that can be inhibited by an Acr polypeptide of the present disclosure, where such Cas9 polypeptides are described above); n) a recombinant expression vector comprising: i) a nucleotide sequence encoding an Acr polypeptide of the present disclosure; and ii) a nucleotide sequence encoding a Cas9 polypeptide (where the Cas9 polypeptide is one that can be inhibited by an Acr polypeptide of the present disclosure, where such Cas9 polypeptides are described above); and iii) a nucleotide sequence encoding a Cas9 guide RNA; o) a host cell of the present disclosure.

In some cases, a system of the present disclosure comprises two or more of: a) recombinant expression vector comprising a nucleotide sequence encoding an Acr polypeptide of the present disclosure (where the recombinant expression vector may optionally include one or both of: i) a nucleotide sequence encoding a Cas9 polypeptide (where the Cas9 polypeptide is one whose activity can be inhibited by the Acr polypeptide); and ii) a nucleotide sequence encoding a Cas9 guide RNA); b) a Cas9 polypeptide (where the Cas9 polypeptide is one whose activity can be inhibited by the Acr polypeptide); c) a recombinant expression vector comprising a nucleotide sequence encoding a Cas9 polypeptide (where the Cas9 polypeptide is one whose activity can be inhibited by the Acr polypeptide); d) an RNA comprising a nucleotide sequence encoding a Cas9 polypeptide (where the Cas9 polypeptide is one whose activity can be inhibited by the Acr polypeptide); d) a Cas9 guide RNA; e) a DNA comprising a nucleotide sequence encoding a Cas9 guide RNA; and f) an Acr polypeptide.

In some cases, a system of the present disclosure comprises: a) an Acr polypeptide of the present disclosure; and b) a Cas9 polypeptide, where the Cas9 polypeptide is one that can be inhibited by the Acr polypeptide. In some cases, a system of the present disclosure comprises: a) an Acr polypeptide of the present disclosure; b) a Cas9 polypeptide, where the Cas9 polypeptide is one that can be inhibited by the Acr polypeptide; and c) a Cas9 guide RNA. In some cases, a system of the present disclosure comprises: a) a recombinant expression vector comprising a nucleotide sequence encoding an Acr polypeptide of the present disclosure; and b) a Cas9 polypeptide, where the Cas9 polypeptide is one that can be inhibited by the Acr polypeptide. In some cases, a system of the present disclosure comprises: a) a recombinant expression vector comprising a nucleotide sequence encoding an Acr polypeptide of the present disclosure; b) a Cas9 polypeptide, where the Cas9 polypeptide is one that can be inhibited by the Acr polypeptide; and c) a Cas9 guide RNA. In some cases, a system of the present disclosure comprises: a) a recombinant expression vector comprising a nucleotide sequence encoding an Acr polypeptide of the present disclosure; b) a recombinant expression vector comprising a nucleotide sequence encoding a Cas9 polypeptide, where the Cas9 polypeptide is one that can be inhibited by the Acr polypeptide; and c) a Cas9 guide RNA. In some cases, a system of the present disclosure comprises: a) a ribonucleoprotein comprising: i) a Cas9 polypeptide, where the Cas9 polypeptide is one that can be inhibited by the Acr polypeptide; and ii) a Cas9 guide RNA; and b) an Acr polypeptide of the present disclosure. In some cases, a system of the present disclosure comprises: a) a ribonucleoprotein comprising: i) a Cas9 polypeptide, where the Cas9 polypeptide is one that can be inhibited by the Acr polypeptide; and ii) a Cas9 guide RNA; and b) a recombinant expression vector comprising a nucleotide sequence encoding an Acr polypeptide of the present disclosure.

Acr Polypeptides

Acr polypeptides that are suitable for inclusion in a system of the present disclosure include: a) Acr polypeptides as described above (including truncated Acr polypeptides as described above); b) Acr fusion polypeptides as described above; and c) modified Acr polypeptides as described above. A system of the present disclosure can comprise an Acr polypeptide of the present disclosure, or a nucleic acid or recombinant expression vector comprising a nucleotide sequence encoding an Acr polypeptide of the present disclosure. A system of the present disclosure can comprise an Acr fusion polypeptide of the present disclosure, or a nucleic acid or recombinant expression vector comprising a nucleotide sequence encoding an Acr fusion polypeptide of the present disclosure. A system of the present disclosure can comprise a modified Acr polypeptide of the present disclosure.

Cas9 Polypeptides

As noted above, in some cases, a system of the present disclosure includes a Cas9 polypeptide, where the Cas9 polypeptide is one that can be inhibited by an Acr polypeptide of the present disclosure, where such Cas9 polypeptides are described above. In some cases, a system of the present disclosure comprises: a) an Acr polypeptide of the present disclosure; and b) a Cas9 polypeptide, where the Cas9 polypeptide is one that can be inhibited by the Acr polypeptide. In some cases, a system of the present disclosure comprises: a) an Acr polypeptide of the present disclosure; b) a Cas9 polypeptide, where the Cas9 polypeptide is one that can be inhibited by the Acr polypeptide; and c) a Cas9 guide RNA.

In some cases, a Cas9 polypeptide included in a system of the present disclosure comprises an amino acid sequence having at least 50%, at least 60%, at least 70%, at least 80%, at least 85%, at least 90%, at least 95%, at least 98%, at least 99%, or 100%, amino acid sequence identity to the *Staphylococcus aureus* Cas9 amino acid sequence provided in FIG. 5.

A *Staphylococcus aureus* Cas9 (SaCas9) suitable for inclusion in a system of the present disclosure can comprise one of the following sets of amino acid substitutions: N419A/R654A, Y211A/R654A, Y211A/Y212A, Y211A/N230A, Y211A/R245A, Y212A/Y230A, Y212A/R245A, Y230A/R245A, W229A/R654A, Y211A/Y212A/Y230A, Y211A/Y212A/R245A, Y211A/Y212A/Y651A, Y211A/Y230A/R245A, Y211A/Y230A/Y651A, Y211A/R245A/Y651A, Y211A/R245A/R654A, Y211A/R245A/N419A, Y211A/N419A/R654A, Y212A/Y230A/R245A, Y212A/Y230A/Y651A, Y212A/R245A/Y651A, Y230A/R245A/Y651A, R245A/N419A/R654A, T392A/N419A/R654A, R245A/T392AN419A/R654A, Y211A/R245A/N419A/R654A, W229A/R245A/N419A/R654A, Y211A/R245A/T392A/N419A/R654A, and Y211A1W229A/R245A/N419A/R654A.

A *Staphylococcus aureus* Cas9 (SaCas9) suitable for inclusion in a system of the present disclosure comprises one of the following amino acid substitutions or sets of amino acid substitutions: E782K; K929R; N968K; R1015H; E782K/N968K/R1015H (KKH variant); E782K/K929R/R1015H (KRH variant); or E782K/K929R/N968K/R1015H (KRKH variant).

Cas9 Guide RNA

A nucleic acid molecule that binds to a Cas9 protein and targets the complex to a specific location within a target nucleic acid is referred to herein as a "Cas9 guide RNA."

A Cas9 guide RNA (can be said to include two segments, a first segment (referred to herein as a "targeting segment"); and a second segment (referred to herein as a "protein-binding segment"). By "segment" it is meant a segment/section/region of a molecule, e.g., a contiguous stretch of nucleotides in a nucleic acid molecule. A segment can also refer to a region/section of a complex such that a segment may comprise regions of more than one molecule.

The first segment (targeting segment) of a Cas9 guide RNA includes a nucleotide sequence (a guide sequence) that is complementary to (and therefore hybridizes with) a specific sequence (a target site) within a target nucleic acid (e.g., a target ssRNA, a target ssDNA, the complementary strand of a double stranded target DNA, etc.). The protein-binding segment (or "protein-binding sequence") interacts with (binds to) a Cas9 polypeptide. The protein-binding segment of a subject Cas9 guide RNA includes two complementary stretches of nucleotides that hybridize to one another to form a double stranded RNA duplex (dsRNA duplex). Site-specific binding and/or cleavage of a target nucleic acid (e.g., genomic DNA) can occur at locations (e.g., target sequence of a target locus) determined by base-pairing complementarity between the Cas9 guide RNA (the guide sequence of the Cas9 guide RNA) and the target nucleic acid.

A Cas9 guide RNA and a Cas9 protein form a complex (e.g., bind via non-covalent interactions). The Cas9 guide RNA provides target specificity to the complex by including a targeting segment, which includes a guide sequence (a nucleotide sequence that is complementary to a sequence of a target nucleic acid). The Cas9 protein of the complex provides the site-specific activity (e.g., cleavage activity or an activity provided by the Cas9 protein when the Cas9 protein is a Cas9 fusion polypeptide, i.e., has a fusion partner). In other words, the Cas9 protein is guided to a target nucleic acid sequence (e.g. a target sequence in a chromosomal nucleic acid, e.g., a chromosome; a target sequence in an extrachromosomal nucleic acid, e.g. an episomal nucleic acid, a minicircle, an ssRNA, an ssDNA, etc.; a target sequence in a mitochondrial nucleic acid; a target sequence in a chloroplast nucleic acid; a target sequence in a plasmid; a target sequence in a viral nucleic acid; etc.) by virtue of its association with the Cas9 guide RNA.

The "guide sequence" also referred to as the "targeting sequence" of a Cas9 guide RNA can be modified so that the Cas9 guide RNA can target a Cas9 protein to any desired sequence of any desired target nucleic acid, with the exception that the protospacer adjacent motif (PAM) sequence is taken into account. Thus, for example, a Cas9 guide RNA can have a targeting segment with a sequence (a guide sequence) that has complementarity with (e.g., can hybridize to) a sequence in a nucleic acid in a eukaryotic cell, e.g., a viral nucleic acid, a eukaryotic nucleic acid (e.g., a eukaryotic chromosome, chromosomal sequence, a eukaryotic RNA, etc.), and the like.

In some embodiments, a Cas9 guide RNA includes two separate nucleic acid molecules: an "activator" and a "targeter" and is referred to herein as a "dual Cas9 guide RNA", a "double-molecule Cas9 guide RNA", or a "two-molecule Cas9 guide RNA" a "dual guide RNA", or a "dgRNA." In some embodiments, the activator and targeter are covalently linked to one another (e.g., via intervening nucleotides) and the guide RNA is referred to as a "single guide RNA", a "Cas9 single guide RNA", a "single-molecule Cas9 guide RNA," or a "one-molecule Cas9 guide RNA", or simply "sgRNA."

A Cas9 guide RNA comprises a crRNA-like ("CRISPR RNA"/"targeter"/"crRNA"/"crRNA repeat") molecule and a corresponding tracrRNA-like ("trans-acting CRISPR RNA"/"activator"/"tracrRNA") molecule. A crRNA-like molecule (targeter) comprises both the targeting segment (single stranded) of the Cas9 guide RNA and a stretch ("duplex-forming segment") of nucleotides that forms one half of the dsRNA duplex of the protein-binding segment of the Cas9 guide RNA. A corresponding tracrRNA-like molecule (activator/tracrRNA) comprises a stretch of nucleotides (duplex-forming segment) that forms the other half of the dsRNA duplex of the protein-binding segment of the guide nucleic acid. In other words, a stretch of nucleotides of a crRNA-like molecule are complementary to and hybridize with a stretch of nucleotides of a tracrRNA-like molecule to form the dsRNA duplex of the protein-binding domain of the Cas9 guide RNA. As such, each targeter molecule can be said to have a corresponding activator molecule (which has a region that hybridizes with the targeter). The targeter molecule additionally provides the targeting segment. Thus, a targeter and an activator molecule (as a corresponding pair) hybridize to form a Cas9 guide RNA. The exact sequence of a given crRNA or tracrRNA molecule is characteristic of the species in which the RNA molecules are found. A subject dual Cas9 guide RNA can include any corresponding activator and targeter pair.

The term "activator" or "activator RNA" is used herein to mean a tracrRNA-like molecule (tracrRNA: "trans-acting CRISPR RNA") of a Cas9 dual guide RNA (and therefore of a Cas9 single guide RNA when the "activator" and the "targeter" are linked together by, e.g., intervening nucleotides). Thus, for example, a Cas9 guide RNA (dgRNA or sgRNA) comprises an activator sequence (e.g., a tracrRNA sequence). A tracr molecule (a tracrRNA) is a naturally existing molecule that hybridizes with a CRISPR RNA molecule (a crRNA) to form a Cas9 dual guide RNA. The term "activator" is used herein to encompass naturally existing tracrRNAs, but also to encompass tracrRNAs with modifications (e.g., truncations, sequence variations, base modifications, backbone modifications, linkage modifications, etc.) where the activator retains at least one function of a tracrRNA (e.g., contributes to the dsRNA duplex to which Cas9 protein binds). In some cases, the activator provides one or more stem loops that can interact with Cas9 protein. An activator can be referred to as having a tracr sequence (tracrRNA sequence) and in some cases is a tracrRNA, but the term "activator" is not limited to naturally existing tracrRNAs.

The term "targeter" or "targeter RNA" is used herein to refer to a crRNA-like molecule (crRNA: "CRISPR RNA") of a Cas9 dual guide RNA (and therefore of a Cas9 single guide RNA when the "activator" and the "targeter" are linked together, e.g., by intervening nucleotides). Thus, for example, a Cas9 guide RNA (dgRNA or sgRNA) comprises a targeting segment (which includes nucleotides that hybridize with (are complementary to) a target nucleic acid, and a duplex-forming segment (e.g., a duplex forming segment of a crRNA, which can also be referred to as a crRNA repeat). Because the sequence of a targeting segment (the segment that hybridizes with a target sequence of a target nucleic acid) of a targeter is modified by a user to hybridize with a desired target nucleic acid, the sequence of a targeter will often be a non-naturally occurring sequence. However, the duplex-forming segment of a targeter (described in more detail below), which hybridizes with the duplex-forming segment of an activator, can include a naturally existing sequence (e.g., can include the sequence of a duplex-forming segment of a naturally existing crRNA, which can also be referred to as a crRNA repeat). Thus, the term targeter is used herein to distinguish from naturally occurring crRNAs, despite the fact that part of a targeter (e.g., the duplex-forming segment) often includes a naturally occurring sequence from a crRNA. However, the term "targeter" encompasses naturally occurring crRNAs.

A Cas9 guide RNA can also be said to include 3 parts: (i) a targeting sequence (a nucleotide sequence that hybridizes with a sequence of the target nucleic acid); (ii) an activator sequence (as described above)(in some cases, referred to as a tracr sequence); and (iii) a sequence that hybridizes to at least a portion of the activator sequence to form a double stranded duplex. A targeter has (i) and (iii); while an activator has (ii).

A Cas9 guide RNA (e.g. a dual guide RNA or a single guide RNA) can be comprised of any corresponding activator and targeter pair. In some cases, the duplex forming segments can be swapped between the activator and the targeter. In other words, in some cases, the targeter includes a sequence of nucleotides from a duplex forming segment of a tracrRNA (which sequence would normally be part of an activator) while the activator includes a sequence of nucleotides from a duplex forming segment of a crRNA (which sequence would normally be part of a targeter).

As noted above, a targeter comprises both the targeting segment (single stranded) of the Cas9 guide RNA and a stretch ("duplex-forming segment") of nucleotides that forms one half of the dsRNA duplex of the protein-binding segment of the Cas9 guide RNA. A corresponding tracrRNA-like molecule (activator) comprises a stretch of nucleotides (a duplex-forming segment) that forms the other half of the dsRNA duplex of the protein-binding segment of the Cas9 guide RNA. In other words, a stretch of nucleotides of the targeter is complementary to and hybridizes with a stretch of nucleotides of the activator to form the dsRNA duplex of the protein-binding segment of a Cas9 guide RNA. As such, each targeter can be said to have a corresponding activator (which has a region that hybridizes with the targeter). The targeter molecule additionally provides the targeting segment. Thus, a targeter and an activator (as a corresponding pair) hybridize to form a Cas9 guide RNA. The particular sequence of a given naturally existing crRNA or tracrRNA molecule is characteristic of the species in which the RNA molecules are found. Examples of suitable activator and targeter are well known in the art.

Targeting Segment of a Cas9 Guide RNA

The first segment of a subject guide nucleic acid includes a guide sequence (i.e., a targeting sequence)(a nucleotide sequence that is complementary to a sequence (a target site) in a target nucleic acid). In other words, the targeting segment of a subject guide nucleic acid can interact with a target nucleic acid (e.g., double stranded DNA (dsDNA)) in a sequence-specific manner via hybridization (i.e., base pairing). As such, the nucleotide sequence of the targeting segment may vary (depending on the target) and can determine the location within the target nucleic acid that the Cas9 guide RNA and the target nucleic acid will interact. The targeting segment of a Cas9 guide RNA can be modified (e.g., by genetic engineering)/designed to hybridize to any desired sequence (target site) within a target nucleic acid (e.g., a eukaryotic target nucleic acid such as genomic DNA).

The targeting segment can have a length of 7 or more nucleotides (nt) (e.g., 8 or more, 9 or more, 10 or more, 12 or more, 15 or more, 20 or more, 25 or more, 30 or more, or 40 or more nucleotides). In some cases, the targeting segment can have a length of from 7 to 100 nucleotides (nt) (e.g., from 7 to 80 nt, from 7 to 60 nt, from 7 to 40 nt, from 7 to 30 nt, from 7 to 25 nt, from 7 to 22 nt, from 7 to 20 nt, from 7 to 18 nt, from 8 to 80 nt, from 8 to 60 nt, from 8 to 40 nt, from 8 to 30 nt, from 8 to 25 nt, from 8 to 22 nt, from 8 to 20 nt, from 8 to 18 nt, from 10 to 100 nt, from 10 to 80 nt, from 10 to 60 nt, from 10 to 40 nt, from 10 to 30 nt, from 10 to 25 nt, from 10 to 22 nt, from 10 to 20 nt, from 10 to 18 nt, from 12 to 100 nt, from 12 to 80 nt, from 12 to 60 nt, from 12 to 40 nt, from 12 to 30 nt, from 12 to 25 nt, from 12 to 22 nt, from 12 to 20 nt, from 12 to 18 nt, from 14 to 100 nt, from 14 to 80 nt, from 14 to 60 nt, from 14 to 40 nt, from 14 to 30 nt, from 14 to 25 nt, from 14 to 22 nt, from 14 to 20 nt, from 14 to 18 nt, from 16 to 100 nt, from 16 to 80 nt, from 16 to 60 nt, from 16 to 40 nt, from 16 to 30 nt, from 16 to 25 nt, from 16 to 22 nt, from 16 to 20 nt, from 16 to 18 nt, from 18 to 100 nt, from 18 to 80 nt, from 18 to 60 nt, from 18 to 40 nt, from 18 to 30 nt, from 18 to 25 nt, from 18 to 22 nt, or from 18 to 20 nt).

The nucleotide sequence (the targeting sequence) of the targeting segment that is complementary to a nucleotide sequence (target site) of the target nucleic acid can have a length of 10 nt or more. For example, the targeting sequence of the targeting segment that is complementary to a target site of the target nucleic acid can have a length of 12 nt or more, 15 nt or more, 18 nt or more, 19 nt or more, or 20 nt or more. In some cases, the nucleotide sequence (the targeting sequence) of the targeting segment that is complementary to a nucleotide sequence (target site) of the target nucleic acid has a length of 12 nt or more. In some cases, the nucleotide sequence (the targeting sequence) of the targeting segment that is complementary to a nucleotide sequence (target site) of the target nucleic acid has a length of 18 nt or more.

For example, the targeting sequence of the targeting segment that is complementary to a target sequence of the target nucleic acid can have a length of from 10 to 100 nucleotides (nt) (e.g., from 10 to 90 nt, from 10 to 75 nt, from 10 to 60 nt, from 10 to 50 nt, from 10 to 35 nt, from 10 to 30 nt, from 10 to 25 nt, from 10 to 22 nt, from 10 to 20 nt, from 12 to 100 nt, from 12 to 90 nt, from 12 to 75 nt, from 12 to 60 nt, from 12 to 50 nt, from 12 to 35 nt, from 12 to 30 nt, from 12 to 25 nt, from 12 to 22 nt, from 12 to 20 nt, from 15 to 100 nt, from 15 to 90 nt, from 15 to 75 nt, from 15 to 60 nt, from 15 to 50 nt, from 15 to 35 nt, from 15 to 30 nt, from 15 to 25 nt, from 15 to 22 nt, from 15 to 20 nt, from 17 to 100 nt, from 17 to 90 nt, from 17 to 75 nt, from 17 to 60 nt, from 17 to 50 nt, from 17 to 35 nt, from 17 to 30 nt, from 17 to 25 nt, from 17 to 22 nt, from 17 to 20 nt, from 18 to 100 nt, from 18 to 90 nt, from 18 to 75 nt, from 18 to 60 nt, from 18 to 50 nt, from 18 to 35 nt, from 18 to 30 nt, from 18 to 25 nt, from 18 to 22 nt, or from 18 to 20 nt). In some cases, the targeting sequence of the targeting segment that is complementary to a target sequence of the target nucleic acid has a length of from 15 nt to 30 nt. In some cases, the targeting sequence of the targeting segment that is complementary to a target sequence of the target nucleic acid has a length of from 15 nt to 25 nt. In some cases, the targeting sequence of the targeting segment that is complementary to a target sequence of the target nucleic acid has a length of from 18 nt to 30 nt. In some cases, the targeting sequence of the targeting segment that is complementary to a target sequence of the target nucleic acid has a length of from 18 nt to 25 nt. In some cases, the targeting sequence of the targeting segment that is complementary to a target sequence of the target nucleic acid has a length of from 18 nt to 22 nt. In some cases, the targeting sequence of the targeting segment that is complementary to a target site of the target nucleic acid is 20 nucleotides in length. In some cases, the targeting sequence of the targeting segment that is complementary to a target site of the target nucleic acid is 19 nucleotides in length.

The percent complementarity between the targeting sequence (guide sequence) of the targeting segment and the target site of the target nucleic acid can be 60% or more (e.g., 65% or more, 70% or more, 75% or more, 80% or more, 85% or more, 90% or more, 95% or more, 97% or more, 98% or more, 99% or more, or 100%). In some cases, the percent complementarity between the targeting sequence of the targeting segment and the target site of the target nucleic acid is 100% over the seven contiguous 5'-most nucleotides of the target site of the target nucleic acid. In some cases, the percent complementarity between the targeting sequence of the targeting segment and the target site of the target nucleic acid is 60% or more over about 20 contiguous nucleotides. In some cases, the percent complementarity between the targeting sequence of the targeting segment and the target site of the target nucleic acid is 100% over the fourteen contiguous 5'-most nucleotides of the target site of the target nucleic acid and as low as 0% or more over the remainder. In such a case, the targeting sequence can be considered to be 14 nucleotides in length. In some cases, the percent complementarity between the targeting sequence of the targeting segment and the target site of the target nucleic acid is 100% over the seven contiguous 5'-most nucleotides of the target site of the target nucleic acid and as low as 0% or more over the remainder. In such a case, the targeting sequence can be considered to be 20 nucleotides in length.

In some cases, the percent complementarity between the targeting sequence of the targeting segment and the target site of the target nucleic acid is 100% over the 7 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 8 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 9 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 10 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 17 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 18 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 60% or more (e.g., e.g., 65% or more, 70% or more, 75% or more, 80% or more, 85% or more, 90% or more, 95% or more, 97% or more, 98% or more, 99% or more, or 100%) over about 20 contiguous nucleotides.

In some cases, the percent complementarity between the targeting sequence of the targeting segment and the target site of the target nucleic acid is 100% over the 7 contiguous 5'-most nucleotides of the target site of the target nucleic acid and as low as 0% or more over the remainder. In such a case, the targeting sequence can be considered to be 7 nucleotides in length. In some cases, the percent complementarity between the targeting sequence of the targeting segment and the target site of the target nucleic acid is 100% over the 8 contiguous 5'-most nucleotides of the target site of the target nucleic acid and as low as 0% or more over the remainder. In such a case, the targeting sequence can be considered to be 8 nucleotides in length. In some cases, the percent complementarity between the targeting sequence of the targeting segment and the target site of the target nucleic acid is 100% over the 9 contiguous 5'-most nucleotides of the target site of the target nucleic acid and as low as 0% or more over the remainder. In such a case, the targeting sequence can be considered to be 9 nucleotides in length. In some cases, the percent complementarity between the targeting sequence of the targeting segment and the target site of the target nucleic acid is 100% over the 10 contiguous 5'-most nucleotides of the target site of the target nucleic acid and as low as 0% or more over the remainder. In such a case, the targeting sequence can be considered to be 10 nucleotides in length. In some cases, the percent complementarity between the targeting sequence of the targeting segment and the target site of the target nucleic acid is 100% over the 11 contiguous 5'-most nucleotides of the target site of the target nucleic acid and as low as 0% or more over the remainder. In such a case, the targeting sequence can be considered to be 11 nucleotides in length. In some cases, the percent complementarity between the targeting sequence of the targeting segment and the target site of the target nucleic acid is 100% over the 12 contiguous 5'-most nucleotides of the target site of the target nucleic acid and as low as 0% or more over the remainder. In such a case, the targeting sequence can be considered to be 12 nucleotides in length. In some cases, the percent complementarity between the targeting sequence of the targeting segment and the target site of the target nucleic acid is 100% over the 13 contiguous 5'-most nucleotides of the target site of the target nucleic acid and as low as 0% or more over the remainder. In such a case, the targeting sequence can be considered to be 13 nucleotides in length. In some cases, the percent complementarity between the targeting sequence of the targeting segment and the target site of the target nucleic acid is 100% over the 14 contiguous 5'-most nucleotides of the target site of the target nucleic acid and as low as 0% or more over the remainder. In such a case, the targeting sequence can be considered to be 14 nucleotides in length. In some cases, the percent complementarity between the targeting sequence of the targeting segment and the target site of the target nucleic acid is 100% over the 17 contiguous 5'-most nucleotides of the target site of the target nucleic acid and as low as 0% or more over the remainder. In such a case, the targeting sequence can be considered to be 17 nucleotides in length. In some cases, the percent complementarity between the targeting sequence of the targeting segment and the target site of the target nucleic acid is 100% over the 18 contiguous 5'-most nucleotides of the target site of the target nucleic acid and as low as 0% or more over the remainder. In such a case, the targeting sequence can be considered to be 18 nucleotides in length.

Examples of various Cas9 proteins and Cas9 guide RNAs (as well as information regarding requirements related to protospacer adjacent motif (PAM) sequences present in targeted nucleic acids) can be found in the art, for example, see Jinek et al., Science. 2012 August 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et al., Genome Res. 2013 Oct. 31; Chen et al., Nucleic Acids Res. 2013 Nov. 1; 41(20):e19; Cheng et al., Cell Res. 2013 October; 23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et al., Nucleic Acids Res. 2013 Nov. 1; 41(20):e187; Hu et al., Cell Res. 2013 November; 23(11):1322-5; Jiang et al., Nucleic Acids Res. 2013 Nov. 1; 41(20):e188; Larson et al., Nat Protoc. 2013 November; 8(11):2180-96; Mali et al., Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; Briner et al., Mol Cell. 2014 Oct. 23; 56(2):333-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

In some cases, a Cas9 guide RNA comprises has one or more modifications, e.g., a base modification, a backbone modification, etc. Suitable nucleic acid modifications include, but are not limited to: 2'O-methyl modified nucleotides, 2' Fluoro modified nucleotides, locked nucleic acid (LNA) modified nucleotides, peptide nucleic acid (PNA) modified nucleotides, nucleotides with phosphorothioate linkages, and a 5' cap (e.g., a 7-methylguanylate cap (m7G)).

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

In some cases, a Cas9 guide RNA comprises a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are $O((CH_2)_nO)_m CH_3$, $O(CH_2)_nOCH_3$, $O(CH_2)_nNH_2$, $O(CH_2)_nCH_3$, $O(CH_2)_n ONH_2$, and $O(CH_2)_nON((CH_2)_nCH_3)_2$, where n and m are from 1 to about 10. Other suitable modifications include a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78, 486-504, the disclosure of which is incorporated herein by reference in its entirety) i.e., an alkoxyalkoxy group. A further suitable modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethylamino-ethoxy-ethyl or 2'-DMAEOE), i.e., 2'-O—$CH_2$—O—$CH_2$—$N(CH_3)_2$.

A subject nucleic acid may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one).

Methods

The present disclosure provides methods of inhibiting activity of a Cas9 polypeptide. The methods generally involve contacting the Cas9 polypeptide with: a) an Acr polypeptide of the present disclosure; b) an Acr fusion polypeptide of the present disclosure; or b) a modified Acr polypeptide of the present disclosure. In some cases, the contacting occurs in a living cell in vitro. In some cases, the contacting occurs in a living cell in vivo. In some cases, the contacting occurs outside of a cell in vivo (e.g., the contacting occurs in an extracellular fluid in vivo). For simplicity, unless stated otherwise, an "Acr polypeptide of the present disclosure" includes an unmodified Acr polypeptide, a variant Acr polypeptide (as described above), a truncated Acr polypeptide (as described above), an Acr fusion polypeptide of the present disclosure, and a modified Acr polypeptide of the present disclosure.

A method of the present disclosure can inhibit binding and/or cleavage activity of a Cas9/guide RNA complex by at least 50%, at least 60%, at least 70%, at least 80%, at least 85%, at least 90%, at least 95%, at least 98%, or at least 99%, compared to the binding and/or cleavage activity of the Cas9/guide RNA complex in the absence of the Acr polypeptide (i.e., where the Cas9/guide RNA complex is not contacted with the Acr polypeptide).

In some cases, a method of the present disclosure comprises introducing into a cell (a "target cell") a nucleic acid (e.g., a recombinant expression vector; an mRNA; and the like) comprising a nucleotide sequence encoding an Acr polypeptide of the present disclosure, where the cell comprises, at the time the Acr-encoding nucleic acid is introduced into the cell, a Cas9 polypeptide (where the Cas9 polypeptide is one that can be inhibited by the Acr polypeptide) or a nucleic acid comprising a nucleotide sequence encoding the Cas9 polypeptide. In some cases, the Acr-encoding nucleotide sequence is integrated into the genome of the cell. In some cases, the Acr-encoding nucleotide sequence is extrachromosomal.

In some cases, a method of the present disclosure comprises introducing into a cell (a "target cell") a nucleic acid (e.g., a recombinant expression vector; an mRNA; and the like) comprising a nucleotide sequence encoding an Acr polypeptide of the present disclosure, where the cell does not comprise, at the time the Acr-encoding nucleic acid is introduced into the cell, a Cas9 polypeptide (where the Cas9 polypeptide is one that can be inhibited by the Acr polypeptide) or a nucleic acid comprising a nucleotide sequence encoding the Cas9 polypeptide. In some cases, the Acr-encoding nucleotide sequence is integrated into the genome of the cell. In some cases, the Acr-encoding nucleotide sequence is extrachromosomal.

In some cases, a method of the present disclosure comprises introducing into a cell (a "target cell") an Acr polypeptide of the present disclosure, where the cell comprises, at the time the Acr polypeptide is introduced into the cell, a Cas9 polypeptide (where the Cas9 polypeptide is one that can be inhibited by the Acr polypeptide) or a nucleic acid comprising a nucleotide sequence encoding the Cas9 polypeptide.

In some cases, a method of the present disclosure comprises introducing into a cell (a "target cell") an Acr polypeptide of the present disclosure, where the cell does not comprise, at the time the Acr polypeptide is introduced into the cell, a Cas9 polypeptide (where the Cas9 polypeptide is one that can be inhibited by the Acr polypeptide) or a nucleic acid comprising a nucleotide sequence encoding the Cas9 polypeptide.

Where a method of the present disclosure comprises introducing into a cell a nucleic acid (e.g., a DNA; a recombinant expression vector; an RNA) comprising a nucleotide sequence encoding an Acr polypeptide of the present disclosure, in some cases, the Acr-encoding nucleotide sequence is operably linked to one or more transcriptional control elements. In some cases, the one or more transcriptional control elements comprises a promoter, e.g., a promoter that is functional in a eukaryotic cell. In some cases, the promoter is a constitutive promoter. In some cases, the promoter is a regulated promoter, e.g., an inducible promoter. In some case, the inducible promoter is a drug-inducible promoter, and the method comprises contacting the cell with a drug that induces the drug-inducible promoter.

In some cases, a method of the present disclosure provides for controlling gene drive. For example, where the gene drive limits viability of a target organism (or target population of an organism), a method of the present disclosure can restore viability to the target organism (or target population of an organism). Examples of target organisms (or target populations of an organism) include ticks (e.g., ticks that carry human pathogens), where ticks include ticks of the families Ixodidae and Argasidae, e.g., *Ixodes ricinus, I. rubicundus, I. scapularis, I. holocyclus*, and *I. pacificus* mites; mosquitoes (e.g., mosquitoes that carry human pathogens such as malaria parasites, Yellow Fever Virus, Dengue virus, Zika virus, Chikungunya virus, and the like), where examples of such mosquitoes include mosquitoes of the genera *Culex, Culistea, Aedes*, or *Anopheles*, e.g., *Aedes aegypti, Aedes albopictus*, and *Anopheles gamiae*; protozoans such as *Plasmodium* species (e.g., *Plasmodium falciparum, Plasmodium vivax, Plasmodium ovale, Plasmodium malariae, Plasmodium berghei, Plasmodium gallinaceum*, and *Plasmodium knowlesi*), nematode species, *Trypanosoma* species, Trichomonadidae species, *Leishmania* species, and the like; insects that are harmful to plants; arthropods that are harmful to plants; and the like.

In some cases, a method of the present disclosure provides for reducing off-target Cas9/guide RNA-mediated gene editing. In some cases, a method of the present disclosure reduces off-target Cas9/guide RNA-mediated gene editing by at least 10%, at least 15%, at least 20%, at least 25%, at least 50%, at least 75%, at least 80%, at least 90%, or more than 95%, compared to the extent of off-target Cas9/guide RNA-mediated gene editing when the Cas9 is not contacted with an Acr polypeptide of the present disclosure.

In some cases, a method of the present disclosure provides protection against deleterious effects of a "hostile" Cas9/guide RNA. For example, an individual can comprise immune cells genetically modified to include an Acr-encoding nucleic acid; if such an individual comes into contact with a hostile Cas9/guide RNA complex that targets immune cells in a deleterious manner, such an individual can be protected from deleterious effects of such a hostile Cas9/guide RNA.

In some cases, an Acr polypeptide of the present disclosure is used to deliver a Cas9 polypeptide to a cell, e.g., a eukaryotic cell. For example, in some cases, a complex of an Acr polypeptide and a Cas9 polypeptide is delivered to a cell. The complex may further include a Cas9 guide RNA and/or a donor template.

Target Nucleic Acids and Cells

An Acr polypeptide of the present disclosure inhibits a Cas9 polypeptide (when the Cas9 polypeptide is complexed with a Cas9 guide RNA) from binding and/or cleaving a target nucleic acid. target nucleic acid can be any nucleic acid (e.g., DNA, RNA), can be double stranded or single stranded, can be any type of nucleic acid (e.g., a chromosome (genomic DNA), derived from a chromosome, chromosomal DNA, plasmid, viral, extracellular, intracellular, mitochondrial, chloroplast, linear, circular, etc.) and can be from any organism (e.g., as long as the Cas9 guide RNA comprises a nucleotide sequence that hybridizes to a target sequence in a target nucleic acid, such that the target nucleic acid can be targeted).

A target nucleic acid (a target of a Cas9/guide RNA complex) can be DNA or RNA. A target nucleic acid can be double stranded (e.g., dsDNA, dsRNA) or single stranded (e.g., ssRNA, ssDNA). In some cases, a target nucleic acid is single stranded. In some cases, a target nucleic acid is a single stranded RNA (ssRNA). In some cases, a target ssRNA (e.g., a target cell ssRNA, a viral ssRNA, etc.) is selected from: mRNA, rRNA, tRNA, non-coding RNA (ncRNA), long non-coding RNA (lncRNA), and microRNA (miRNA). In some cases, a target nucleic acid is a single stranded DNA (ssDNA) (e.g., a viral DNA). As noted above, in some cases, a target nucleic acid is single stranded.

A target nucleic acid can be located anywhere, for example, outside of a cell in vitro, inside of a cell in vitro, inside of a cell in vivo, inside of a cell ex vivo. Suitable target cells (which can comprise target nucleic acids such as genomic DNA) include, but are not limited to: a bacterial cell; an archaeal cell; a cell of a single-cell eukaryotic organism; a plant cell; an algal cell, e.g., *Botryococcus braunii, Chlamydomonas reinhardtii, Nannochloropsis gaditana, Chlorella pyrenoidosa, Sargassum patens, C. agardh*, and the like; a fungal cell (e.g., a yeast cell); an animal cell; a cell from an invertebrate animal (e.g. fruit fly, a cnidarian, an echinoderm, a nematode, etc.); a cell of an insect (e.g., a mosquito; a bee; an agricultural pest; etc.); a cell of an arachnid (e.g., a spider; a tick; etc.); a cell from a vertebrate animal (e.g., a fish, an amphibian, a reptile, a bird, a mammal); a cell from a mammal (e.g., a cell from a rodent; a cell from a human; a cell of a non-human mammal; a cell of a rodent (e.g., a mouse, a rat); a cell of a lagomorph (e.g., a rabbit); a cell of an ungulate (e.g., a cow, a horse, a camel, a llama, a vicuña, a sheep, a goat, etc.); a cell of a marine mammal (e.g., a whale, a seal, an elephant seal, a dolphin, a sea lion; etc.) and the like. Any type of cell may be of interest (e.g. a stem cell, e.g. an embryonic stem (ES) cell, an induced pluripotent stem (iPS) cell, a germ cell (e.g., an oocyte, a sperm, an oogonia, a spermatogonia, etc.), an adult stem cell, a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.).

Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines are maintained for fewer than 10 passages in vitro. Target cells can be unicellular organisms and/or can be grown in culture. If the cells are primary cells, they may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. can be conveniently harvested by biopsy.

Plant cells include cells of a monocotyledon, and cells of a dicotyledon. The cells can be root cells, leaf cells, cells of the xylem, cells of the phloem, cells of the cambium, apical meristem cells, parenchyma cells, collenchyma cells, sclerenchyma cells, and the like. Plant cells include cells of agricultural crops such as wheat, corn, rice, sorghum, millet, soybean, etc. Plant cells include cells of agricultural fruit and nut plants, e.g., plant that produce apricots, oranges, lemons, apples, plums, pears, almonds, etc.

Additional examples of target cells are listed above in the section titled "Modified cells." Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatoes, rice, cassava, sugarcane, pumpkin, hay, potatoes, cotton, cannabis, tobacco, flowering plants, conifers, gymnosperms, angiosperms, ferns, clubmosses, hornworts, liverworts, mosses, dicotyledons, monocotyledons, etc.), an algal cell, (e.g., *Botryococcus braunii, Chlamydomonas reinhardtii, Nannochloropsis gaditana, Chlorella pyrenoidosa, Sargassum patens, C. agardh*, and the like), seaweeds (e.g. kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep); a rodent (e.g., a rat, a mouse); a non-human primate; a human; a feline (e.g., a cat); a canine (e.g., a dog); etc.), and the like. In some cases, the cell is a cell that does not originate from a natural organism (e.g., the cell can be a synthetically made cell; also referred to as an artificial cell).

A cell can be an in vitro cell (e.g., established cultured cell line). A cell can be an ex vivo cell (cultured cell from an individual). A cell can be and in vivo cell (e.g., a cell in an individual). A cell can be an isolated cell. A cell can be a cell inside of an organism. A cell can be an organism. A cell can be a cell in a cell culture (e.g., in vitro cell culture). A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbe cell or derived from a microbe cell. A cell can be a fungi cell or derived from a fungi cell. A cell can be an insect cell. A cell can be an arthropod cell. A cell can be a protozoan cell. A cell can be a helminth cell.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, adult cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell.

Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some embodiments, the stem cell is a hematopoietic stem cell (HSC). HSCs are mesoderm-derived cells that can be isolated from bone marrow, blood, cord blood, fetal liver and yolk sac. HSCs are characterized as CD34+ and CD3−. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other embodiments, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other embodiments, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

A cell is in some cases a plant cell. A plant cell can be a cell of a monocotyledon. A cell can be a cell of a dicotyledon.

In some cases, the cell is a plant cell. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (rappini), brussels sprouts, cabbage, cabbage sprouts, cactus leaf (nopales), calabaza, cardoon, carrots, cauliflower, celery, chayote, chinese artichoke (crosnes), chinese cabbage, chinese celery, chinese chives, choy sum, chrysanthemum leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf—green), lettuce (oak leaf—red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, salicornia (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams (names), yu choy, yuca (cassava), and the like.

A cell is in some cases an arthropod cell. For example, the cell can be a cell of a sub-order, a family, a sub-family, a group, a sub-group, or a species of, e.g., *Chelicerata, Myriapodia, Hexipodia, Arachnida, Insecta, Archaeognatha, Thysanura, Palaeoptera, Ephemeroptera, Odonata, Anisoptera, Zygoptera, Neoptera, Exopterygota, Plecoptera, Embioptera, Orthoptera, Zoraptera, Dermaptera, Dictyoptera, Notoptera, Grylloblattidae, Mantophasmatidae, Phasmatodea, Blattaria, Isoptera, Mantodea, Parapneuroptera, Psocoptera, Thysanoptera, Phthiraptera, Hemiptera, Endopterygota* or *Holometabola, Hymenoptera, Coleoptera, Strepsiptera, Raphidioptera, Megaloptera, Neuroptera, Mecoptera, Siphonaptera, Diptera, Trichoptera*, or *Lepidoptera*.

A cell is in some cases an insect cell. For example, in some cases, the cell is a cell of a mosquito, a grasshopper, a true bug, a fly, a flea, a bee, a wasp, an ant, a louse, a moth, or a beetle.

Kits

The present disclosure provides a kit comprising an Acr polypeptide of the present disclosure or a nucleic acid (e.g., a recombinant expression vector) comprising a nucleotide sequence encoding an Acr polypeptide of the present disclosure. The present disclosure provides a kit comprising an Acr system of the present disclosure or a component of an Acr system of the present disclosure.

A kit of the present can comprise: a) any combination of an Acr system, as described above; b) and one or more additional components and/or reagents, e.g., i) a buffer; ii) a protease inhibitor; iii) a nuclease inhibitor; iv) a positive and/or negative control target DNA; v) a positive and/or negative control Cas9 guide RNA; and the like.

In some cases, a kit of the present disclosure comprises: a) a Cas9 polypeptide comprising an amino acid sequence having at least 70% amino acid sequence identity to the amino acid sequence depicted in FIG. 5, or a nucleic acid comprising a nucleotide sequence encoding the Cas9 polypeptide; and b) an Acr polypeptide that is an inhibitor of an activity of the Cas9 polypeptide, wherein the Acr polypeptide comprises an amino acid sequence having at least 70% (at least 70%, at least 85%, at least 80%, at least 85%, at least 90%, at least 95%, at least 98%, or 100%) amino acid sequence identity to the amino acid sequence set forth in any one of SEQ ID NOs:1-4, or a nucleic acid comprising a nucleotide sequence encoding the Acr polypeptide, wherein the enzymatic activity is nucleic acid cleavage.

In some cases, a kit of the present disclosure comprises:
a) a Cas9 polypeptide comprising an amino acid sequence having at least 70% amino acid sequence identity to the amino acid sequence depicted in FIG. 5, or a nucleic acid comprising a nucleotide sequence encoding the Cas9 polypeptide; and b) i) an Acr polypeptide that is an inhibitor of an activity of the Cas9 polypeptide; or ii) an Acr fusion polypeptide of the present disclosure; or iii) a modified Acr polypeptide of the present disclosure, wherein the Acr polypeptide (or the Acr polypeptide present in the fusion polypeptide, or the modified Acr polypeptide)) comprises an amino acid sequence having at least 70% amino acid sequence identity to the amino acid sequence set forth in any one of SEQ ID NOs:1-4; or iv) a nucleic acid comprising a nucleotide sequence encoding the Acr polypeptide; or v) a nucleic acid comprising a nucleotide sequence encoding the Acr fusion polypeptide, wherein the enzymatic activity is nucleic acid cleavage.

A kit of the present disclosure can also include a positive control and/or a negative control. For example, a suitable control for a protein that inhibits SpyCas9-mediated, but not SauCas9-mediated, cleavage of a target nucleic acid is AcrIIA4. A suitable control for a protein that inhibits both SpyCas9-mediated and SauCas9-mediated cleavage of a target nucleic acid is AcrIIA5.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-58 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A fusion polypeptide comprising: a) anti-CRISPR (Acr) polypeptide that is an inhibitor of an enzymatic activity of a Cas9 polypeptide, wherein the Acr polypeptide comprises an amino acid sequence having at least 70% amino acid sequence identity to the amino acid sequence set forth any one of SEQ ID NOs:1-4; and b) a heterologous fusion partner.

Aspect 2. The fusion polypeptide of aspect 1, wherein the heterologous fusion partner is a nuclear localization sequence.

Aspect 3. The fusion polypeptide of aspect 1, wherein the heterologous fusion partner is an epitope tag.

Aspect 4. The fusion polypeptide of any one of aspects 1-3, wherein the Acr polypeptide lacks the 54-64 amino-terminal amino acids of the amino acid sequence set forth in SEQ ID NO:1; and wherein the Acr polypeptide has a length of from 95 amino acids to 105 amino acids.

Aspect 5. The fusion polypeptide of any one of aspects 1-3, wherein the Acr polypeptide lacks the 51-61 amino-terminal amino acids of the amino acid sequence set forth in SEQ ID NO:2; and wherein the Acr polypeptide has a length of from 109 amino acids to 119 amino acids.

Aspect 6. A nucleic acid comprising a nucleotide sequence encoding the fusion polypeptide of any one of aspects 1-4.

Aspect 7. The nucleic acid of aspect 6, wherein the nucleotide sequence is operably linked to a promoter.

Aspect 8. A recombinant expression vector comprising the nucleic acid of aspect 6 or aspect 7.

Aspect 9. A cell comprising the nucleic acid of aspect 6 or aspect 7, or the recombinant expression vector of aspect 8.

Aspect 10. The cell of aspect 9, wherein the cell is a eukaryotic cell.

Aspect 11. The cell of aspect 9 or aspect 10, wherein the cell is in vitro.

Aspect 12. The cell of aspect 9 or aspect 10, wherein the cell is in vivo.

Aspect 13. A modified anti-CRISPR (Acr) polypeptide comprising:
a) an Acr polypeptide that is an inhibitor of an enzymatic activity of a Cas9 polypeptide, wherein the Acr polypeptide comprises an amino acid sequence having at least 70% amino acid sequence identity to the amino acid sequence set forth in any one of SEQ ID NOs:1-4; and
b) a non-peptidic moiety covalently linked to the Acr polypeptide.

Aspect 14. The modified Acr polypeptide of aspect 13, wherein the non-peptidic moiety provides for one or more of an increase in in vivo half-life, in vivo stability, and bioavailability of the Acr polypeptide, compared to the unmodified Acr polypeptide.

Aspect 15. The modified Acr polypeptide of aspect 13 or aspect 14, wherein the non-peptidic moiety comprises poly (ethylene glycol).

Aspect 16. A recombinant expression vector comprising a nucleotide sequence encoding an anti-CRISPR (Acr) polypeptide that is an inhibitor of an enzymatic activity of a Cas9 polypeptide, wherein the Acr polypeptide comprises an amino acid sequence having at least 70% amino acid sequence identity to the amino acid sequence set forth in any one of SEQ ID NOs:1-4.

Aspect 17. The recombinant expression vector of aspect 16, wherein the Acr polypeptide-encoding nucleotide sequence is operably linked to a promoter.

Aspect 18. The recombinant expression vector of aspect 17, wherein the promoter is functional in a eukaryotic cell.

Aspect 19. The recombinant expression vector of aspect 17 or aspect 18, wherein the promoter is a regulated promoter.

Aspect 20. The recombinant expression vector of aspect 19, wherein the regulated promoter is an inducible promoter.

Aspect 21. The recombinant expression vector of aspect 20, wherein the inducible promoter is a heat-inducible promoter, a drug-inducible promoter, an alcohol-inducible promoter, a hormone-inducible promoter, a steroid-inducible promoter, or a metal-inducible promoter.

Aspect 22. The recombinant expression vector of aspect 17, wherein the promoter is a tissue-specific promoter or a cell type-specific promoter.

Aspect 23. The recombinant expression vector of any one of aspects 16-22, further comprising a nucleotide sequence encoding a guide RNA that binds to and activates a Cas9 polypeptide.

Aspect 24. The recombinant expression vector of any one of aspects 15-22, wherein the recombinant expression vector is a recombinant viral vector.

Aspect 25. A cell comprising the recombinant expression vector of any one of aspects 16-24.

Aspect 26. The cell of aspect 25, wherein the cell is in vitro.

Aspect 27. The cell of aspect 25, wherein the cell is in vivo.

Aspect 28. The cell of any one of aspects 24-27, wherein the cell is a eukaryotic cell.

Aspect 29. The cell of aspect 28, wherein the cell is a mammalian cell, an insect cell, a plant cell, an arthropod cell, a helminth cell, a protozoan cell, a reptile cell, an avian cell, an amphibian cell, a fungal cell, an algal cell, or a fish cell.

Aspect 30. A nucleic acid comprising:
a) a first nucleotide sequence encoding the constant region of a guide RNA;
b) a second nucleotide sequence encoding a Cas9 polypeptide; and
c) a third nucleotide sequence encoding an anti-CRISPR (Acr) polypeptide that is an inhibitor of the Cas9 polypeptide, wherein the Acr polypeptide comprises an amino acid sequence having at least 70% amino acid sequence identity to the amino acid sequence set forth in any one of SEQ ID NOs:1-4.

Aspect 31. The nucleic acid of aspect 30, comprising an insertion site for inserting a nucleotide sequence encoding a guide sequence of the guide RNA, wherein the insertion site is 5' of and immediately adjacent to first nucleotide sequence.

Aspect 32. The nucleic acid of aspect 30, comprising a nucleotide sequence encoding a guide sequence of the guide RNA, wherein the guide sequence-encoding nucleotide sequence is 5' of and immediately adjacent to first nucleotide sequence.

Aspect 33. The nucleic acid of any one of aspects 30-32, wherein the Cas9 polypeptide comprises an amino acid sequence having at least 70% amino acid sequence identity to the amino acid sequence depicted in FIG. 5.

Aspect 34. The nucleic acid of any one of aspects 30-33, wherein the third nucleotide sequence is operably linked to a promoter.

Aspect 35. The nucleic acid of aspect 34, wherein the promoter is functional in a eukaryotic cell.

Aspect 36. The nucleic acid of aspect 33 or aspect 34, wherein the promoter is an inducible promoter.

Aspect 37. The nucleic acid of aspect 36, wherein the inducible promoter is a heat-inducible promoter, a drug-inducible promoter, an alcohol-inducible promoter, a hormone-inducible promoter, a steroid-inducible promoter, or a metal-inducible promoter.

Aspect 38. The nucleic acid of aspect 34 or 35, wherein the promoter is a tissue-specific promoter or a cell type-specific promoter.

Aspect 39. A recombinant expression vector comprising the nucleic acid of any one of aspects 30-38.

Aspect 40. A cell comprising the nucleic acid of any one of aspects 30-38 or the recombinant expression vector of aspect 39.

Aspect 41. The cell of aspect 40, wherein the cell is in vitro.

Aspect 42. The cell of aspect 40, wherein the cell is in vivo.

Aspect 43. The cell of any one of aspects 40-42, wherein the cell is a eukaryotic cell.

Aspect 44. The cell of aspect 43, wherein the cell is a mammalian cell, an insect cell, a plant cell, an arthropod cell, a helminth cell, a protozoan cell, a reptile cell, an avian cell, an amphibian cell, a fungal cell, an algal cell, or a fish cell.

Aspect 45. A nucleic acid comprising a nucleotide sequence encoding an anti-CRISPR (Acr) polypeptide that is an inhibitor of an enzymatic activity of a Cas9 polypeptide, wherein the Acr polypeptide comprises an amino acid sequence having at least 70% amino acid sequence identity to the amino acid sequence set forth in any one of SEQ ID NOs:1-4, and wherein the nucleotide sequence is optimized for expression in a mammalian cell.

Aspect 46. The nucleic acid of aspect 45, wherein the nucleotide sequence is operably linked to a promoter.

Aspect 47. A recombinant expression vector comprising the nucleic acid of aspect 45 or aspect 46.

Aspect 48. A kit comprising:
a) a Cas9 polypeptide comprising an amino acid sequence having at least 70% amino acid sequence identity to the SauCas9 amino acid sequence depicted in FIG. 5, or a nucleic acid comprising a nucleotide sequence encoding the Cas9 polypeptide; and
b) an anti-CRISPR (Acr) polypeptide that is an inhibitor of an activity of the Cas9 polypeptide, wherein the Acr polypeptide comprises an amino acid sequence having at least 70% amino acid sequence identity to the amino acid sequence set forth in any one of SEQ ID NOs:1-4, or a nucleic acid comprising a nucleotide sequence encoding the Acr polypeptide, wherein the enzymatic activity is nucleic acid cleavage.

Aspect 49. The kit of aspect 48, wherein component (a) and component (b) are in separate containers.

Aspect 50. A method for inhibiting an activity of a Cas9 polypeptide, the method comprising contacting the Cas9 polypeptide with:
a) an anti-CRISPR (Acr) polypeptide comprising an amino acid sequence having at least 70% amino acid sequence identity to the amino acid sequence set forth in any one of SEQ ID NOs:1-4; or
b) the Acr fusion polypeptide of any one of aspects 1-5.

Aspect 51. The method of aspect 50, wherein the Cas9 polypeptide comprises an amino acid sequence having at least 70% amino acid sequence identity to the amino acid sequence depicted in FIG. 5.

Aspect 52. The method of aspect 50 or 51, wherein said contacting occurs in a living cell in vitro.

Aspect 53. The method of aspect 50 or 51, wherein said contacting occurs in a living cell in vivo.

Aspect 54. The method of aspect 52 or aspect 53, comprising introducing into the cell a nucleic acid comprising a nucleotide sequence encoding the Acr polypeptide.

Aspect 55. The method of any one of aspects 52-54, wherein the nucleotide sequence encoding the Acr polypeptide is operably linked to an inducible promoter.

Aspect 56. The method of any one of aspects 52-55, wherein the cell is a eukaryotic cell.

Aspect 57. The method of aspect 56, wherein the cell is a mammalian cell, an insect cell, a plant cell, an arthropod cell, a helminth cell, a protozoan cell, a reptile cell, an avian cell, an amphibian cell, a fungal cell, an algal cell, or a fish cell.

Aspect 58. The method of aspect 55, wherein the inducible promoter is a drug-inducible promoter, and wherein the method comprises contacting the cell with a drug that induces the drug-inducible promoter.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Identification of Acrs

Figure 7:
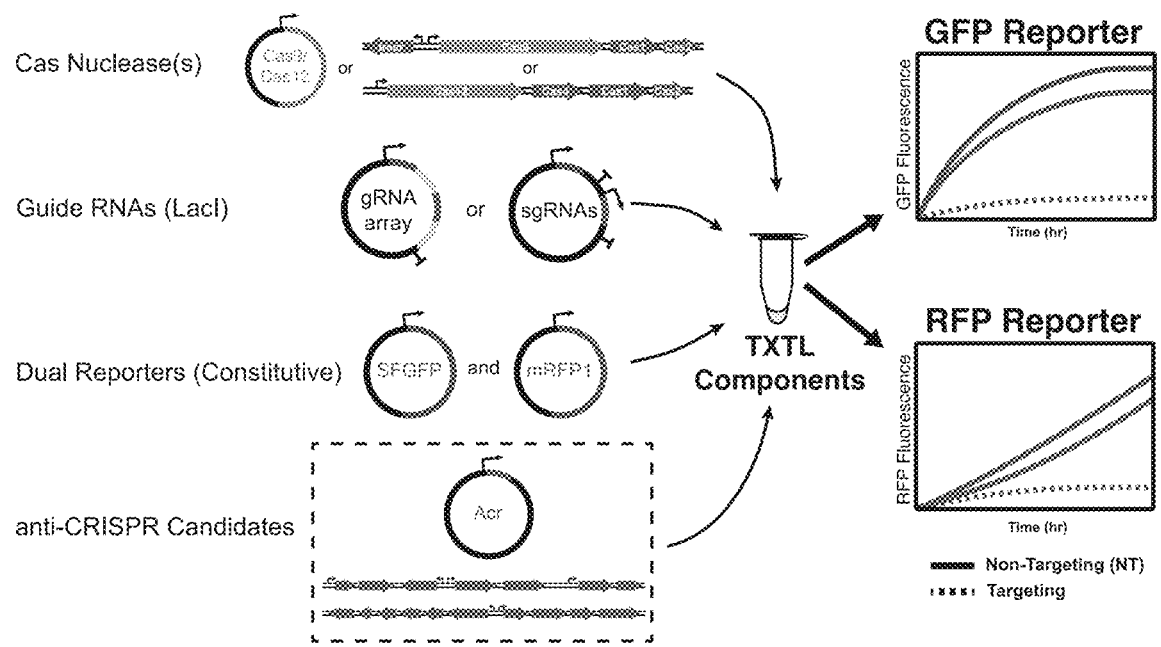
FIG. 7 is a schematic depiction of an assay used to identify proteins having anti-CRISPR/Cas9 activity.

To determine whether a test protein was an Acr (i.e., exhibited inhibitory activity toward a Cas9 protein), a cell-free transcription-translation system, as depicted schematically in FIG. 7, was used. Essentially, a reporter pair (e.g., two fluorescent proteins, such as green fluorescent protein (GFP) and red fluorescent protein (RFP) that is transcribed and translated over time was used. A Cas9 protein and gRNAs targeting the reporters were used to cleave the reporters, thereby reducing the fluorescence levels produced by the reporters. Shown in the illustrations for both the GFP and RFP reporters are two increasing fluorescence traces with solid lines, in which one experimental set up lacks a guide RNA and the other lacks a Cas9/guide RNA complex. Successful cleavage activity would reduce the fluorescent signal (dashed line). In this cell-free system (Arbor Biosciences, myTXTL®), expression of the guide RNAs was controlled by an inducible Lad promoter. When linear DNA or plasmid DNA encoding a test protein was included, cleavage of the reporter was reduced, and therefore the fluorescence remained high, if the test protein inhibited the Cas9.

Two Acrs were identified: Aca cand9 and Aca cand27.

The Acr proteins were purified and tested for their ability to inhibit *Staphylococcus aureus* Cas9 (SauCas9)- or *Streptococcus pyogenes* Cas9 (SpyCas9)-mediated cleavage of a target nucleic acid in vitro.

The following guide RNAs (gRNA) can be used, together with Sau Cas9 or Spy Cas9, to target the Cas9 to enhanced GFP (eGFP):

SauCas9 gRNA (targets eGFP in human cells) gcaagggcgaggagctgttcacGTTTTAGTACTCTGGAAAC-AGAATCTACTAAAACAAG GCAAAATGCCGTGTT-TATCTCGTCAACTTGTTGGCGAGATTTTT (SEQ ID NO:42); and SpyCas9 crRNA (targets eGFP in human cells, part of the Alt-R® CRISPR-Cas9 system (Integrated DNA Technology (IDT)), which pairs with tracrRNA) ctgaagttcatctgcaccacGTTTTAGAGCTATCT (SEQ ID NO:43).

Example 2: Characterization of Aca cand9 and Aca cand27

Inhibition of *S. aureus* Cas9 ("SauCas9") by Acrs AcrIIA5, Aca Cand9, and Aca Cand27 at various ratios of Acr to SauCas9 was tested. AcrIIA5 inhibits both *S. pyogenes* Cas9 and *S. aureus* Cas9. Hynes et al. (2017) Nat. Microbiol. 2:1374. The data are shown in FIG. 1. As shown in FIG. 1, Aca Cand9 and Aca Cand27 inhibited SauCas9-mediated cleavage of target DNA at Acr:SauCas9 molar ratios of 10:1 and 20:1.

Figure 2:
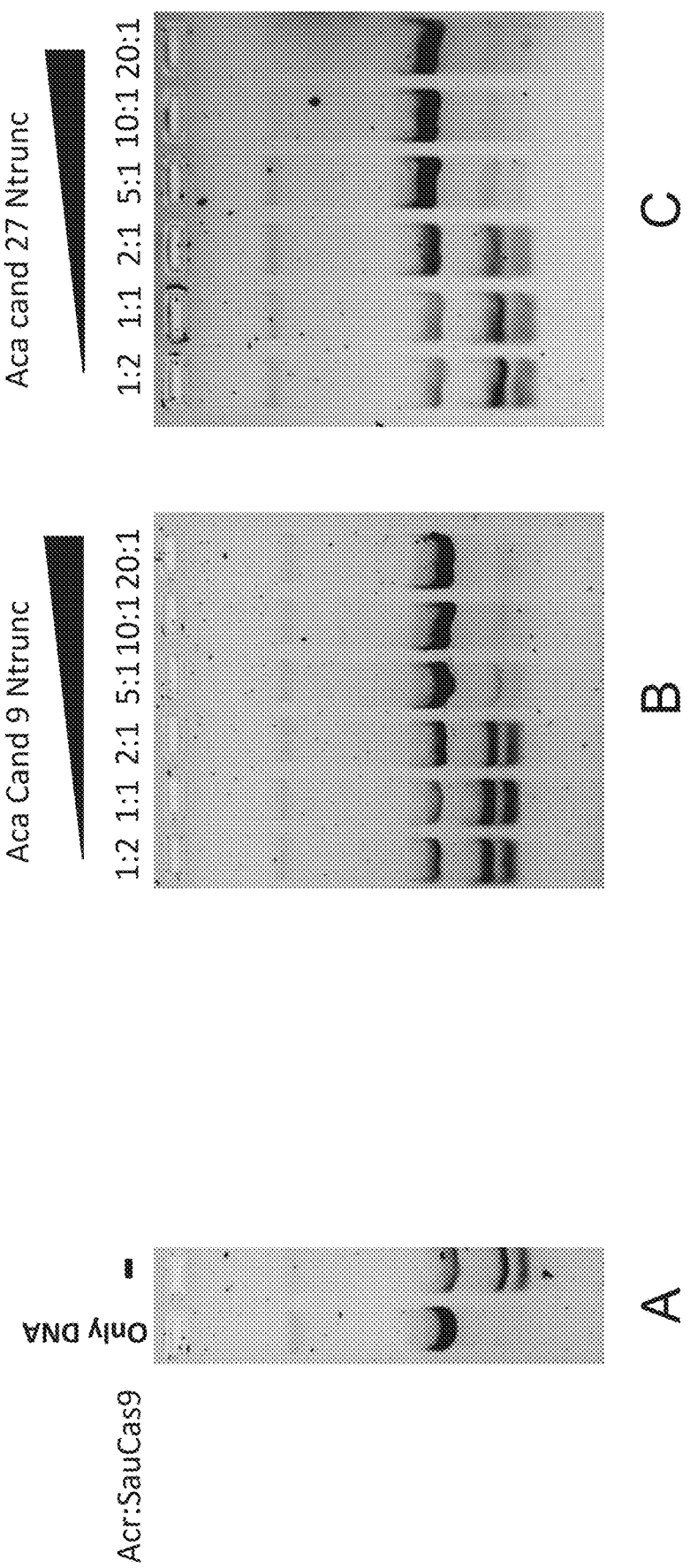
FIG. 2 depicts the effect of truncated forms of Acr proteins Aca Cand9 and Aca Cand2 on SauCas9/guide RNA-mediated cleavage of a target nucleic acid at various molar ratios of truncated Acr:SauCas9 in vitro.

The effect of removal of the N-terminal 59 amino acids from Aca cand9, and the effect of removal of the N-terminal 56 amino acids from Aca cand27, on inhibition of SauCas9 was tested. The results are shown in FIG. 2A-2C. FIG. 2A shows the target DNA alone ("only DNA") and the cleavage observed using SauCas9 without any Acr ("-"). Various ratios of truncated Acr:SauCas9 were tested. As shown in FIG. 2, truncated Aca cand9 (FIG. 2B) and truncated Aca cand27 (FIG. 2C) inhibited SauCas9/guide RNA-mediated cleavage of target DNA at truncated Acr:SauCas9 molar ratios of 5:1, 10:1, and 20:1.

Figure 3:
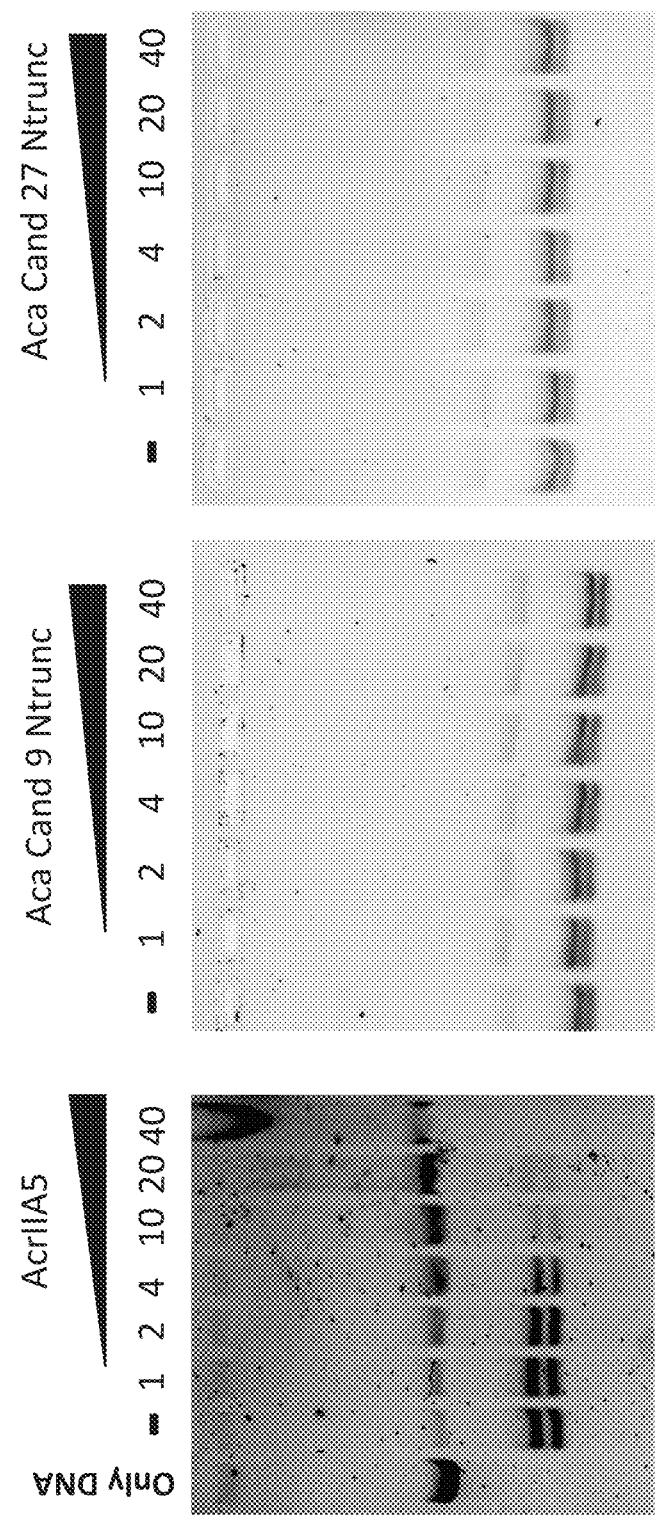
FIG. 3 depicts the effect of a truncated forms of Acr proteins Aca Cand9 and Aca Cand2, compared to AcrIIA5, on SpyCas9/guide RNA-mediated cleavage of a target nucleic acid at various molar fold excess of Acr over SpyCas9.

The truncated forms of Aca Cand9 and Aca Cand27 did not inhibit *S. pyogenes* Cas9 (SpyCas9). The data are shown in FIG. 3A-3C. The truncated forms of Aca Cand9 and Aca Cand27 were incubated with SpyCas9 at the indicated fold molar excess of truncated Acr over SpyCas9. FIG. 3A depicts SphCas9 inhibition with AcrIIA5 at 10-, 20-, and 40-fold molar excess of inhibitor. FIG. 3B and FIG. 3C show the activity of SpyCas9 in the presence of either Aca Cand9 Ntrunc (FIG. 3B) or Aca Cand 27 Ntrunc (FIG. 3C). As shown in FIGS. 3B and 3C, neither truncated Aca cand9 nor truncated Aca cand27 inhibited SpyCas9/guide RNA-mediated cleavage of target DNA, even at 40-fold molar excess over SpyCas9.

Figure 4:
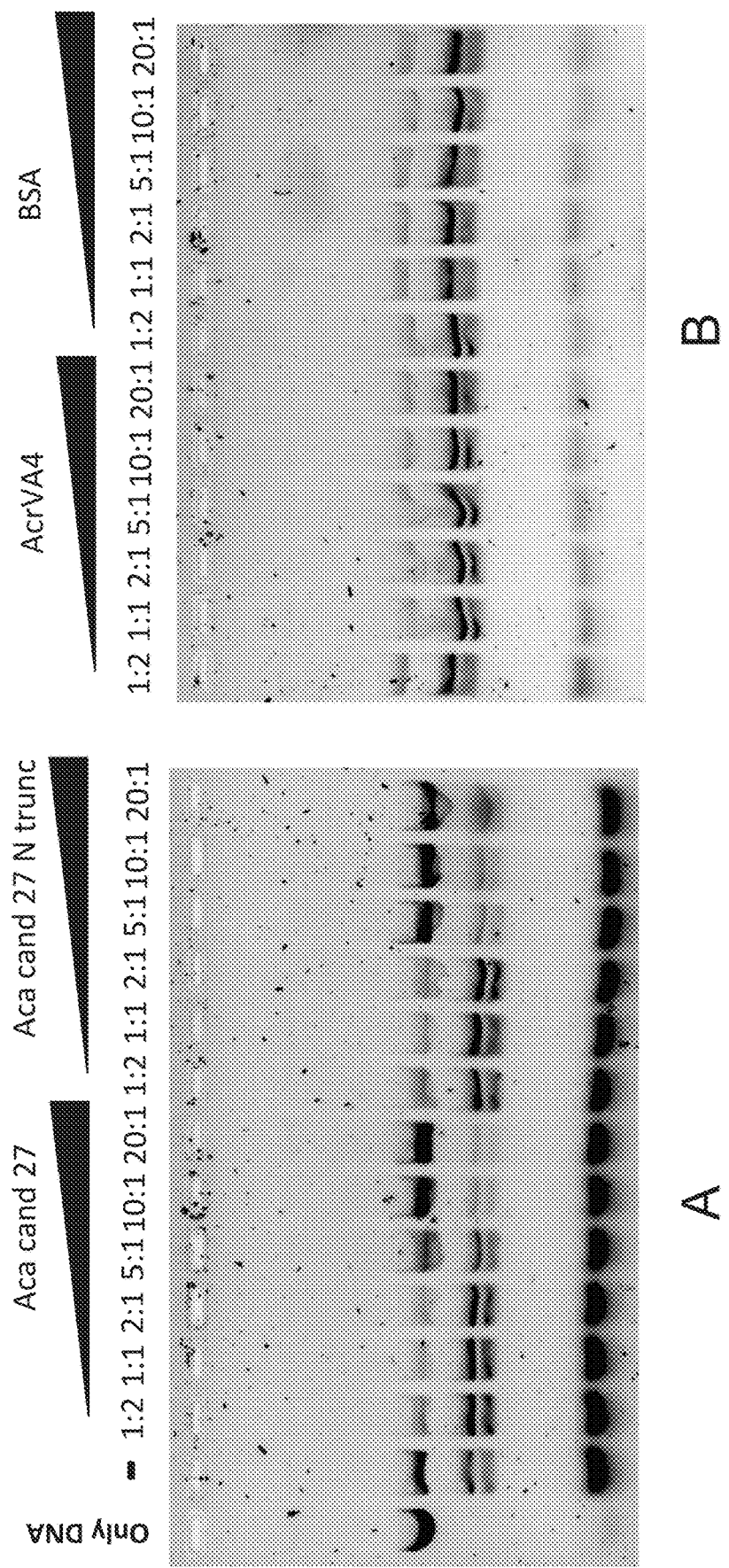
FIG. 4 depicts the effect of: i) full-length Acr protein Aca cand27; ii) a truncated form of Acr protein Aca cand27; and iii) AcrVA4, on SauCas9/guide RNA-mediated cleavage of a target nucleic acid at various ratios of Acr:SauCas9. Bovine serum albumin (BSA) is also provided as a negative control.

FIG. 4A-4B provide a comparison of the effect on Sau-Cas9/guide RNA-mediated cleavage of target DNA of: i) full-length Aca cand27; ii) truncated Aca cand 27; iii) AcrVA4; and iv) bovine serum albumin (BSA) at various molar ratios of protein (Acr or BSA) to SauCas9. As shown in FIG. 4A, both Aca Cand 27 and Aca Cand 27 Ntrunc were active at molar ratios from approximately 5:1 to 20:1 of inhibitor: SauCas9. FIG. 4B depicts the SauCas9 activity in the presence of AcrVA4 (known to inhibit Cas12a) or BSA, demonstrating that neither of these proteins inhibits Sau-Cas9/guide RNA complex mediated cleavage.

Example 3: Activity of Aca Cand 9, Aca Cand 9 N-trunc, Aca Cand27, and Aca Cand27 N-trunc in Mammalian Cells The effects of the anti-CRISPR proteins were determined in HEK-293 cells comprising an inducible GFP reporter. In brief, a human HEK-293T cell line (HEK-RT1) was constructed comprising a stably integrated lentiviral vector encoding GFP under the control of a doxycycline-inducible promoter. SauCas9 or SpyCas9 and their respective GFP-targeting guides were expressed from stably integrated lentiviral vectors. Cas9 cleavage activity was indicated by disruption of GFP expression: a decrease in GFP expression indicated cleavage of the GFP gene by the Cas9/guide RNA complex.

Figure 8:
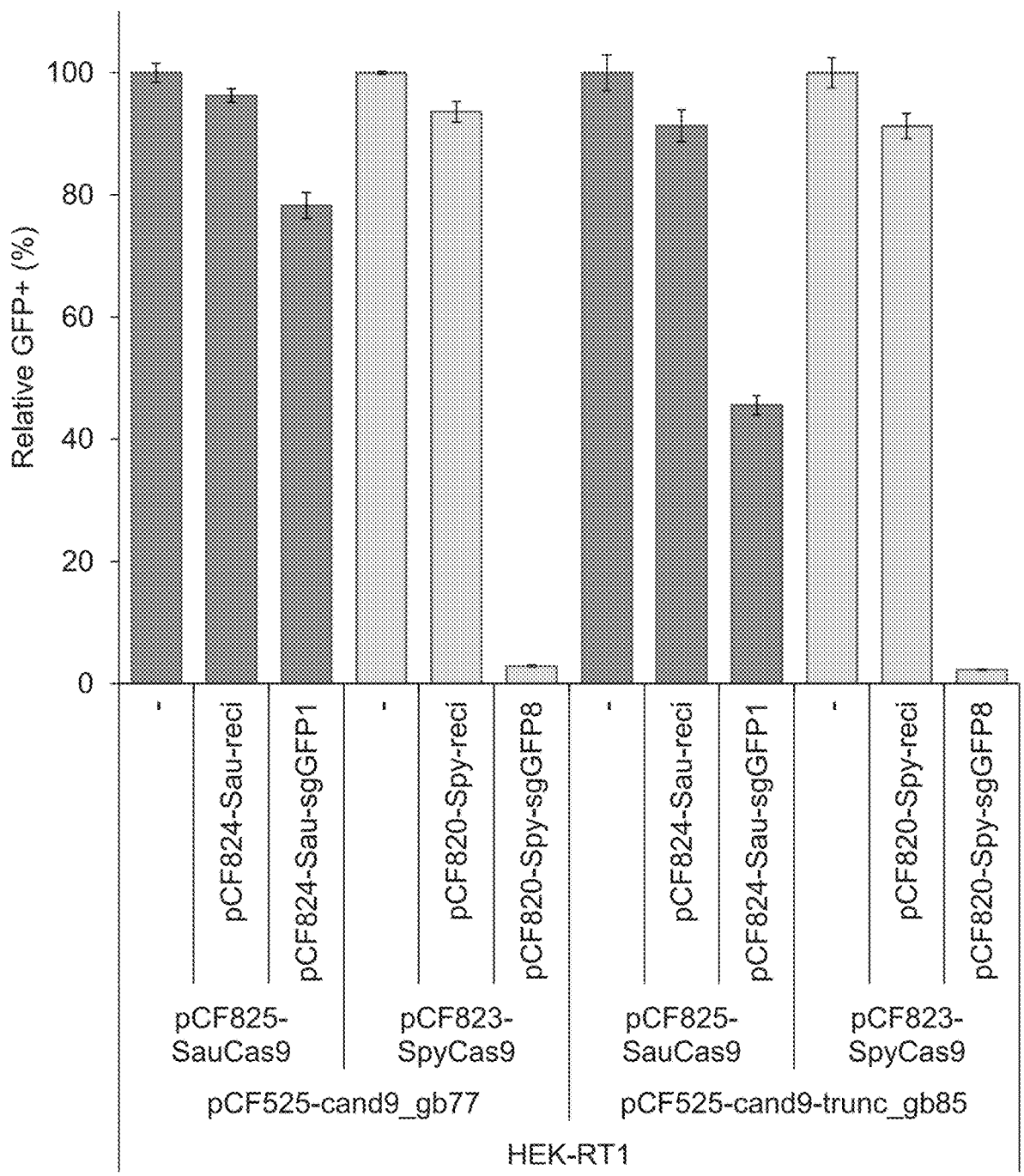
FIG. 8 depicts the effect of Aca cand9 and Aca cand9 Ntrunc on SauCas9/guide RNA activity or on SpyCas9/guide RNA activity in a human cell line.

The results for Aca cand9 are presented in FIG. 8. The first 6 bars indicate the activity with the full-length Aca cand9 protein (also referred to as gb77) and the last 6 bars show the results with the Aca cand9-N-trunc protein (also referred to as gb85). The first three bars indicate the results in the presence of an integrated lentivirus expressing SauCas9 (pCF825-SauCas9), while bars 4-6 represent the results in the presence of an integrated lentivirus expressing SpyCas9 (pCF823-SpyCas9). The lane in both of these datasets marked "-" indicates the results without any guide RNA. "pCF824-Sau-reci" indicates a SauCas9-specific guide targeting an irrelevant target and "pCG824-Sau-sgGFP1" indicates the results with a SauCas9-specific guide targeting GFP. "pCF820-Spy-reci" indicates a SpyCas9-specific guide targeting an irrelevant (control) target and "pCF820-Spy-sgGFP8" indicates the results with a SpyCas9-specific guide targeting GFP. The results demonstrate that Aca cand9 inhibits a SauCas9/guide RNA complex from cleaving the GFP reporter. Activity of the SpyCas9/guide RNA complex was not inhibited by Aca cand9. Bars 7-12 depict the results from a similar experimental set up using the Aca cand9-Ntrunc inhibitor, demonstrating that the truncated form of Aca cand9 inhibits SauCas9/guide RNA, but not SpyCas9/guide RNA from cleaving the target nucleic acid.

Figure 9:
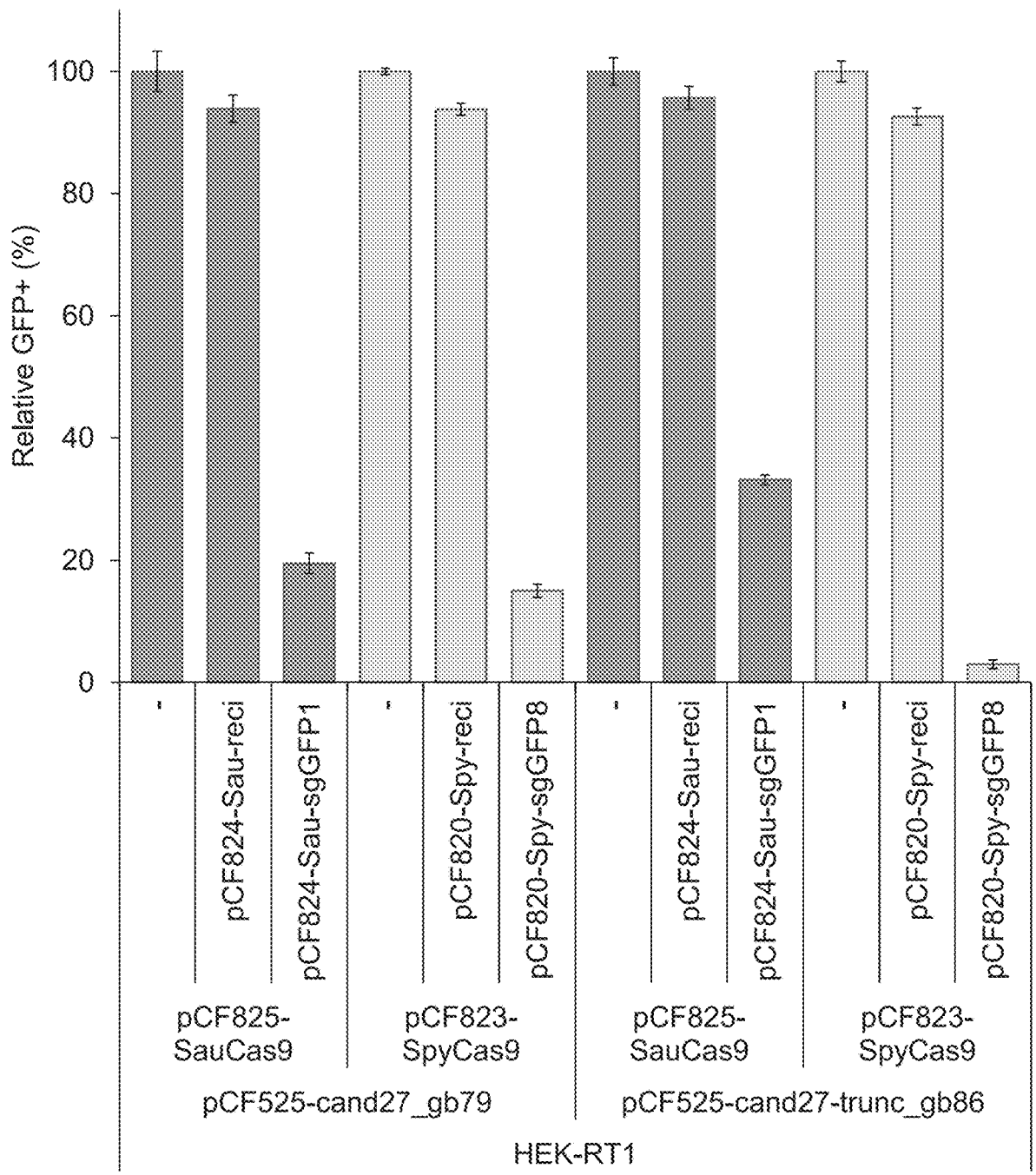
FIG. 9 depicts the effect of Aca cand27 and Aca cand27 Ntrunc on SauCas9/guide RNA activity or on SpyCas9/guide RNA activity in a human cell line.

The Aca cand27 and Aca cand27-N-trunc proteins were also tested. The data are shown in FIG. 9. The experimental set up was similar to that described for FIG. 8. The data indicate that the Aca cand27-N-trunc protein inhibits Sau-Cas9/guide RNA from cleaving the target nucleic acid.

Figure 10:
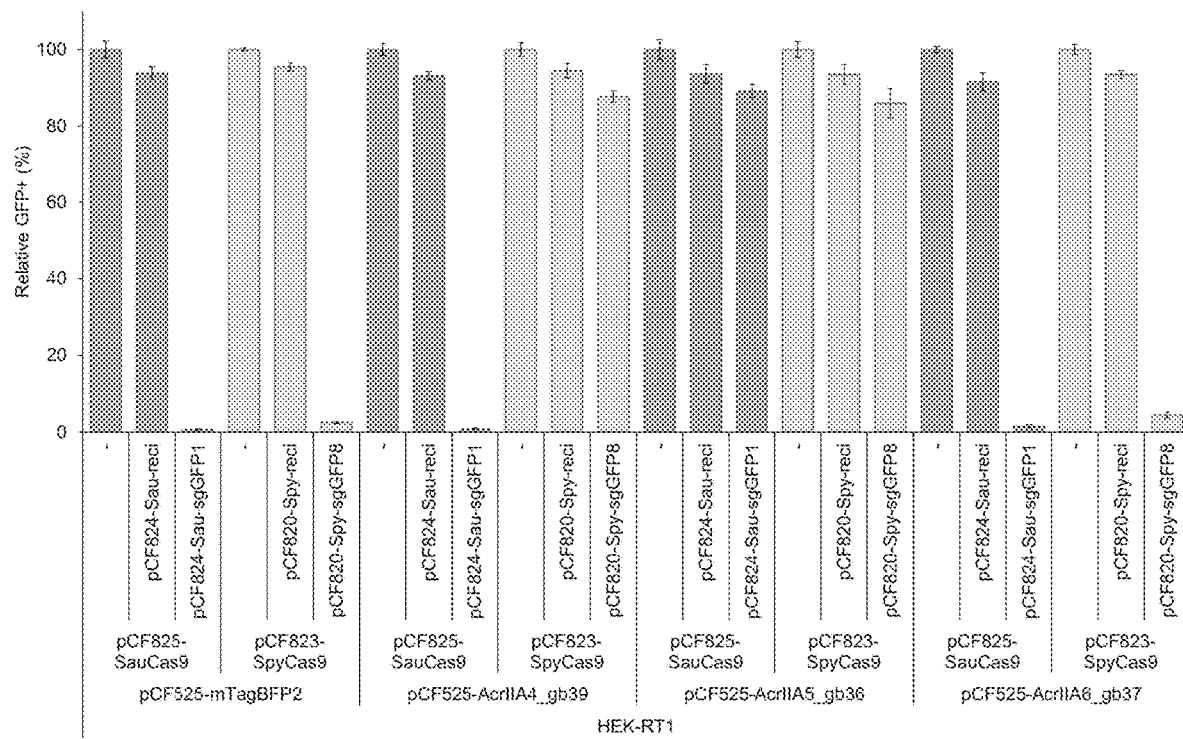
FIG. 10 depicts the effect of BFP2, AcrIIA4, AcrIIA5, and AcrIIA6 on SauCas9/guide RNA activity or on SpyCas9/guide RNA activity in a human cell line.

FIG. 10 shows the results for control proteins BFP2, AcrIIA4, AcrIIA5, and AcrIIA6. Bars 1-6 depict the results in which a negative control protein, BFP2, is expressed in place of Aca cand9 or Aca Cand27 and demonstrate no inhibition of either the SauCas9/guide complex or SpyCas9/guide complex. Bars 7-12 depict the results when the Spy Cas9 inhibitor AcrIIA4 is expressed and show that the experimental system is consistent with previously published findings by demonstrating that AcrIIA4 inhibits the activity of the SpyCas9/guide RNA complex but not the SauCas9/guide RNA complex. Bars 13-19 demonstrate the results with the SauCas9 and SpyCas9 inhibitor AcrIIA5, showing that AcrIIA5 inhibited both the SauCas9/guide RNA complex and the SpyCas9/guide RNA complex. Bars 20-26 depict the results with the StlCas9 inhibitor AcrIIA6, demonstrating that this protein does not inhibit activity of either the SauCas9/guide RNA complex or the SpyCas9/guide RNA complex.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A fusion polypeptide comprising:
   a) anti-CRISPR (Acr) polypeptide that is an inhibitor of an enzymatic activity of a Cas9 polypeptide, wherein the Acr polypeptide comprises an amino acid sequence having at least 95% amino acid sequence identity to the amino acid sequence set forth any one of SEQ ID NOs:1-4; and
   b) a heterologous fusion partner.

2. The fusion polypeptide of claim 1, wherein the heterologous fusion partner is a nuclear localization sequence.

3. The fusion polypeptide of claim 1, wherein the heterologous fusion partner is an epitope tag.

4. The fusion polypeptide of claim 1, wherein the Acr polypeptide lacks the 54-64 amino-terminal amino acids of the amino acid sequence set forth in SEQ ID NO:1; and wherein the Acr polypeptide has a length of from 95 amino acids to 105 amino acids.

5. The fusion polypeptide of claim 1, wherein the Acr polypeptide lacks the 51-61 amino-terminal amino acids of the amino acid sequence set forth in SEQ ID NO:2; and wherein the Acr polypeptide has a length of from 109 amino acids to 119 amino acids.

6. The fusion polypeptide of claim 1, wherein the Acr polypeptide comprises an amino acid sequence having at least 98% amino acid sequence identity to the amino acid sequence set forth in SEQ ID NO:1.

7. The fusion polypeptide of claim 1, wherein the Acr polypeptide comprises an amino acid sequence having at least 98% amino acid sequence identity to the amino acid sequence set forth in SEQ ID NO:2.

8. The fusion polypeptide of claim 1, wherein the Acr polypeptide comprises an amino acid sequence having at least 98% amino acid sequence identity to the amino acid sequence set forth in SEQ ID NO:3.

9. The fusion polypeptide of claim 1, wherein the Acr polypeptide comprises an amino acid sequence having at least 98% amino acid sequence identity to the amino acid sequence set forth in SEQ ID NO:4.

10. The fusion polypeptide of claim 1, wherein the heterologous fusion partner is a chloroplast transit peptide.

11. The fusion polypeptide of claim 1, wherein the heterologous fusion partner is an endosomal escape peptide.

12. The fusion polypeptide of claim 1, wherein the heterologous fusion partner is a protein transduction domain.

13. The fusion polypeptide of claim 1, wherein the fusion polypeptide comprises a linker between the Acr polypeptide and the heterologous fusion partner.

14. The fusion polypeptide of claim 2, wherein the nuclear localization sequence is selected from the amino acid sequence set forth in any one of SEQ ID NOs:7-22.

15. The fusion polypeptide of claim 12, wherein the protein transduction domain is selected from the amino acid sequence set forth in any one of SEQ ID NOs:23-32.

16. The fusion polypeptide of claim 13, wherein the linker is selected from the amino acid sequence set forth in any one of SEQ ID NOs:34-41.

17. The fusion polypeptide of claim 6, wherein the Acr polypeptide lacks the 54-64 amino-terminal amino acids of the amino acid sequence set forth in SEQ ID NO:1; and wherein the Acr polypeptide has a length of from 95 amino acids to 105 amino acids.

18. The fusion polypeptide of claim 8, wherein the Acr polypeptide lacks the 54-64 amino-terminal amino acids of the amino acid sequence set forth in SEQ ID NO:1; and wherein the Acr polypeptide has a length of from 95 amino acids to 105 amino acids.

19. The fusion polypeptide of claim 7, wherein the Acr polypeptide lacks the 51-61 amino-terminal amino acids of the amino acid sequence set forth in SEQ ID NO:2; and wherein the Acr polypeptide has a length of from 109 amino acids to 119 amino acids.

20. The fusion polypeptide of claim 9, wherein the Acr polypeptide lacks the 51-61 amino-terminal amino acids of the amino acid sequence set forth in SEQ ID NO:2; and wherein the Acr polypeptide has a length of from 109 amino acids to 119 amino acids.

\* \* \* \* \*